US012593998B2

(12) United States Patent
    Hunt et al.

(10) Patent No.: US 12,593,998 B2
(45) Date of Patent: Apr. 7, 2026

(54) DEVICE, APPARATUS AND METHOD OF DETERMINING SKIN PERFUSION PRESSURE

(71) Applicant: Smith & Nephew PLC, Watford (GB)

(72) Inventors: Allan Kenneth Frazer Grugeon Hunt, Beverley (GB); Peter Georg Laitenberger, Cambridge (GB); Lee Ian Partington, Hessle (GB); Marcus Damian Phillips, Wakefield (GB); Felix Clarence Quintanar, Hull (GB)

(73) Assignee: Smith & Nephew PLC, Watford (GB)

( * ) Notice: Subject to any disclaimer, the term of this patent is extended or adjusted under 35 U.S.C. 154(b) by 62 days.

(21) Appl. No.: 18/443,146

(22) Filed: Feb. 15, 2024

(65) Prior Publication Data

US 2024/0298911 A1      Sep. 12, 2024

Related U.S. Application Data

(63) Continuation of application No. 17/275,594, filed as application No. PCT/EP2019/074254 on Sep. 11, 2019, now Pat. No. 11,944,418.

(30) Foreign Application Priority Data

Sep. 12, 2018    (GB) ...................................... 1814814
Sep. 13, 2018    (GB) ...................................... 1814872

(51) Int. Cl.
    *A61B 5/026*          (2006.01)
    *A61B 5/00*           (2006.01)
                (Continued)

(52) U.S. Cl.
    CPC .......... *A61B 5/0261* (2013.01); *A61B 5/0004* (2013.01); *A61B 5/022* (2013.01);
                (Continued)

(58) Field of Classification Search
    CPC ..... A61B 5/0261; A61B 5/0004; A61B 5/022; A61B 5/0265; A61B 5/4836;
                (Continued)

(56) References Cited

U.S. PATENT DOCUMENTS 3,896,802  A      7/1975   Williams
4,334,530  A      6/1982   Hassell
                (Continued)

FOREIGN PATENT DOCUMENTS

CN          105232229  A      1/2016
CN          105395184  A      3/2016
                (Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).
                (Continued)

*Primary Examiner* — Jennifer Robertson
*Assistant Examiner* — Elina Sohyun Jang
(74) *Attorney, Agent, or Firm* — Knobbe, Martens, Olson & Bear, LLP

(57)          ABSTRACT

Disclosed embodiments relate to apparatuses and methods for a skin perfusion pressure determination device. In some embodiments, a skin perfusion pressure determination device can include a sensor module including a first sensor for sensing a first parameter associated with a pressure exerted on a target area by the sensor module and a second sensor for sensing a second parameter associated with an amount of blood perfusion at the target area, wherein the first sensor and the second sensor are arranged such that, when the sensor module is pressed against the target area the first sensor produces an output corresponding to the sensed first
                (Continued)

parameter and the second sensor produces an output corresponding to the sensed second parameter, a proximal end assembly configured to contact the target area, a display to provide feedback of the pressure exerted on a target area and/or the amount of blood perfusion at the target area, and a communication device for providing data transfer from the skin perfusion pressure determination device to a control unit.

19 Claims, 57 Drawing Sheets

(51) Int. Cl.
    *A61B 5/022*          (2006.01)
    *A61B 5/0265*         (2006.01)
(52) U.S. Cl.
    CPC .......... *A61B 5/0265* (2013.01); *A61B 5/4836*
                (2013.01); *A61B 5/6843* (2013.01); *A61B*
                                        *5/742* (2013.01)
(58) Field of Classification Search
    CPC ....... A61B 5/6843; A61B 5/742; A61B 5/026;
                            A61B 5/445; A61B 5/0053
    See application file for complete search history.

(56)                    References Cited

U.S. PATENT DOCUMENTS

| | | | |
|---|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,014,611 B1 | 3/2006 | Geddes et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,366,692 B2 | 2/2013 | Weston et al. |
| 8,480,641 B2 | 7/2013 | Jacobs |
| 8,525,340 B2 | 9/2013 | Eckhardt et al. |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,380,698 B1 | 6/2016 | Li et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,166,387 B2 | 1/2019 | Bergelin et al. |
| 10,182,740 B2 | 1/2019 | Tonar et al. |
| 10,206,604 B2 | 2/2019 | Bergelin et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,687,984 B2 | 6/2020 | Rovaniemi |
| 10,702,153 B2 | 7/2020 | Shamim et al. |
| 10,716,490 B2 | 7/2020 | Connolly |
| 10,857,038 B2 | 12/2020 | Zamierowski et al. |
| 11,026,847 B2 | 6/2021 | Piotrowski et al. |
| 11,229,553 B2 | 1/2022 | Chen et al. |
| 11,647,922 B2 | 5/2023 | Scherer |
| 11,850,121 B2 | 12/2023 | Rapp |
| 2002/0016536 A1 | 2/2002 | Benni |

(56) References Cited

U.S. PATENT DOCUMENTS

| | | |
|---|---|---|
| 2002/0135752 A1 | 9/2002 | Sokolov et al. |
| 2003/0033032 A1 | 2/2003 | Lind et al. |
| 2003/0036690 A1 | 2/2003 | Geddes et al. |
| 2003/0036751 A1 | 2/2003 | Anderson et al. |
| 2003/0208148 A1 | 11/2003 | Sullivan |
| 2003/0210810 A1 | 11/2003 | Gee et al. |
| 2003/0216630 A1 | 11/2003 | Jersey-Willuhn et al. |
| 2004/0034293 A1 | 2/2004 | Kimball |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2005/0281445 A1 | 12/2005 | Marcotte et al. |
| 2006/0052678 A1 | 3/2006 | Drinan et al. |
| 2006/0058690 A1 | 3/2006 | Bartnik et al. |
| 2006/0129039 A1 | 6/2006 | Lindner et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2006/0276700 A1 | 12/2006 | O'Neil et al. |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0209896 A1 | 8/2009 | Selevan |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0165717 A1 | 6/2012 | Al Khaburi |
| 2012/0166680 A1 | 6/2012 | Masoud et al. |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0066172 A1 | 3/2013 | Kulcke |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0236019 A1 | 8/2014 | Rahum |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0073271 A1 | 3/2015 | Lee et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0223749 A1 | 8/2015 | Park et al. |
| 2015/0257644 A1 | 9/2015 | Cao |
| 2015/0265191 A1 | 9/2015 | Harding et al. |
| 2015/0282748 A1 | 10/2015 | Hamaguchi et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0296716 A1* | 10/2016 | Cabiri ................ A61M 5/5086 |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |

(56) References Cited

U.S. PATENT DOCUMENTS

| | | |
|---|---|---|
| 2016/0338591 A1 | 11/2016 | Lachenbruch et al. |
| 2016/0346164 A1 | 12/2016 | Ward et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0003579 A1 | 1/2018 | Esposito et al. |
| 2018/0008177 A1 | 1/2018 | Shimuta et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0128681 A1 | 5/2018 | Otsuka |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0014995 A1 | 1/2019 | Kanaumi et al. |
| 2019/0021911 A1 | 1/2019 | Askem et al. |
| 2019/0038014 A1 | 2/2019 | Greer, Jr. et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A2 | 8/2019 | Askem et al. |
| 2019/0290496 A1 | 9/2019 | Brownhill et al. |
| 2019/0313998 A1* | 10/2019 | Lim ................... G08C 19/00 |
| 2019/0350470 A1 | 11/2019 | Khachaturian et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0281512 A1 | 9/2020 | Grubb et al. |
| 2020/0281513 A1 | 9/2020 | Grubb et al. |
| 2020/0281529 A1 | 9/2020 | Grubb et al. |
| 2020/0289346 A1 | 9/2020 | Hansen et al. |
| 2020/0306516 A1* | 10/2020 | Jones ................... A61B 5/4255 |
| 2020/0330258 A1 | 10/2020 | Hansen et al. |
| 2020/0360547 A1 | 11/2020 | Smith et al. |
| 2021/0137446 A1 | 5/2021 | Brownhill et al. |
| 2021/0145359 A1 | 5/2021 | Hunt et al. |
| 2021/0212855 A1 | 7/2021 | Hansen et al. |

FOREIGN PATENT DOCUMENTS

| | | |
|---|---|---|
| CN | 106102322 A | 11/2016 |
| CN | 109350362 A | 2/2019 |
| DE | 102012211015 A1 | 1/2014 |
| DE | 102013013013 A1 | 2/2015 |
| EP | 2454990 A2 | 5/2012 |
| EP | 2565630 A1 | 3/2013 |
| EP | 3231478 A1 | 10/2017 |
| EP | 3409190 A1 | 12/2018 |
| EP | 3424417 A1 | 1/2019 |
| EP | 3499510 A1 | 6/2019 |
| EP | 3837520 A1 | 6/2021 |
| GB | 1476894 A | 6/1977 |
| GB | 2316171 A | 2/1998 |
| GB | 2563602 A | 12/2018 |
| JP | 2006280770 A | 10/2006 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-9415531 A1 | 7/1994 |
| WO | WO-0021433 A1 | 4/2000 |
| WO | WO-0043046 A2 | 7/2000 |
| WO | WO-0185024 A1 | 11/2001 |
| WO | WO-03067229 A1 | 8/2003 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-2009052607 A1 | 4/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A2 | 3/2013 |
| WO | WO-2014036577 A1 | 3/2014 |
| WO | WO-2014094173 A1 | 6/2014 |
| WO | WO-2014116816 A1 | 7/2014 |
| WO | WO-2015047015 A1 | 4/2015 |
| WO | WO-2015112095 A1 | 7/2015 |
| WO | WO-2015168720 A1 | 11/2015 |
| WO | WO-2016022295 A1 | 2/2016 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016110564 A1 | 7/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017201419 A1 | 11/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |

(56) References Cited

FOREIGN PATENT DOCUMENTS

| | | | |
|---|---|---|---|
| WO | WO-2018144946 A1 | 8/2018 | |
| WO | WO-2018185138 A1 | 10/2018 | |
| WO | WO-2018189265 A1 | 10/2018 | |
| WO | WO-2018209090 A1 | 11/2018 | |
| WO | WO-2018211458 A1 | 11/2018 | |
| WO | WO-2018234443 A1 | 12/2018 | |
| WO | WO-2019020550 A2 | 1/2019 | |
| WO | WO-2019020551 A1 | 1/2019 | |
| WO | WO-2019020666 A1 | 1/2019 | |
| WO | WO-2019030384 A2 | 2/2019 | |
| WO | WO-2019048624 A1 | 3/2019 | |
| WO | WO-2019048626 A1 | 3/2019 | |
| WO | WO-2019048638 A1 | 3/2019 | |
| WO | WO-2019063481 A1 | 4/2019 | |
| WO | WO-2019063488 A2 | 4/2019 | |
| WO | WO-2019067264 A1 | 4/2019 | |
| WO | WO-2019072531 A1 | 4/2019 | |
| WO | WO-2019076967 A2 | 4/2019 | |
| WO | WO-2019096828 A1 | 5/2019 | |
| WO | WO-2019140441 A2 | 7/2019 | |
| WO | WO-2019140444 A1 | 7/2019 | |
| WO | WO-2019140448 A1 | 7/2019 | |
| WO | WO-2019140449 A1 | 7/2019 | |
| WO | WO-2019193141 A1 | 10/2019 | |
| WO | WO-2019216883 A1 | 11/2019 | |
| WO | WO-2019230183 A1 | 12/2019 | |
| WO | WO-2019238180 A1 | 12/2019 | |
| WO | WO-2019238181 A1 | 12/2019 | |
| WO | WO-2019238182 A1 | 12/2019 | |
| WO | WO-2019238195 A1 | 12/2019 | |
| WO | WO-2019238196 A1 | 12/2019 | |
| WO | WO-2019238197 A1 | 12/2019 | |
| WO | WO-2019238198 A1 | 12/2019 | |
| WO | WO-2020002416 A1 | 1/2020 | |
| WO | WO-2020043806 A1 | 3/2020 | |
| WO | WO-2020053290 A1 | 3/2020 | |
| WO | WO-2020139541 A1 | 7/2020 | |
| WO | WO-2020157103 A1 | 8/2020 | |
| WO | WO-2020159677 A1 | 8/2020 | |
| WO | WO-2020167547 A1 | 8/2020 | |
| WO | WO-2020242876 A1 | 12/2020 | |

OTHER PUBLICATIONS

Bandodkar A.J., et al., "Battery-Free, Skin-Interfaced Microfluidic/ Electronic Systems for Simultaneous Electrochemical, Colorimetric and Volumetric Analysis of Sweat," Science Advances, vol. 5 (1), Jan. 18, 2019, retrieved from http://advances.sciencemag.org/content/ 5/1/eaav3294, 16 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

George J., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Hu F., et al., "Intelligent Sensor Networks: The Integration of Sensor Networks, Signal Processing and Machine Learning," 2013, Auberach Publications, pp. 3-5.

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Preliminary Report on Patentability and Written Opinion for Application No. PCT/EP2019/074254, mailed on Mar. 25, 2021, 10 pages.

International Preliminary Report on Patentability for Application No. PCT/EP2018/055940, mailed on Sep. 19, 2019, 9 pages.

International Search Report and Written Opinion for Application No. PCT/EP2018/055940, mailed on Sep. 3, 2018, 12 pages.

International Search Report and Written Opinion for Application No. PCT/EP2019/074254, mailed on Dec. 5, 2019.

Invitation to Pay Additional Fees and Partial Search Report for Application No. PCT/EP2018/055940, mailed on Jun. 12, 2018, 8 pages.

Little Miss Plasters, kidstravelclub.co.uk., retrieved from http:// www.kidstravelclub.co.uk/little-miss-girls-childrens-plasters on Aug. 26, 2016, 2 pages.

Lu B., et al., "A Study of the Autofluorescence of Parylene Materials for µTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE— International Society for Optical Engineering, Mar. 12, 2014, vol. 9036, 8 pages.

Mehmood N., et al., "Applications of Modern Sensors and Wireless Technology in Effective Wound Management: Modern Sensors and Wireless Technology," Journal of Biomedical Materials Research Part B, vol. 102, May 1, 2014, XP055739544, pp. 885-895.

Mostafalu P., et al., "Wireless Flexible Smart Bandage for Continuous Monitoring of Wound Oxygenation," IEEE Transactions on Biomedical Circuits and Systems, vol. 9 (5), Oct. 1, 2015, XP055526132, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ ke-english-corona/CORONA_DISCHARGE_EN.pdf, 12 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng. com/wp-content/uploads/2017/11/Conformal-Coating-Inspection- and-Defects.21JUL16.pdf, 35 pages.

Willis B., "Guide to Conformal Coating & Cleaning Defects Contents," Mar. 1, 2014, retrieved from http://coatingguide.smartgroup. org/Files%20pdf/Coating%20Defects%20V2%2014March2014. pdf, vol. 1, 31 pages.

* cited by examiner 804
806
803
804
805

807
805

904

923

906

903

921

922

909

905

1109 ⟶

1109

1109 $\longrightarrow$

1109 $\longrightarrow$

1109 $\longrightarrow$

1209 ⟶

1209 ⟶

Fifure. 13A

1309 ⟶

1309 ⟶

1309 →

1309 →

1410

1405

1410

1412

1415

1411

1413

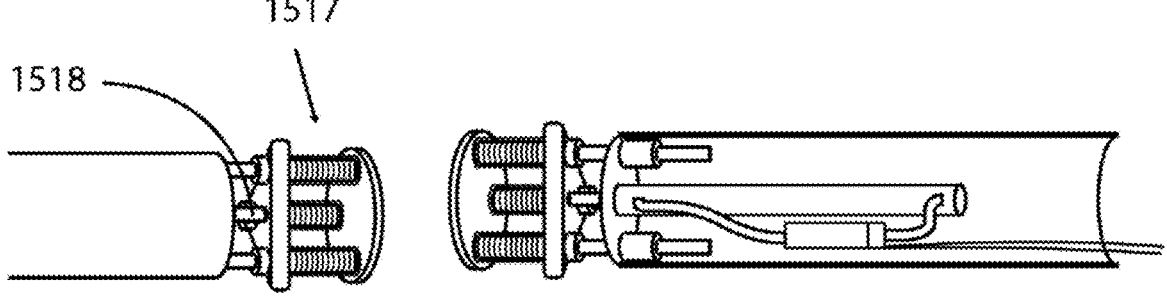
Figure. 15C                    Figure. 15D

DEVICE, APPARATUS AND METHOD OF DETERMINING SKIN PERFUSION PRESSURE

CROSS-REFERENCE TO RELATED APPLICATIONS

The present application is a continuation of U.S. application Ser. No. 17/275,594, filed Mar. 11, 2021, which is a national stage application under 35 U.S.C. § 371 of International Application No. PCT/EP2019/074254, filed on Sep. 11, 2019, and which claims priority to GB 1814814.8, titled "DEVICE, APPARATUS AND METHOD OF DETERMINING SKIN PERFUSION PRESSURE" and filed on Sep. 12, 2018, and Application No. GB 1814872.6, filed Sep. 13, 2018, titled "DEVICE, APPARATUS AND METHOD OF DETERMINING SKIN PERFUSION PRESSURE," the contents of which are hereby expressly incorporated by reference in their entirety.

FIELD

Embodiments of the present disclosure relate to apparatuses, systems, and methods for the treatment of tissues via sensor-enabled monitoring in communication with various therapy regimes. Embodiments described herein relates to a skin perfusion pressure determination device, apparatus and method of determining skin perfusion pressure.

BACKGROUND

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

Wound healing is natural process performed by the human body in response to injury. The amount of time taken for a wound to heal is dependent on many different factors which include the human body's ability to heal itself and any treatments that are applied to the wound to accelerate wound healing. Understanding the healing status of a wound and being able to monitor the healing process helps to inform decisions on further treatment of the wound and can also assist in the development of future wound therapies.

One factor that is known to be correlated with wound healing is the Skin Perfusion Pressure (SPP) in tissue adjacent the wound. SPP is the amount of pressure required to restore blood flow to blood vessels within skin tissue following a controlled occlusion of the blood vessels using a blood pressure cuff.

Techniques for detecting the restoration of blood flow include radioisotope clearance, laser doppler flow measurement and photoplethysmography. Such techniques are typically performed by clinicians and require instrumentation that is often bulky, complicated and expensive.

Additionally, a wound dressing is typically applied to a wound in order to protect the wound from pathogens, assist healing of the wound and to protect the area of the wound from further injury. In order to assess healing, the tissue in and around the wound may be inspected periodically. Inspection can be carried out by a clinician using the naked eye, but may also be carried out using optical devices that analyze the appearance of the wounded area to determine the state of the wound. To access the wounded area, the wound dressing must be removed. This is time consuming, inconvenient and often uncomfortable for the patient. Moreover, the original dressing is usually replaced by a fresh dressing even though the old dressing may not have needed replacing at the time of inspection In order to assess healing, a probe or other form of inspection device may be used to measure a parameter associated with wound healing at various points about the perimeter of the wound dressing or at various tissue areas. One example is the measurement of the amount of blood perfusion in the tissue surrounding the wound. The amount of blood perfusion will, however, vary about the periphery of the wound dressing. For example, the amount of blood perfusion of tissue at the periphery of a wound to a forearm may be greater in tissue closer to the elbow than in tissue closer to the wrist. Repeated measurements at different locations by clinicians can therefore produce results which are inconsistent and unreliable for determining the status of the healing process.

SUMMARY

It is an aim of the embodiments described herein to at least partly mitigate the above-mentioned problems.

According to one embodiment, a skin perfusion pressure determination device can comprise a housing including a proximal end and a distal end. The skin perfusion pressure determination device can further comprise a proximal end assembly at the proximal end of the housing configured to contact and exert pressure on a target area, a sensor module provided within the housing and/or the proximal end assembly configured to detect a pressure exerted on the target area and an amount of blood perfusion at the target area, a display to provide feedback of the pressure exerted on the target area and/or the amount of blood perfusion at the target area, and a communication device for transferring data from the skin perfusion pressure determination device to a control unit.

The skin perfusion pressure determination device of the preceding paragraph or in other embodiments can include one or more of the following features. In some embodiments, the communication device can comprise an integrated USB connector at the distal end of the housing; and/or the skin perfusion pressure determination device can further comprise a USB end cap configured to be removably coupled to the distal end of the housing and cover an integrated USB connector when it is not in use; and/or wherein the display can comprise an LED circumferential display positioned on the proximal end of the housing; and/or the housing can further comprise a grip portion configured to provide a surface for holding and controlling the skin perfusion pressure determination device, wherein the grip portion comprises contoured sides of the housing and is positioned on the proximal end of the housing distal to the LED circumferential display; and/or the proximal end assembly can further comprise a bellows portion configured to contract when the proximal end assembly is in contact with the target area and force is applied from the skin perfusion pressure determination device to the target area. In some embodiments, the housing can comprise a waisted bulb shape and the distal end of the housing comprises a rounded surface; and/or the communication device can comprise a device for wireless communication; and/or the display can comprise an LED circumferential display positioned on the proximal end of the housing; and/or the housing can further comprise a first grip portion and/or a second grip portion configured to provide a surface for holding and controlling the skin perfusion pressure determination device, wherein the first grip portion comprises a waisted contour of the housing and is positioned on the proximal end of the housing distal to the LED circumferential display, wherein the second grip portion comprises the rounded surface of the distal end. In some embodiments, the display can comprise a screen on the distal most end of the housing; and/or the communication device can comprise a device for wireless communication; and/or the housing can further comprise a switch configured to turn the skin perfusion pressure determination device on or off; and/or the housing can further comprise a grip portion configured to provide a surface for holding and controlling the skin perfusion pressure determination device, wherein the grip portion comprises a grip material positioned on the proximal end of the housing proximal to the screen; and/or the proximal end assembly can further comprise a bellows portion configured to contract when the proximal end assembly is in contact with the target area and force is applied from the skin perfusion pressure determination device to the target area. In some embodiments, the housing can further comprises a grip portion configured to provide a surface for holding and controlling the skin perfusion pressure determination device, wherein the grip portion comprises a grip material positioned on the proximal end of the housing; and/or the housing can comprise a tapered distal end; and/or the display can comprise an LED display positioned on the housing distal to the grip portion and proximal to the tapered distal end; and/or the proximal end assembly can further comprise a bellows portion configured to contract when the proximal end assembly is in contact with the target area and force is applied from the skin perfusion pressure determination device to the target area; and/or the communication device can comprise a device for wireless communication and/or an electrical wiring connecting the skin perfusion pressure determination device to a control unit. In some embodiments, the communication device can comprise an electrical wiring connecting the skin perfusion pressure determination device to a control unit; and/or the display can comprise a plurality of LED displays on the distal end of the housing, wherein a first LED display of the plurality of LED displays comprises a top display on the distal most end of the housing and a second LED display of the plurality of LED displays comprises a side display on a side of the distal end of the housing; and/or the housing can further comprise a grip portion configured to provide a surface for holding and controlling the skin perfusion pressure determination device, wherein the grip portion comprises a grip material positioned on the proximal end of the housing; and/or the proximal end assembly can further comprise a bellows portion configured to contract when the proximal end assembly is in contact with the target area and force is applied from the skin perfusion pressure determination device to the target area.

According to another embodiment, a skin perfusion pressure determination device can comprise a housing including a proximal end and a distal end, and wherein the skin perfusion pressure determination device can further comprise a proximal end assembly at the proximal end of the housing configured to contact and exert pressure on a target area, and a sensor module provided within the housing and/or the proximal end assembly configured to detect a pressure exerted on the target area and an amount of blood perfusion at the target area, wherein the proximal end assembly comprises a bellows portion configured to contract when the proximal end assembly is in contact with the target area and force is applied from the skin perfusion pressure determination device to the target area.

The skin perfusion pressure determination device of the preceding paragraphs or in other embodiments can include one or more of the following features. In some embodiments, the proximal end assembly can comprise a bellows portion comprising a waisted shape that is configured to contract inward when the force is applied or the bellows portion comprises a diamond, bulbous or toroidal shape configured to contract and extend outward when the force is applied.

According to another embodiment, a skin perfusion pressure determination device can comprise a housing including a proximal end and a distal end, and wherein the skin perfusion pressure determination device can further comprise a proximal end assembly at the proximal end of the housing configured to exert a pressure on a target area, wherein the proximal end assembly comprises a withdrawal mechanism configured to automatically control the pressure exerted on the target area by the proximal end assembly, and a sensor module provided within the housing and/or the proximal end assembly configured to detect a pressure exerted on the target area and an amount of blood perfusion at the target area.

The skin perfusion pressure determination device of the preceding paragraph or in other embodiments can include one or more of the following features. In some embodiments, the withdrawal mechanism can comprise a bellows device in fluid communication with a control valve, wherein the bellows device is configured to contract when the proximal end assembly is in contact with the target area and force is applied from the proximal end assembly to the target area, and wherein the bellows device is configured to expand when the control valve is opened allowing air to fill the bellows device. In some embodiments, the withdrawal mechanism can comprise a fluid damper device. In some embodiments, the fluid damper device can comprise a liquid filled piston comprising a proximal end and a distal end, the liquid filled piston comprises a first chamber at the distal end and a second chamber at the proximal end, the liquid filled piston in fluid communication with a control valve, a spring comprising a proximal end and a distal end, the spring positioned proximal to the liquid filled piston, and an intermediate platform positioned at the proximal end of the liquid filled piston and at the distal end of the spring, wherein when the control valve is closed the liquid fluid piston is fixed in a first position exerting a pressure on the intermediate platform and the spring, and wherein the control valve is configured to allow fluid to move from the first chamber to the second chamber of the fluid filled piston when it is opened thereby allowing the spring to expand and move the piston to a second position. In some embodiments, the withdrawal mechanism can comprise a magnetic brake device. In some embodiments, the magnetic brake device can comprise a magnetic clutch and a gear with teeth, a spring positioned at a proximal end of the proximal end assembly, a ratchet arm with teeth positioned distal to the spring and configured to exert a pressure on the spring in a first position, wherein the teeth of the ratchet arm are in communication with the teeth of the gear, wherein the magnetic brake device is configured to allow the gear to turn when a magnetic field is applied and when the gear is allowed to turn, the spring is allowed to expand moving the ratchet arm toward the distal end of the housing. In some embodiments, the withdrawal mechanism can comprise a magneto-rheological fluid device. In some embodiments, the magneto-rheological fluid device can comprise a magneto-rheological fluid, wherein the magneto-rheological fluid is configured to change viscosity in response to a change in a magnetic field applied to the magneto-rheological fluid, a reservoir comprising a first plunger on a proximal end of the reservoir and a second plunger on a distal end of the reservoir, wherein the first plunger and the second plunger are configured to move within the reservoir in a proximal to distal direction and/or a distal to proximal direction, wherein the magneto-rheological fluid is contained in the reservoir between the first plunger and the second plunger, a spring in communication with a proximal end of the first plunger, and a magnet and/or a coil wrapped around the reservoir and/or orifice containing the magneto-rheological fluid, wherein the magnet and/or coil are configured to generate the magnetic field, wherein the first and second plungers have a first proximal position comprising the first plunger extended from the proximal end of the reservoir and the viscosity of the magneto-rheological fluid prevents movement of the plungers within the reservoir and wherein the magnetic field is configured to change the viscosity of the magneto-rheological fluid to allow the magneto-rheological fluid to move within the reservoir thereby reducing the force exerted by the spring and allowing the spring to expand and move the first and second plungers to a second distal position comprising the first plunger within the reservoir.

According to another embodiment, a skin perfusion pressure determination device can comprise a housing including a proximal end and a distal end, and wherein the skin perfusion pressure determination device can further comprise a proximal end assembly at the proximal end of the housing comprising a control mechanism configured to automatically control the pressure exerted on a target area by the proximal end assembly, and a sensor module provided within the housing and/or the proximal end assembly and configured to detect a pressure exerted on the target area and an amount of blood perfusion at the target area.

The skin perfusion pressure determination device of the preceding paragraph or in other embodiments can include one or more of the following features. In some embodiments, control mechanism can comprise a pump driven device. In some embodiments, the pump driven device can comprise a reservoir, a pump in fluid communication with a control valve, wherein the pump is configured to pump air into the reservoir and/or allow air to escape from the reservoir and wherein the control valve is configured to control the amount of air that fills and/or escapes the reservoir, a rod configured to move within the reservoir and extend from the proximal end of the reservoir, and wherein the pump driven device has a first position wherein the reservoir is filled with air thereby causing the rod to extend from the proximal end of the reservoir to allow the skin perfusion pressure determination device to exert pressure on the target area, wherein the pump driven device has a second position wherein the rod is contained within the reservoir, and wherein the pump driven device is configured to move between the first position and the second position. In some embodiments, the control mechanism can comprise a motor driven device. In some embodiments, the motor driven device can comprise a motor, a lead-screw coupled to the motor and configured to move within the proximal end assembly in a proximal to distal and/or distal to proximal direction, a spring coupled to the lead-screw and configured to move within the proximal end assembly in a proximal to distal and/or distal to proximal direction and configured to adjust the force applied to the target tissue area by the proximal end assembly, wherein the lead-screw is configured to move in a proximal direction exerting a force on the spring which exerts a force on the target tissue area, wherein the lead-screw is configured to move in a distal direction releasing the force exerted on the spring, and wherein the lead-screw is configured to move between the proximal direction and the distal direction to control the pressure exerted on the target area.

The skin perfusion pressure determination device of the preceding paragraph or in other embodiments can include one or more of the following features. In some embodiments, the sensor module can comprise a first sensor for sensing a first parameter associated with a pressure exerted on the target area by the sensor module and a second sensor for sensing a second parameter associated with an amount of blood perfusion at the target area, wherein the first sensor and the second sensor are arranged such that, when the sensor module is pressed against the target area the first sensor produces an output corresponding to the sensed first parameter and the second sensor produces an output corresponding to the sensed second parameter. In some embodiments, the skin perfusion pressure determination device can further comprise a docking station configured to receive the skin perfusion pressure determination device. In some embodiments, the housing can be an elongate housing.

According to another embodiment, a skin perfusion pressure determination device can comprise a housing including a proximal end and a distal end. The skin perfusion pressure determination device can further comprise a plunger assembly at the proximal end of the housing configured to contact and exert force on a target area, the plunger assembly comprising a support structure and a sleeve surrounding the support structure, a sensor module provided within the housing and/or the plunger assembly, the sensor module configured to detect a force exerted on the target area and an amount of blood perfusion at the target area, a display to provide feedback of the force exerted on the target area, and a spring at the distal end of the housing configured to exert a force on the plunger assembly and control the force exerted on the target area.

The skin perfusion pressure determination device of the preceding paragraph or in other embodiments can include one or more of the following features. The display can comprise an indicator portion and an LED, wherein the indicator portion is configured to display the light emitted from the LED and the indicator portion circumferentially surrounds a portion of the housing. The support structure can support one or more of a sensor, electrical connection for a sensor, a PCB, a battery, battery contacts, and/or an LED.

The sensor module can comprise a first sensor for sensing a first parameter associated with a force exerted on the target area by the sensor module and a second sensor for sensing a second parameter associated with an amount of blood perfusion at the target area, wherein the first sensor and the second sensor are arranged such that, when the sensor module is pressed against the target area the first sensor produces an output corresponding to the sensed first parameter and the second sensor produces an output corresponding to the sensed second parameter. The sensor module can comprise a first sensor configured to detect the amount of blood perfusion at the target area and/or a second sensor configured to detect the force exerted on the target area. The first sensor and the second sensor can be positioned at a proximal end of the housing. The first sensor can be positioned at a proximal end of the housing and the second sensor is positioned at the distal end of the plunger assembly and proximal to the spring. The first sensor can be an optical sensor. The second sensor can be a force sensor. The housing can comprise a grip portion comprising a flared portion. The skin perfusion pressure determination device can further comprise a docking station configured to receive the skin perfusion pressure determination device. The housing can be an elongate housing. The housing can comprise a proximal end cap configured to contact the target area, wherein the proximal end cap comprises one or more of a flange shape, a dome shape, a curved shape, a tapered shape, or a nipple shape.

According to another embodiment, a method of determining skin perfusion pressure can comprise positioning a proximal end of a skin perfusion pressure determination device on a target area of patient, the skin perfusion pressure determination device comprising a bellows portion with a spring, applying a force to the skin perfusion pressure determination device against the target area, causing the bellows portion and spring to contract until blood flow has been occluded in the target area, releasing the force applied to the target area at a controlled rate by expanding the spring, detecting when blood flow resumes in the target area, and measuring or determining the force or pressure applied to the target area by the skin perfusion pressure determination device when the blood flow resumes.

According to another embodiment, a method of determining skin perfusion pressure, can comprise positioning a proximal end of a skin perfusion pressure determination device on a target area of patient, applying a force to the skin perfusion pressure determination device against the target area, measuring the force or a pressure applied to the target area by the skin perfusion pressure determination device using a first sensor within the device, and measuring blood perfusion in the target area beneath the proximal end using a second sensor within the device, wherein after the device detects that blood flow has been occluded in the target area, the device automatically withdraws the force applied to the target area at a controlled rate.

According to another embodiment, a method of determining skin perfusion pressure, can comprise positioning a proximal end of a skin perfusion pressure determination device on a target area of patient, applying a force to the skin perfusion pressure determination device against the target area, measuring the force or a pressure applied to the target area by the skin perfusion pressure determination device using a first sensor within the device, and measuring blood perfusion in the target area beneath the proximal end using a second sensor within the device, wherein the device controls the application and/or withdrawal of force by the skin perfusion pressure determination device against the target area.

The method of determining skin perfusion pressure of the preceding paragraph or in other embodiments can include one or more of the following features. In some embodiments, the method can comprise measuring the force or pressure applied the target area when blood flow in the target area resumes by withdrawal of force by the skin perfusion pressure determination device against the target area. In some embodiments, the second sensor can be used to measure when blood flow in the target area resumes.

According to another embodiment, a method of using or operating the skin perfusion pressure determination device of any of the preceding paragraphs.

According to another embodiment, a skin perfusion pressure determination device comprising one or more of the features described in the foregoing description.

According to another embodiment, a method of using or operating a skin perfusion pressure determination device comprising one or more features described in the foregoing description.

Other embodiments of a wound dressing, devices, kits and associated methods are described below.

BRIEF DESCRIPTION OF THE DRAWINGS

Embodiments of the present disclosure will now be described, by way of example only, with reference to the accompanying drawings in which:

FIGS. 13A-13K illustrate embodiments of a skin perfusion pressure determination device;

FIGS. 15A-15D illustrate an embodiment of a withdrawal mechanism with a fluid damper device;

FIGS. 20A-20C illustrate embodiments of protective covers for use with a skin perfusion pressure determination device;

DETAILED DESCRIPTION

Figure 1:
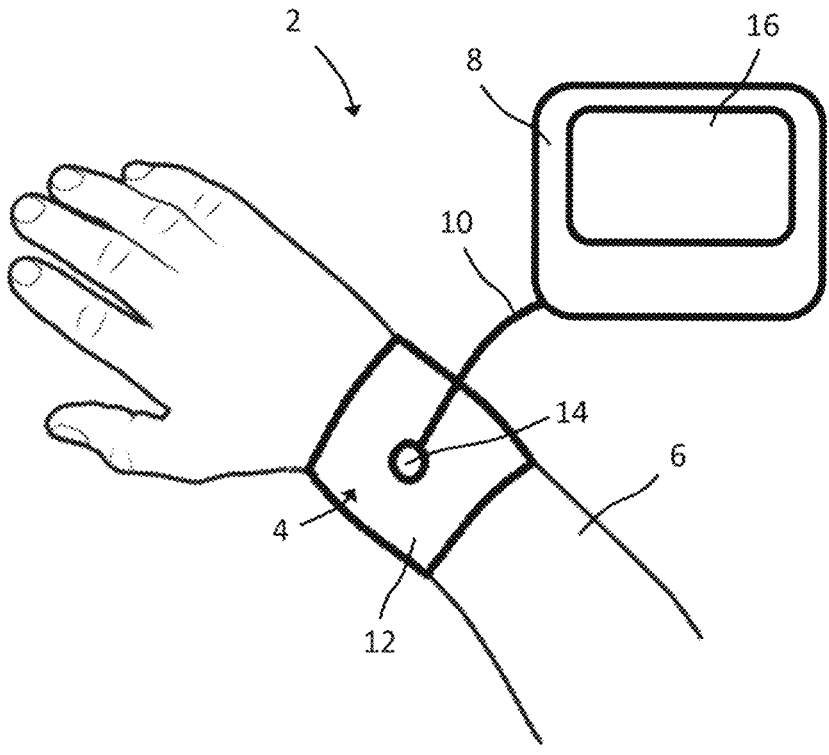
FIG. 1 is a schematic representation of a skin perfusion pressure determination device in use.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film. Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/

114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:

an absorbent layer for absorbing wound exudate and an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film. Typically, the translucent film has a moisture vapour permeability of 500 g/m2/24 hours or more.

The translucent film may be a bacterial barrier.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm2.

The support layer may have a tensile strength from 0.05 to 0.06 Nm.

The support layer may have a thickness of from 50 to 150 μm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of $(760-X)$ mmHg. In addition, negative pressure that is "less" or "smaller" than X mmHg corresponds to pressure that is closer to atmospheric pressure (such as, $-40$ mmHg is less than $-60$ mmHg). Negative pressure that is "more" or "greater" than $-X$ mmHg corresponds to pressure that is further from atmospheric pressure (such as, $-80$ mmHg is more than $-60$ mmHg). In some embodiments, local ambient atmospheric pressure is used as a reference point, and such local atmospheric pressure may not necessarily be, for example, 760 mmHg.

The negative pressure range for some embodiments of the present disclosure can be approximately $-80$ mmHg, or between about-20 mmHg and $-200$ mmHg. Note that these pressures are relative to normal ambient atmospheric pressure, which can be 760 mmHg. Thus, $-200$ mmHg would be about 560 mmHg in practical terms. In some embodiments, the pressure range can be between about-40 mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately $-100$ mmHg, or even $-150$ mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753, 894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRES-SURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

Skin Perfusion Pressure

FIG. 1 shows an apparatus 2 for determining skin perfusion pressure comprising a skin perfusion pressure determination device 4 secured to a patient's arm 6 and a monitoring device 8 connected via a lead 10 to the skin perfusion pressure determination device 4. The skin perfusion pressure determination device 4 comprises a wound dressing 12 and a sensor module 14 formed integrally with the wound dressing 12. The wound dressing 12 is in the form of a detachable band that may be secured to the arm 6 of the patient by wrapping it around the arm 6 and securing opposite end portions together using a fastener, such as an adhesive strip or hook and loop fastener or the like. In other embodiments the skin perfusion pressure determination device may be a detachable band that does not comprise a wound dressing but may be secured adjacent a wound if desired. Bands may be secured to other parts of an animal or person's body including other limbs, such as a leg, or a torso. The lead 10 is connected to the sensor module 14 at one end and to the monitoring device 8 at the other end. The lead 10 provides a means for communication between the sensor module 14 and the monitoring device 8 and also provides a means for supplying power to the sensor module 14. In some embodiments, the sensor module 14 can be included in a patch which is attached to the target area, using e.g. an adhesive. In such embodiments, the sensor module 14 does not need to be included in a band which is wrapped around the arm.

The monitoring device 8 is configured to receive and process a signal received from the sensor module 14 and display processed information on an integrated display 16.

Figure 2:
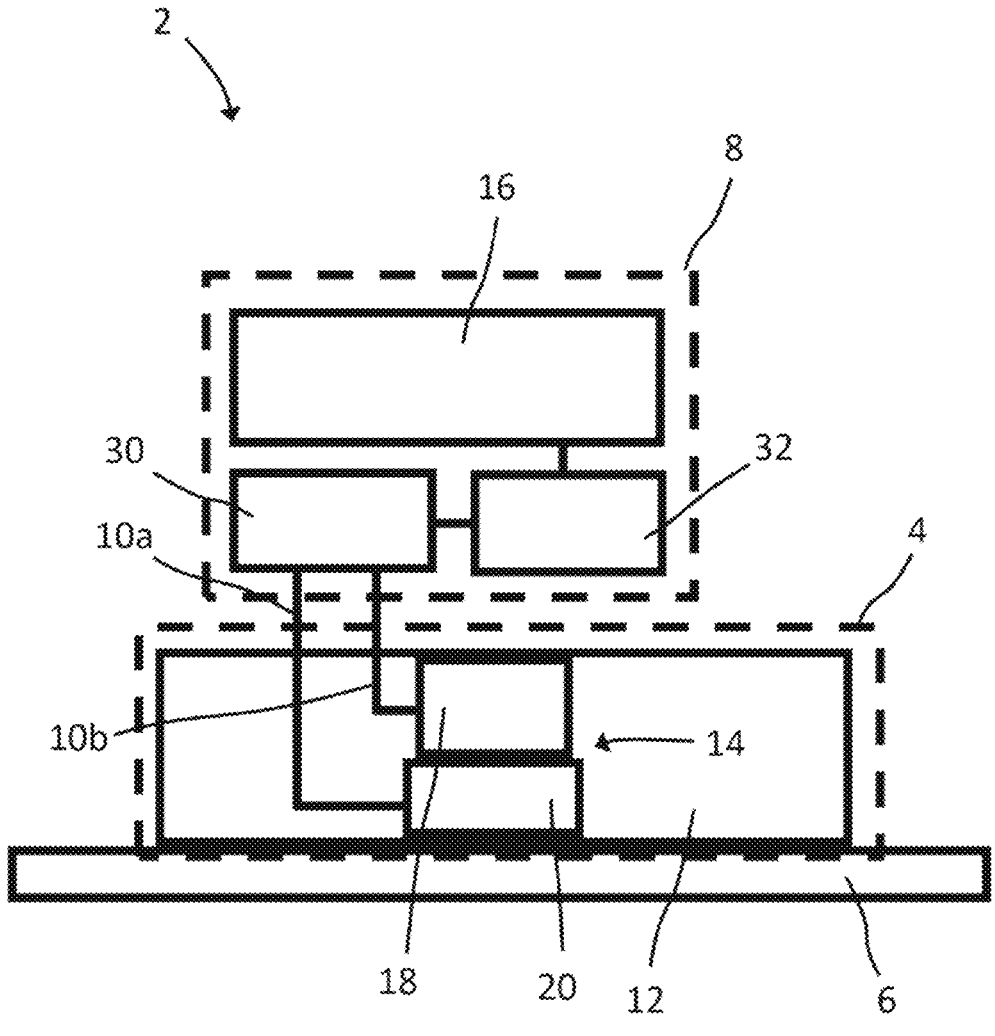
FIG. 2 is a schematic representation of components of the skin perfusion pressure determination device shown in FIG. 1.

FIG. 2 is a system diagram representing components of the apparatus 2 shown in FIG. 1.

FIG. 2 depicts components of the skin perfusion pressure determination device 4 and the monitoring device 8 which are enclosed, respectively, by broken lines. The sensor module 14 comprises a first sensor in the form of a force sensor 18 for sensing a force transmitted through the sensor module 14 to the patient's arm 6, and a second sensor in the form of an optical sensor 20 for sensing a parameter which corresponds to the amount of blood perfusion in the skin tissue of the arm 6 underneath the sensor module 14. In the present embodiment, the optical sensor 20 is a pulse sensor, but other suitable sensors may be used such as a reflective pulse oximeter sensor or the like. The force sensor 18 is a thin-film micro-force sensor with a diameter of 15 mm and a force range of 45N. The force sensor 18 also comprises associated read-out electronics.

The force sensor 18 is disposed on an upper portion of the optical sensor 20 and the optical sensor 20 is arranged such that it faces away from the force sensor 18 towards the arm 6.

The sensors 18, 20 are connected via respective electrical wires 10a, 10b, which comprise the lead 10, to an input of the monitoring device 8.

Figure 3:
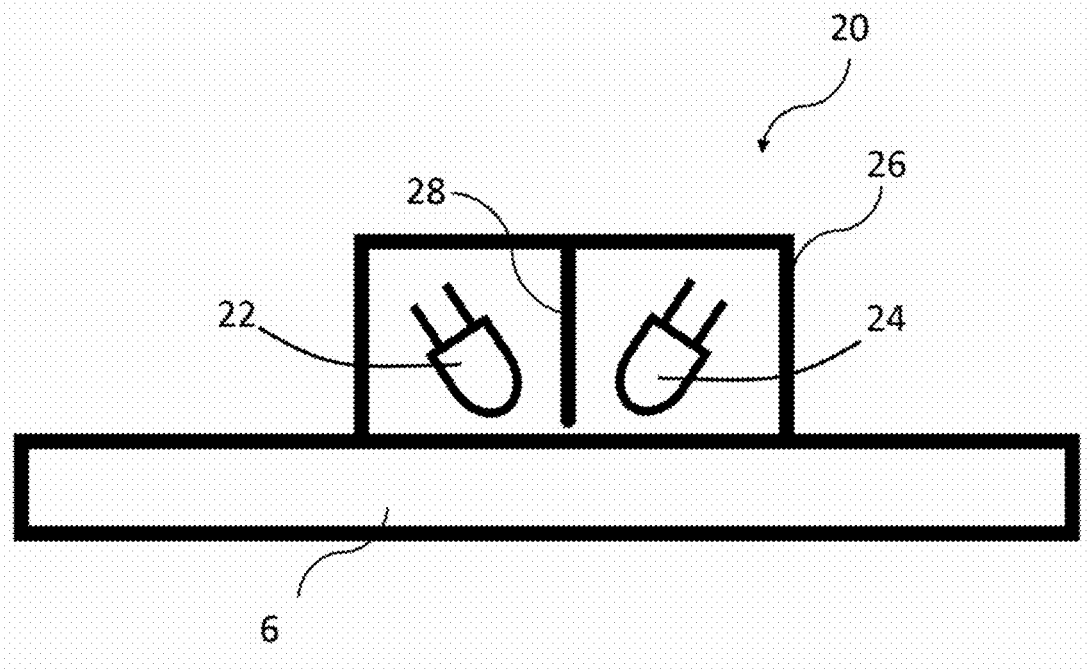
FIG. 3 is a schematic representation of a sensor for sensing a parameter associated with blood perfusion.

FIG. 3 is a schematic representation of the optical sensor 20 in isolation wherein the optical sensor 20 is located against the arm 6. The optical sensor 20 comprises a light emitter in the form of a light emitting diode (LED) 22 which emits light at a predetermined wavelength (or emits light across a predetermined range of wavelengths) and a light detector in the form of a photodiode 24 which is configured to detect light emitted by the LED 22.

The LED 22 and the photodiode 24 are disposed within a housing 26 and separated by a shield 28 which is opaque to the wavelength or range of wavelengths of light detectable by the photodiode 24. The shield 28 prevents emitted light from the LED being transmitted directly to the photodiode 24. The lower portion of the housing 26 is open or transparent so that light emitted by the LED 22 can pass through the lower portion to the skin tissue of the arm 6 and light reflected or scattered by the skin tissue of the arm 6 can pass back through the lower portion of the housing 26 to the photodiode 24. The shield 28 is spaced slightly from the skin tissue so that it does not contact the skin and so does not prevent light from passing underneath the shield 28. Light received by the photodiode 24 is therefore light which has been emitted by the LED 22 and either reflected, scattered or absorbed and reemitted by the skin tissue of the arm 6.

In the embodiment shown, the LED 22 emits light in the green band of the visible spectrum having a wavelength between 495 nm and 570 nm. Green light is known to be absorbed highly by hemoglobin within blood and so the amount of absorption of green light is correlated with the amount of blood in the skin tissue. Measuring the amount of absorption of green light emitted by the LED 22 can therefore be used to determine the amount of blood, and hence indicate the amount of blood perfusion, in a target area of tissue beneath the sensor module 14.

Referring again to FIG. 2, the monitoring device 8 comprises signal processing electronics 30 connected to the leads 10a, 10b and a processor 32 for processing signals received from the force sensor 18 and the optical sensor 20. The processor 32 is configured to display data representing the processed signals on the display 16. The signal processing electronics 30 are further configured to supply power to the sensor module 14. However, it will be appreciated that a separate power source may be provided, and that a power source may be integrated into the wound dressing. In other embodiments, the skin perfusion pressure determination device may comprise the processor and the processor may be configured to provide a digital output to the monitoring device.

A method of determining skin perfusion pressure using the apparatus 2 will now be described with reference to FIGS. 1 to 5.

The sensor module 14 is placed against the arm 6 of a patient so that the lower portion of the housing 26 of the sensor module 14, which is open or transparent, is adjacent the target area of skin tissue, as shown in FIG. 3. The lower portion of the housing 26 may be in contact with the target area. The skin perfusion pressure determination device 4 is then secured to a patient's arm 6 by wrapping the wound dressing 12 about the arm 6 and securing end portions of the wound dressing 12 together, as shown in FIG. 1. The sensor module 14 is connected to the monitoring device 8 by the lead 10 so that the sensor module 14 is in communication with the monitoring device 8.

Outputs from the force sensor 18 and the optical sensor 20 are then monitored and displayed on the display 16. Examples of outputs from the force sensor 18 and the optical sensor 20 are shown in the respective lower and upper traces of FIG. 5.

The upper trace is a photoplethysmogram (PPG) which provides an indication of the amount of light emitted by the LED 22 that is absorbed by the skin tissue at the target area (i.e. the trace is inversely proportional to the amount of light reflected by the skin tissue at the target area and received by the photodiode 24). Therefore, a relatively large amount of blood in the skin tissue, which absorbs a relatively large amount of light emitted by the LED 22, produces a relatively high output trace value, and vice versa. Of course, the trace could be inverted such that the amount of light reflected by the skin tissue is plotted in which case, a large amount of blood within the skin tissue would produce a relatively low output trace value.

The upper trace will typically have a pulsatile component and a non-pulsatile component. The pulsatile component represents light absorbed by pulsatile arterial blood whereas the non-pulsatile component represents light absorbed by non-pulsatile arterial blood, venous blood and skin tissue. The pulsatile component arises due to the change in blood volume caused by the pressure pulse of the cardiac cycle pushing blood through the blood vessels and capillaries and is therefore associated with blood flow. The pulsatile component can therefore be monitored to obtain an indication of the amount of blood perfusion in the underlying tissue.

Figure 5:
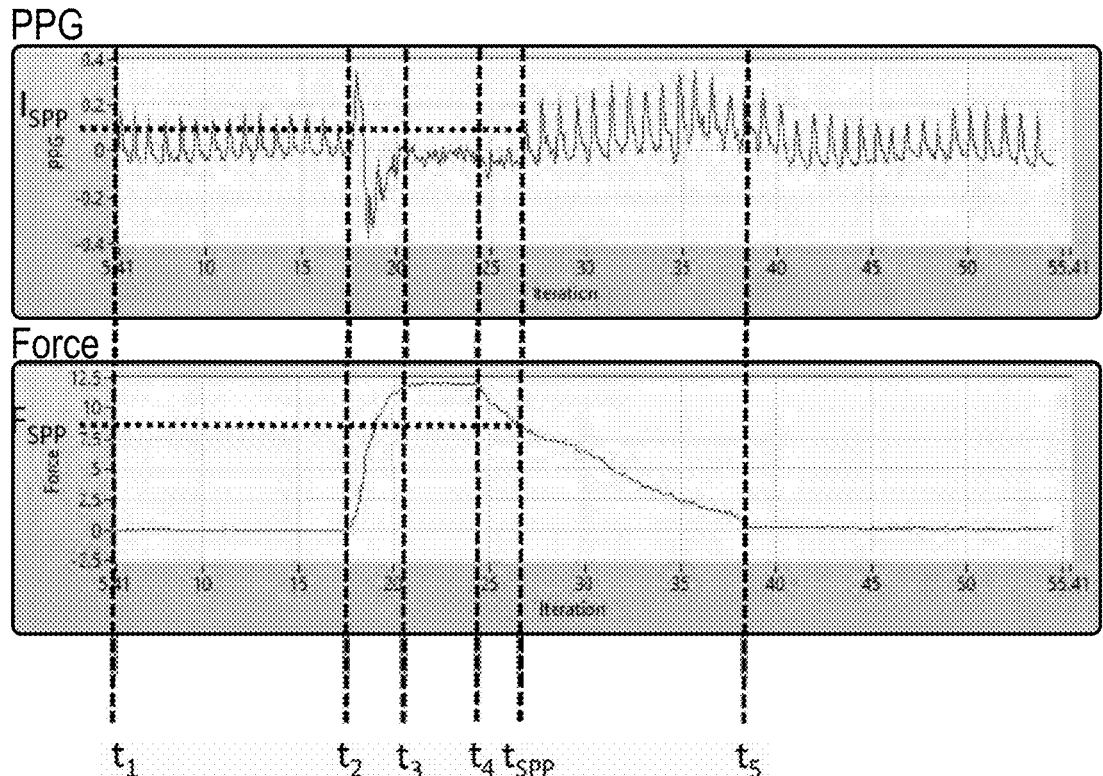
FIG. 5 is an example of a display derived from an output of the skin perfusion pressure determination device shown in FIG. 1.

The amount of light absorbed by the skin tissue initially once the skin perfusion pressure determination device 4 has been secured to the patient's arm 6 is shown between times $t_1$ and $t_2$ of the upper trace in FIG. 5. Each peak represents a pulse of arterial blood through the skin tissue at the target area.

Figure 4:
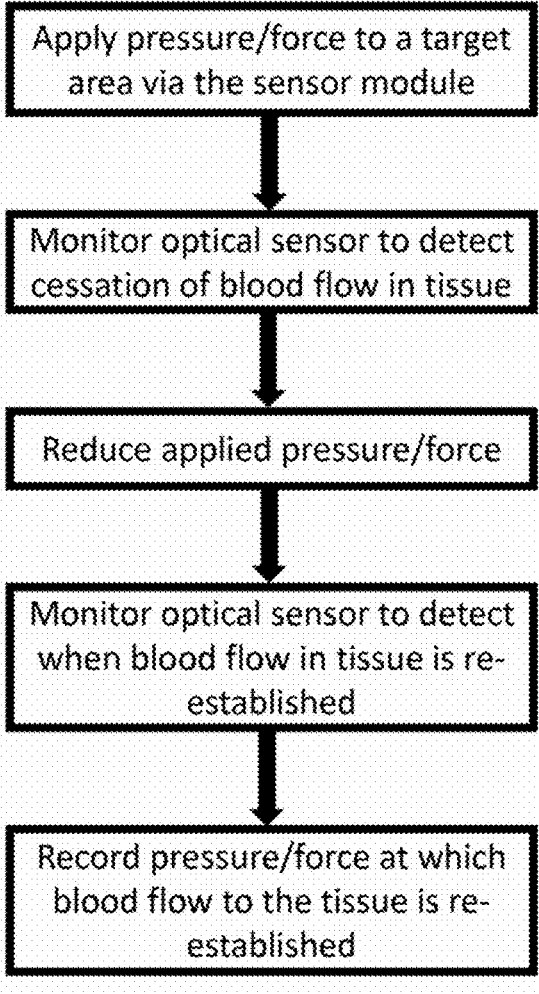
FIG. 4 is a flow chart depicting a method for determining skin perfusion pressure.

Time $t_2$ is the time at which a skin perfusion pressure measurement is commenced and corresponds to initiation of the first step of the method depicted by the flow diagram in FIG. 4.

In use, a clinician (or the patient themselves) presses the sensor module 14 against the arm 6 to occlude the blood vessels within the tissue below the target area. The amount of force is increased until the pulsatile component of the trace drops below a predetermined level or ceases to be evident, as shown at time $t_3$. Once the trace drops below the predetermined level, the clinician continues to hold the sensor module 14 against the arm 6 to ensure that the pulsatile arterial blood flow has ceased in the tissue at the target area, as shown between times $t_3$ and $t_4$. In the example shown, there remains a non-zero noise component of the trace which fluctuates at a level below the predetermined level. At time $t_4$, the clinician begins to reduce the force applied to the sensor module 14 slowly until time $t_5$ at which time the pressure module 14 has been released completely and pulsatile arterial blood flow in the tissue at the target area is completely restored.

The force exerted by the clinician on the tissue at the target area via the sensor module 14 is recorded by the lower trace. As can be seen from the lower trace, no force is recorded between times $t_1$ and $t_2$. The force increases relatively rapidly between times $t_2$ and $t_3$ as the clinician presses the sensor module 14 against the arm 6 of the patient and then plateaus while the clinician holds the sensor module 14 against the arm 6 between times $t_3$ and $t_4$. As the clinician begins to slowly release the sensor module 14 at time $t_4$, the applied force reduces steadily back to zero at time $t_5$ and pulsatile arterial blood flow returns to the skin tissue.

Pulsatile arterial blood flow returns when the blood pressure is sufficient to overcome the occlusion pressure on the blood vessels within the tissue which is applied by the clinician pressing on the sensor module 14. The return of blood flow is represented by a return of the pulsatile component in the upper trace, as shown at time $t_{SPP}$. Different criteria can be used to determine the return of pulsatile arterial blood flow. For example, return of blood flow could be determined by the return of the value of the upper trace to a predetermined threshold $I_{SPP}$ value such as a value greater than a maximum expected noise value. Alternatively, the threshold value $I_{SPP}$ may be a value that is determined based on the pulse amplitude observed before a force is applied to occlude the blood vessels (i.e. the pulse amplitude between times $t_1$ and $t_2$). In one example, a threshold value $I_{SPP}$ may be used which is a predetermined percentage of the pulse amplitude observed before a force is applied to occlude the blood vessels. Other algorithms may be used to determine return of the pulsatile component of the trace.

The magnitude of the force $F_{SPP}$ of the lower trace at time $t_{SPP}$ is then recorded. The recorded force $F_{SPP}$ can subsequently be used to determine a skin perfusion pressure. This may be done by calculation, look-up tables or based on a pre-calibration of the force sensor 18. For example, if the contact area of the portion of the sensor module 14 pressed against the skin tissue is known, the pressure applied to the skin tissue can be calculated. In this instance, the target area corresponds to the contact area of the sensor module 14. In the described embodiment, the contact area of the sensor module 14 is circular and has a diameter of 10 mm and therefore a surface area of approximately 80 mm². The larger the contact area, the greater the force required to stop blood flow. The smaller the contact area, the greater the fluctuations in pressure caused by fluctuations in the force applied so that, for very small contact areas it becomes difficult for a clinician to release the applied force in a controlled manner in order to determine the force at which blood flow returns. As described in more detail herein, the device can integrate methods for controlling the force application which can alleviate some of the difficulties described for the small contact areas. A very small contact area can also make it difficult for an accurate reading to be taken by the blood perfusion sensor. The contact area of the sensor module 14 may therefore be between 1 mm² and 1000 mm², for example between 10 mm² and 400 mm².

A benefit of the arrangement is that contemporaneous measurements of the pressure exerted by the sensor module 14 on the target area and the amount of blood perfusion are made at the target area. The measurements can be taken and recorded simultaneously to produce an accurate and reliable measurement of blood perfusion pressure at a desired location on a patient's body.

Measurement of skin perfusion pressure may be performed as a single measurement or determined from trends evident from repeated measurements over time. In some embodiments, a single measurements can be used to get the perfusion pressure or a measure for the perfusion pressure. In some embodiments, repeated measurements over time can be used and the trends can be observe to get the perfusion pressure or a measure for the perfusion pressure. Such measurements may be used to aid the prediction of wound healing.

Use of an LED light source, in particular a surface-mount LED, provides a compact, widely available, inexpensive, very reliable and a low power consumption light source. In the embodiment described above an LED which emits light in the green band of the visible spectrum is used. However, other suitable light sources could be used which emit light having a wavelength that is absorbed or reflected by blood. Light sources which emit light having a wavelength (or range of wavelengths) between 600 nm and 1350 nm may be used. In particular, light sources which emit light in the red band of the visible spectrum having a wavelength of between 600 nm and 750 nm or which emit light in the near-infrared band of the visible spectrum having a wavelength of between 850 nm and 1000 nm may be used. Light sources which emit light in the near-infrared window of biological tissue having a wavelength of between 650 nm and 1350 nm are beneficial because light has its maximum depth of penetration in tissue at these wavelengths and so a greater proportion of the emitted light will reach the blood vessels within the tissue.

Alternative light detectors may be used. For example, phototransistors or complementary metal-oxide semiconductor (CMOS) based sensors may be used. These sensors, and the photodiodes of the described embodiment, are preferred because they are inexpensive, compact and widely available.

Alternative sensors for determining a parameter associated with a pressure exerted on the target area may be used. In particular, sensors which have a thickness which corresponds to, or is less than, the thickness of a typical wound dressing may be used. Suitable capacitive, resistive thin-film or micromachined sensors or strain gauges or the like may be used. Such sensors are suitable for incorporation onto wound dressings, as described below. It will be appreciated that although the embodiment described above comprises a force sensor, alternative types of sensor which produce an output which can be used to determine a parameter associated with the pressure exerted on or stress created at the target area by a sensor module may be used. Such sensors may include sensors configured to output a pressure applied by the sensor or the sensor module to the target area.

In the embodiment described above, a simple trace showing the outputs from the sensor module 14 is provided to aid the clinician or patient. The processor may, however, be configured to display instructions to a patient/clinician on the display 16 such as instructions to increase the applied force or to reduce the applied force at each stage of the measurement process. An audible signal may be generated to inform a clinician/patient of the pulse strength. The audible signal may be continuous or a series of beeps that vary in frequency or volume depending on the magnitude of the pulsatile component of the trace. For example, an audible beep pattern may become silent when the pulsatile component drops below a threshold value and re-emerges when the pulsatile component returns indicating the return of blood flow in the tissue at the target area. In addition to written instructions, a light or a symbol or a color signal or an audible signal could be used to instruct a user to increase or decrease a force applied.

Figure 6:
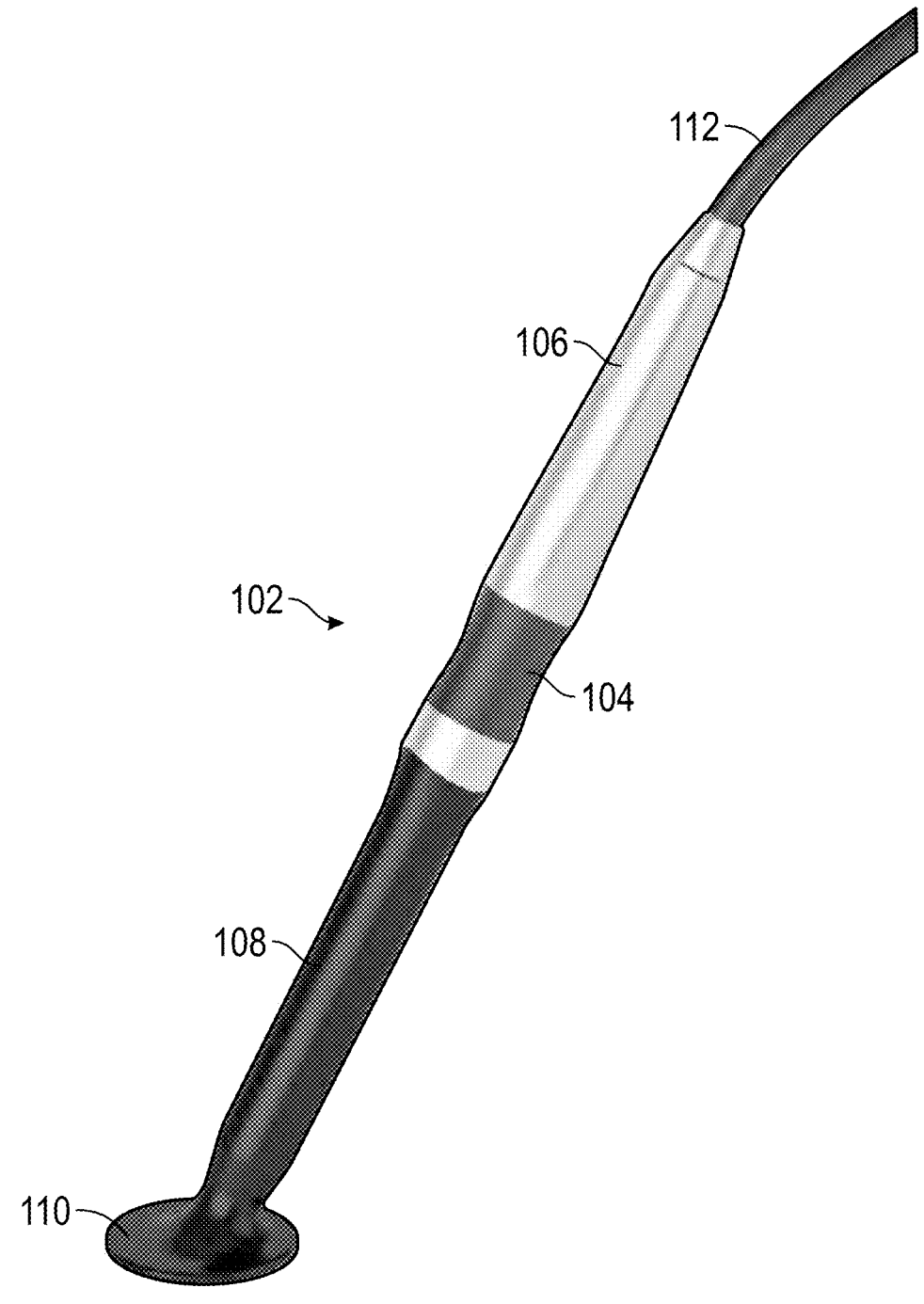
FIG. 6 shows an alternative embodiment of a skin perfusion pressure determination device comprising a probe portion.

FIG. 6 shows an example of an alternative embodiment of part of an apparatus 102 comprising a hand-held skin perfusion pressure determination device 104 comprising a grip portion 106 and a probe portion 108. The probe portion 108 has a pad portion 110 in which a sensor module (not shown) is housed. The sensor module is in accordance with the sensor module 14 shown in FIG. 2. The hand-held device 104 is connected to a monitoring device similar to that shown in FIG. 1 by a lead 112.

In use, the grip portion 106 is held by a clinician and used to press the pad portion 110 against a target area of a patient's skin. The method shown in FIG. 4 and described above is then followed to determine the skin perfusion pressure at the target area.

As described herein, a skin perfusion pressure determination device can be used to measure a blood perfusion or blood perfusion pressure at a target tissue area. In order to assess the health or healing of a wound or tissue area, the skin perfusion pressure determination device may be used to measure a parameter associated with wound healing at various target tissue areas. In some embodiments, the various target tissue area can be various points about the perimeter of the wound dressing. For example, the skin perfusion pressure determination device can provide a measurement of the amount of blood perfusion in the tissue surrounding the wound. In other embodiments, the target tissue area can be healthy tissue or tissue not associated with a wound. In some embodiments, the skin perfusion pressure determination device can be used in combination with other sensor enabled devices. For example, the skin perfusion pressure determination device can be used in combination with or in coordination with a sensor enabled wound dressing or wound contact layer as described in more detail in International Application No. PCT/IB2017/000693, filed May 12, 2017, published as WO 2017/195038 on Nov. 16, 2017, titled "SENSOR ENABLED WOUND MONITORING AND THERAPY APPARATUS," the disclosure of which is hereby incorporated by reference herein in its entirety. In some embodiments, the skin perfusion pressure determination device can be incorporated into various medical devices or apparatuses as described in more detail in International Application No. PCT/EP2018/055940, filed Mar. 9, 2018, titled "DEVICE, APPARATUS AND METHOD OF DETERMINING SKIN PERFUSION PRESSURE," the disclosure of which is hereby incorporated by reference herein in its entirety.

Figure 7B:
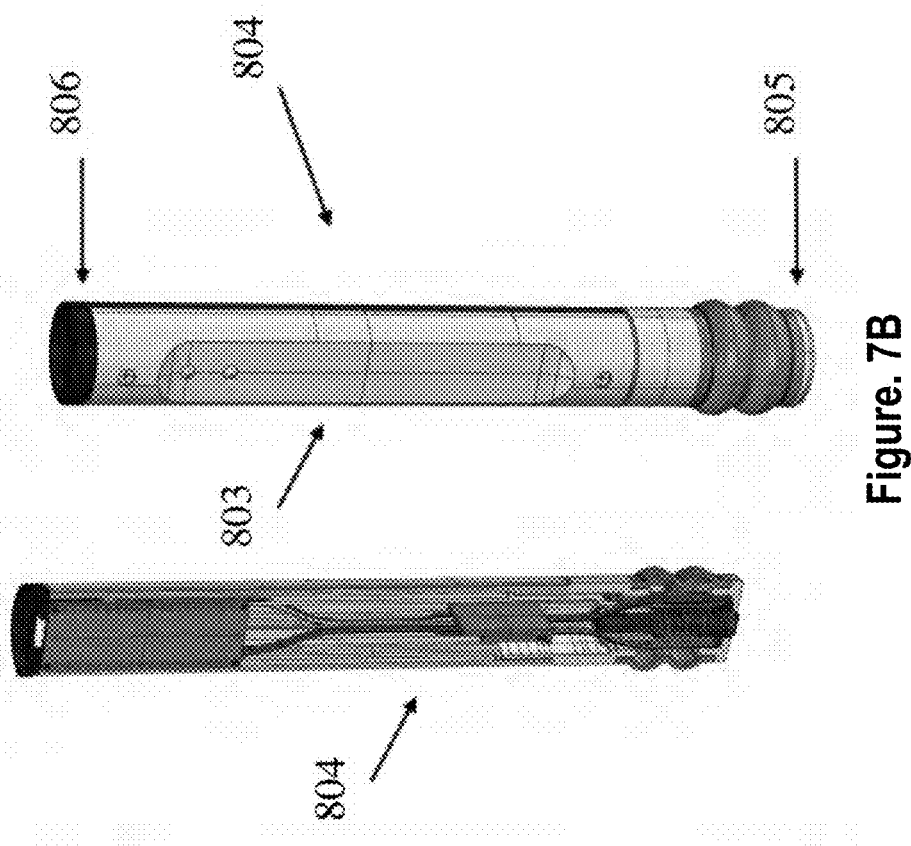
FIG. 7A-7B illustrate an embodiment of a skin perfusion pressure determination device.
Figure 7A:
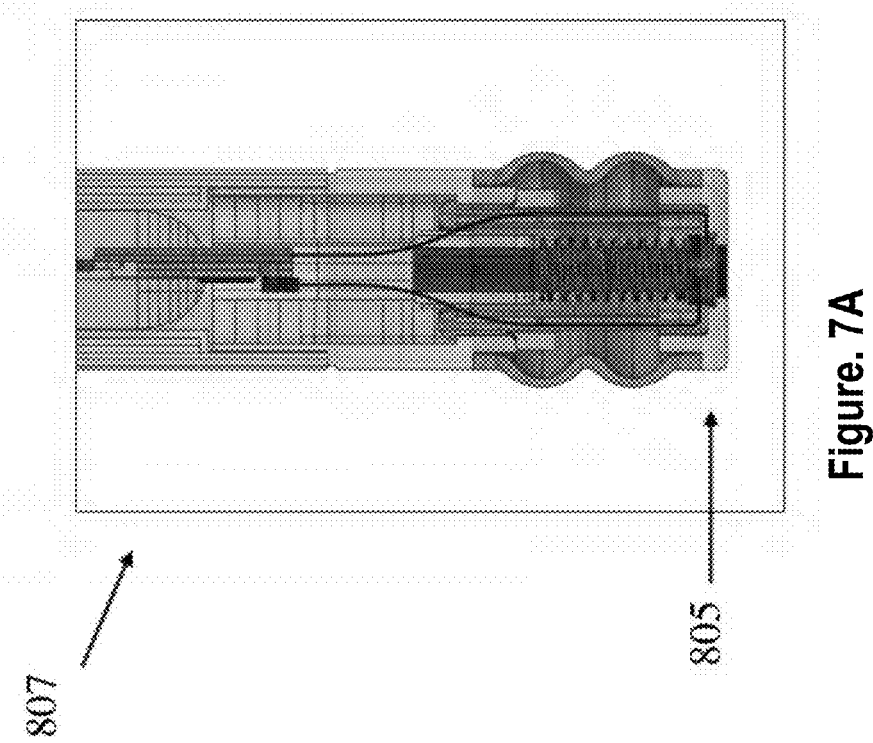

FIGS. 7A-8-B illustrate further embodiments of a skin perfusion pressure determination device. FIG. 7A illustrates an embodiment of a skin perfusion pressure determination device 804 with a cross sectional view that shows the interior components of the device. The skin perfusion pressure determination device 804 has a proximal end 805 and a distal end 806 and comprises an elongate housing 803. The elongate housing 803 may be made of a single part or multiple parts, which forms or form an elongate body having a proximal end and a distal end. The elongate housing is configured to be hand-held, and in some embodiments has the shape of a pen. A proximal end assembly 807, shown in the enlarged cross-sectional view of FIG. 7B, is provided at the proximal end of the elongate housing. The proximal end assembly 807 has a proximal end that defines the proximal end 805 of the device 804 and can be used to contact a target tissue area or skin to obtain a skin perfusion pressure determination. Although the proximal end assembly 807 in this and other embodiments is described as being connected to or attached to the proximal end of the elongate housing 803, it will be appreciated that components of the proximal end assembly 807 may form part of the elongate housing itself, such that the elongate housing extends to the proximal end 805.

The skin perfusion pressure determination device 804 can incorporate a sensor module for obtaining a skin perfusion pressure measurement, as further described herein. The sensor module may be positioned within or on the skin perfusion pressure determination device 804. In some embodiments, the sensor module can be associated with and in optical communication with the proximal end 805 of the skin perfusion pressure determination device 804 to obtain a skin perfusion pressure measurement. In some embodiments, the sensor module can be provided on the proximal end 805 and/or incorporated into the proximal end 805 of the skin perfusion pressure determination device 804.

Figures 8A, 8B:
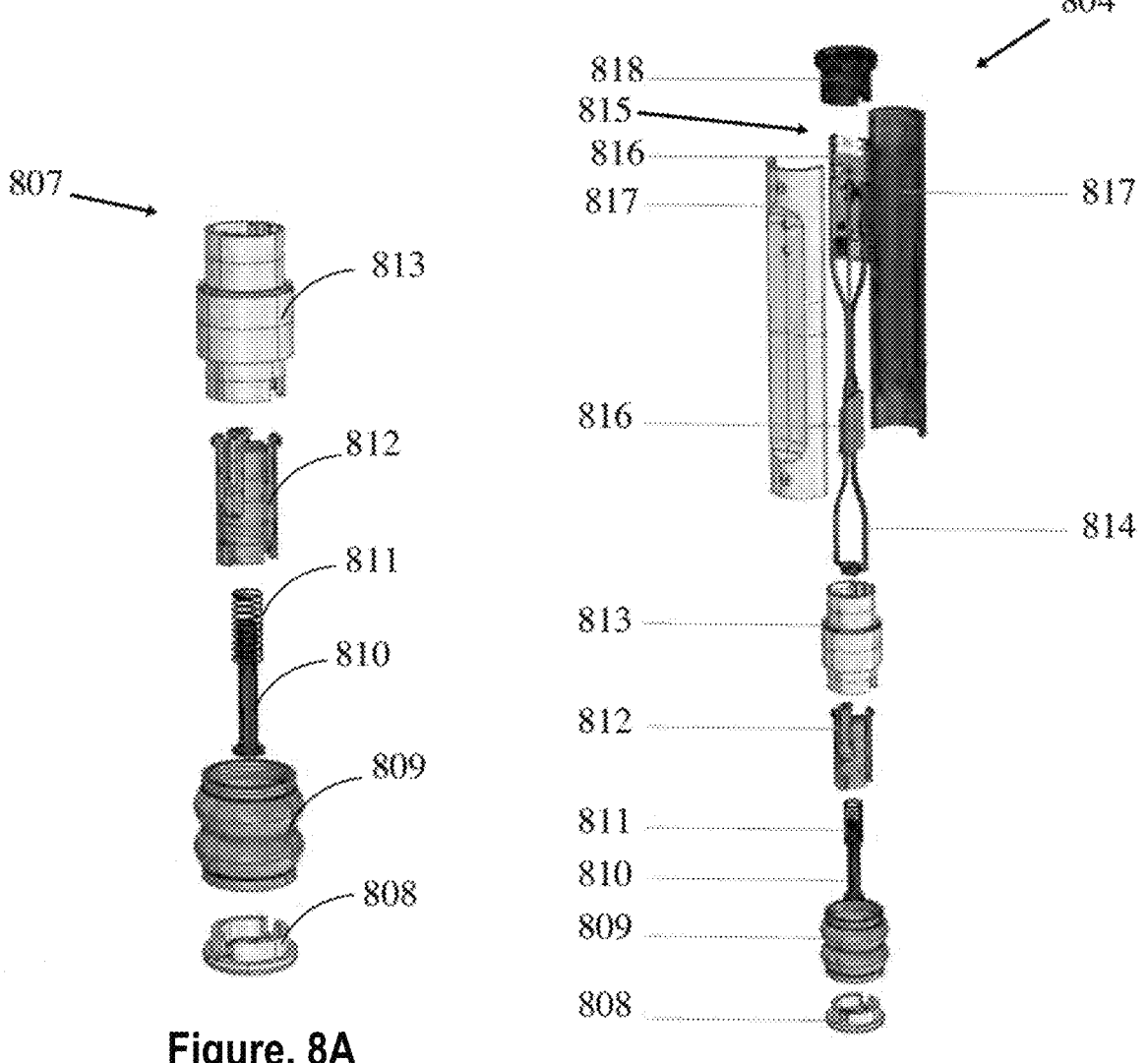
FIG. 8A-8B illustrate an exploded view of an embodiment of a skin perfusion pressure determination device.

FIGS. 8A and 8B illustrate an exploded view of the skin perfusion pressure determination device 804. The skin perfusion pressure determination device 804 can be mechanically or manually actuated. FIG. 8A illustrates an embodiment of the proximal end assembly 807. The proximal end assembly 807 includes a proximal end cap 808 enclosing the proximal end 805 of the skin perfusion pressure determination device and a sensor module for obtaining a skin perfusion pressure measurement as described herein. In some embodiments, the proximal end 805 of the skin perfusion pressure determination device 804 can include the sensor module as described herein.

The proximal end assembly 807 further comprises bellows 809, a plunger 810, a spring 811, and a slider 812 that can move within the device 804 to allow contraction and extension of the proximal end assembly 807. The proximal end cap 808 and bellows 809 can be coupled to an end cap 813 to enclose the plunger 810, spring 811, and slider 812 within. The end cap 813 may be joined to the proximal end of the housing 803.

When assembled, the plunger 810 and spring 811 can be positioned within the slider 812 (shown in FIG. 8B). When the proximal end of the skin perfusion pressure determination device 804 is applied to a surface or target tissue area (e.g. the skin of a patient or surface of a wound), a force is applied to the grip portion of the skin perfusion pressure determination device 804 by the hand of the user or other source. By applying a force to the grip portion, the user moves the grip portion towards the skin. This compresses the spring which exerts a force onto the plunger and therefore onto the skin. As part of the relative movement of the grip portion and the proximal end assembly, the bellows changes shape. Once blood flow has been occluded, the force can be released at a controlled rate allowing the proximal end assembly to expand at a controlled rate until the force has been completely removed and the proximal end assembly has returned to a resting (i.e. expanded) state. In other embodiments, the force can be completely removed causing the proximal end assembly to expand to a resting (i.e. expanded) state.

In some embodiments, the spring 811 can be used to control the force applied to and/or withdrawn from the target area. In some embodiments, the bellows can shield the user from the decreasing space between the proximal end cap and the main body or housing of the devices. For example, the bellows prevent the device from pinching the skin or a finger as the proximal end assembly and/or the spring mechanism is compressed. Additionally, the bellows can assist in preventing ingress of foreign material and provide a hygienic material with a smooth surface finish that can be readily cleaned. In some embodiments, the bellows can contribute to the force required by the user to push the sensor down onto the target area. In some embodiments, the bellows can be polymeric bellows.

In some embodiments, the proximal end cap 808 can include or be in communication with one or more sensors or sensor module to obtain a skin perfusion pressure measurement as described herein. For example, an optical sensor can be provided in the proximal end assembly and can be in communication with the proximal end cap 808 which is configured to be in contact with the target tissue area or skin surface. As described herein, the sensor module can refer to one or more sensor assemblies and/or one or more sensors used to determine a skin perfusion pressure measurement, including, but not limited to the components described with reference to FIG. 2. In some embodiments, the one or more sensor assemblies and/or one or more sensors can be positioned within the skin perfusion pressure determination device 804. For example, the one or more sensor assemblies and/or one or more sensors can be positioned within the housing 803 and/or within the proximal end assembly 807. In some embodiments, the one or more sensor assemblies and/or one or more sensors can be incorporated into or provided with proximal end cap 808.

To obtain the skin perfusion pressure measurement, the proximal end cap 808 can provide a surface area that will allow for the target area to be blanched or occluded as well as allow for a sensor (i.e. located as a component in the center) to monitor the blood flow synchronously with the application of the pressure over the surface area. The surface area of the proximal end cap 808 can be large enough to distribute the pressure applied to the target tissue area and thereby reduce pain or discomfort to the patient while allowing the target area to be blanched. If the surface area contacting the skin is too small, it can cause pain or discomfort to the patient when pressed against the target area and the small surface area may not form an area of blanched skin. A thumbprint sized area can be suitable for applying pressure and blanching the skin while allowing for appropriate blood flow monitoring. For example, the proximal end cap 808 or the proximal end 805 can be greater than about 30 mm, about 30 mm to about 20 mm, about 20 mm to about 10 mm, about 10 mm to about 5 mm, or less than about 5 mm. In some embodiments, the proximal end cap 808 or the proximal end of the skin perfusion pressure determination device that contacts the target area can be flat or substantially flat so that the proximal end cap 808 or the proximal end is stabilized on and rests flat on the target tissue area. This can aid in ensuring that readings are taken such that the axial orientation of the skin perfusion pressure determination device is perpendicular to the plane of the target area.

In some embodiments, the proximal end of the skin perfusion pressure determination device can be domed to ensure even pressure distribution and contact with skin. In some embodiments, the domed surface can be shallow providing slight curvature from the sides of the proximal end. In some embodiments, the proximal end or proximal end cap can be domed, curved, and polyhedron surface. The domed surface can allow even pressure distribution and contact with the target area and ensure that readings are taken such that the axial orientation of the skin perfusion pressure determination device is perpendicular to the plane of the target area.

In some embodiments, a flanged end similar to the pad portion 110 in FIG. 6 can be used to provide an increased surface area that is greater than the cross-sectional area of the skin perfusion pressure determination device 804. The flanged end can contact the target tissue area and provide the necessary surface area that will allow for the target area to be blanched or occluded as well as allow for a sensor (i.e. located as a component in the center) to monitor the blood flow synchronously with the application of pressure over the surface area. In some embodiments, the proximal end of the skin perfusion pressure determination device can provide a larger surface area to contact the skin by some other means extended outwards in the plane of the skin to stabilize the device on the target area and rest the device flat on the target area. In some embodiments, the proximal end of the skin perfusion pressure determination device can be domed to ensure even pressure distribution and contact with the target area. In some embodiments, a domed surface (for the purpose of even pressure distribution over the target area where the sensor is located) can be used with an in-plane flange to provide stabilization of the sensor head in the plane of the target area.

Figure 8C:
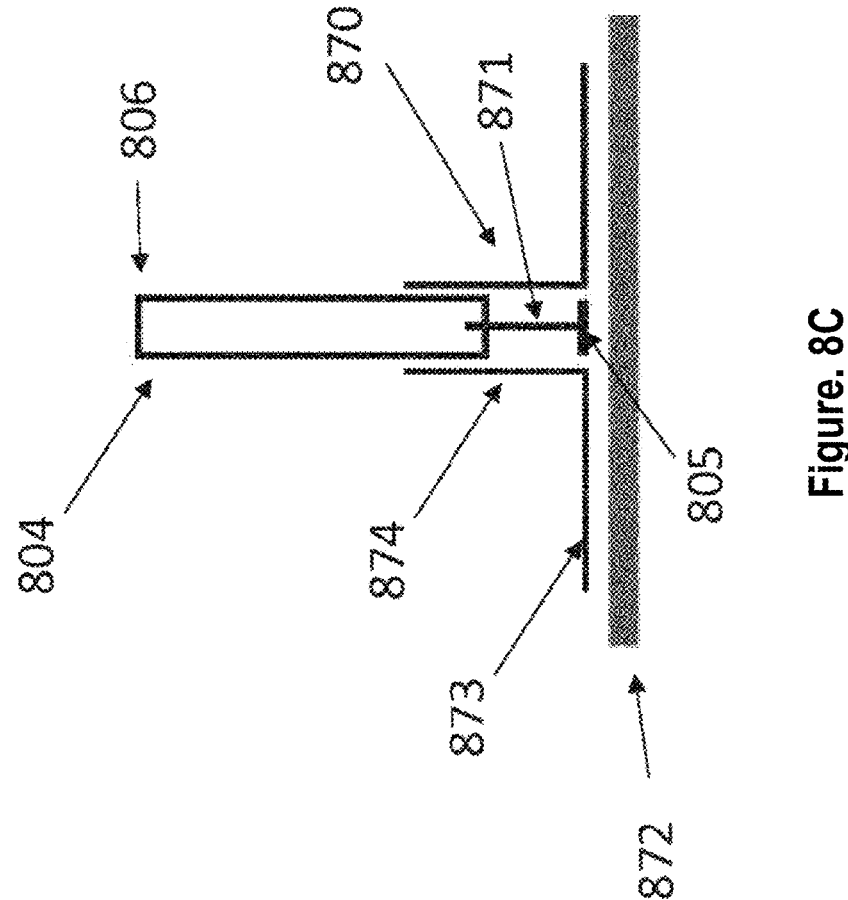
FIG. 8C illustrates an embodiment of the skin perfusion pressure determination device with a flanged portion on a proximal end.

FIG. 8C illustrates an embodiment of the skin perfusion pressure determination device with a proximal end 805 and distal end 806. A flange 870 can be used to stabilize and position the skin perfusion pressure determination device on the target area in the proper orientation for obtaining a reading. In some embodiments, the flange 870 can be used to position the spring mechanism 871 (or proximal end assembly including the spring mechanism) running axially up the perfusion pen 804 at a 90-degree angle to the surface of the target area 872. As illustrated in FIG. 8C, the flange can be positioned around the proximal end 805 of the skin perfusion pressure determination device. Although the flange 870 illustrated in FIG. 8C is large in proportion to the skin perfusion pressure determination device 804, a range of sizes or shapes can be used. FIG. 8C illustrates a cross sectional view through the flange as a disc 873 at the target area interface 872 and a tube 874 which the skin perfusion pressure determination device 804 can run through. As illustrated in FIG. 8C, the skin perfusion pressure determination device 804 with the sensor module can be positioned axially through the tube 874 of the flange 870 at a 90 degree angle to the plane of the surface of the target area 872.

In some embodiments, the proximal end cap can be transparent or open. In some embodiments, if the proximal end cap is open, then a surface area can be provided that allows the target area to be blanched or occluded. In some embodiments, the surface area of the optical sensor or sensor module can allow for the target area to be blanched or occluded and the optical sensor or sensor module can be in direct contact with the skin. In such embodiments, the proximal end cap can be open or can be optional. In some embodiments, the proximal end cap is an optional feature of the proximal end assembly. If the proximal end cap is not used, the sensor module and/or the proximal end of the proximal end assembly can be in contact with the target area and can provide a surface area sufficient to allow for the target area to be blanched or occluded as well as allow for a sensor (i.e. located as a component in the center) to monitor the blood flow synchronously with the application of the pressure over the surface area. In some embodiments, the sensor and/or sensor module may be positioned in the center of the proximal end of the device. In some embodiments, the sensor and/or sensor module may be positioned off-center or in any portion at the proximal end of the device.

In some embodiments, the proximal end cap 808 can be formed from glass materials, for example, high strength glass materials such as corning or gorilla glass. The material of the proximal end cap 808 can be any material that allows for an optically clear, biocompatible and scratch resistant contact design option for the optical sensor. The scratch resistant contact surface of the proximal end cap 808 and/or the proximal end can maintain an optical pathway over repeated use of the device. The glass can be made into the various shapes described for the target area contacting end or proximal end of the device. The glass material can also allow for cleaning and sterilization of the device for re-use to reduce waste and consumables.

In some embodiments, the proximal end cap can be used to apply a force on the skin and to carry out the optical measurements. FIGS. 8M-8P illustrate embodiments of a portions of a proximal end assembly with force sensor 876 and optical sensor 877 incorporated into the device. In some embodiments, an optical sensor 877 can be used to provide the optical measurements as described herein. As used herein, the optical sensor 877 can be incorporated into or can be the sensor module within or in communication with the proximal end cap and the proximal end.

Figure 8D:
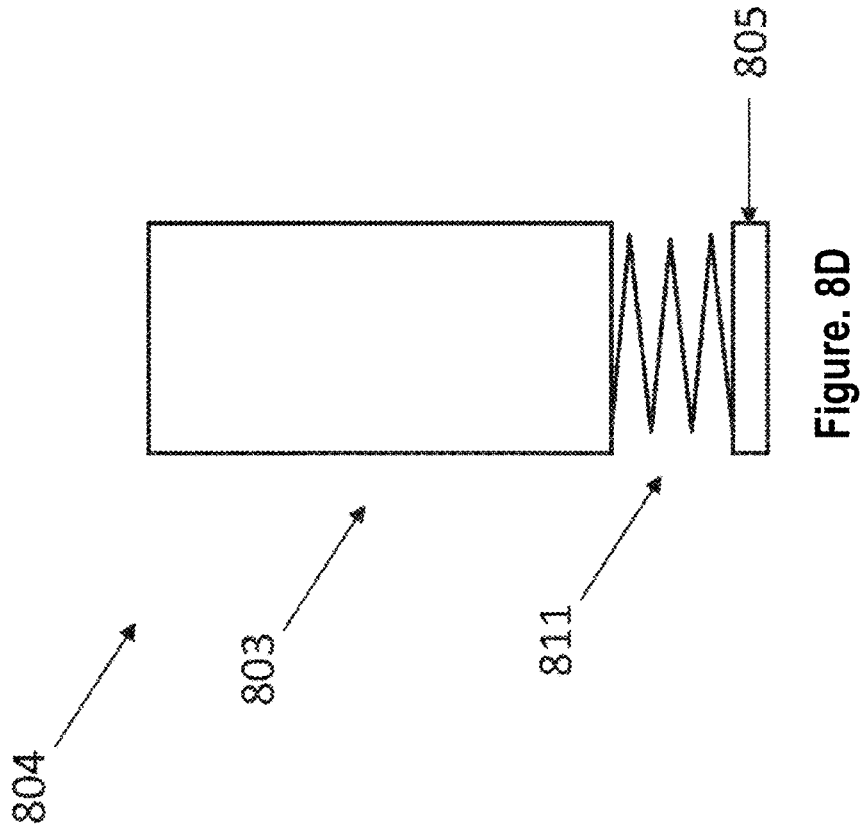
FIGS. 8D-8L illustrates embodiments of a skin perfusion pressure determination device with various spring and/or bellows configurations.
Figure 8E:
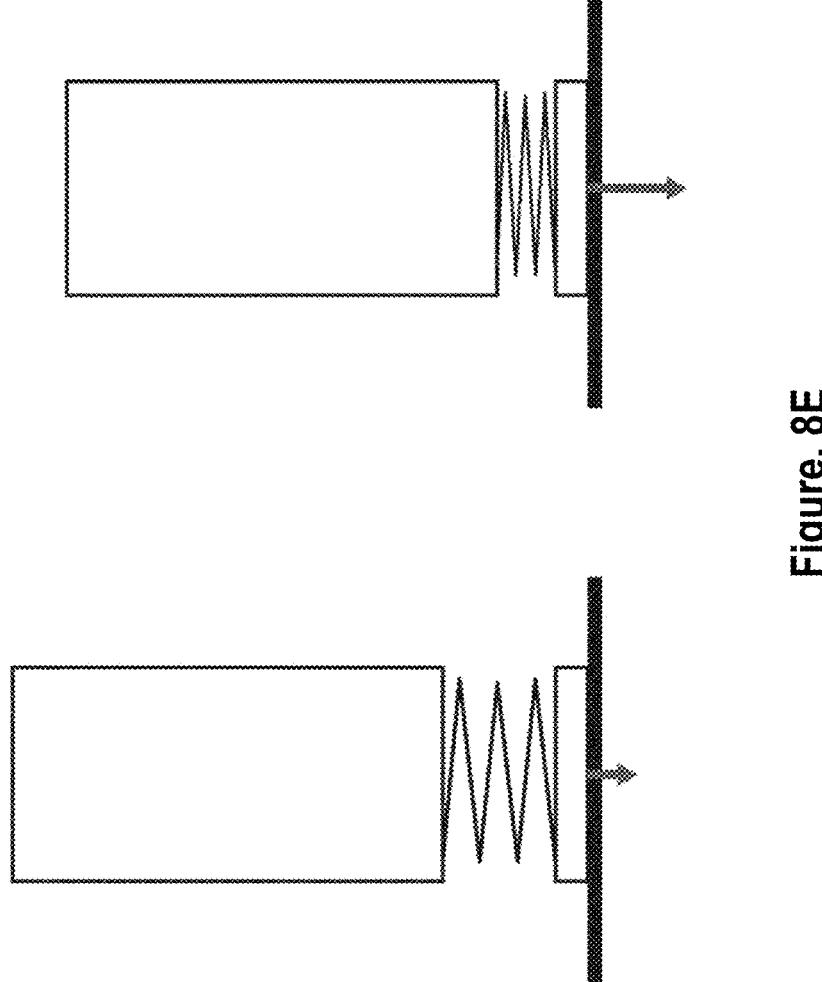
Figures 8F, 8G, 8H, 8I, 8J:
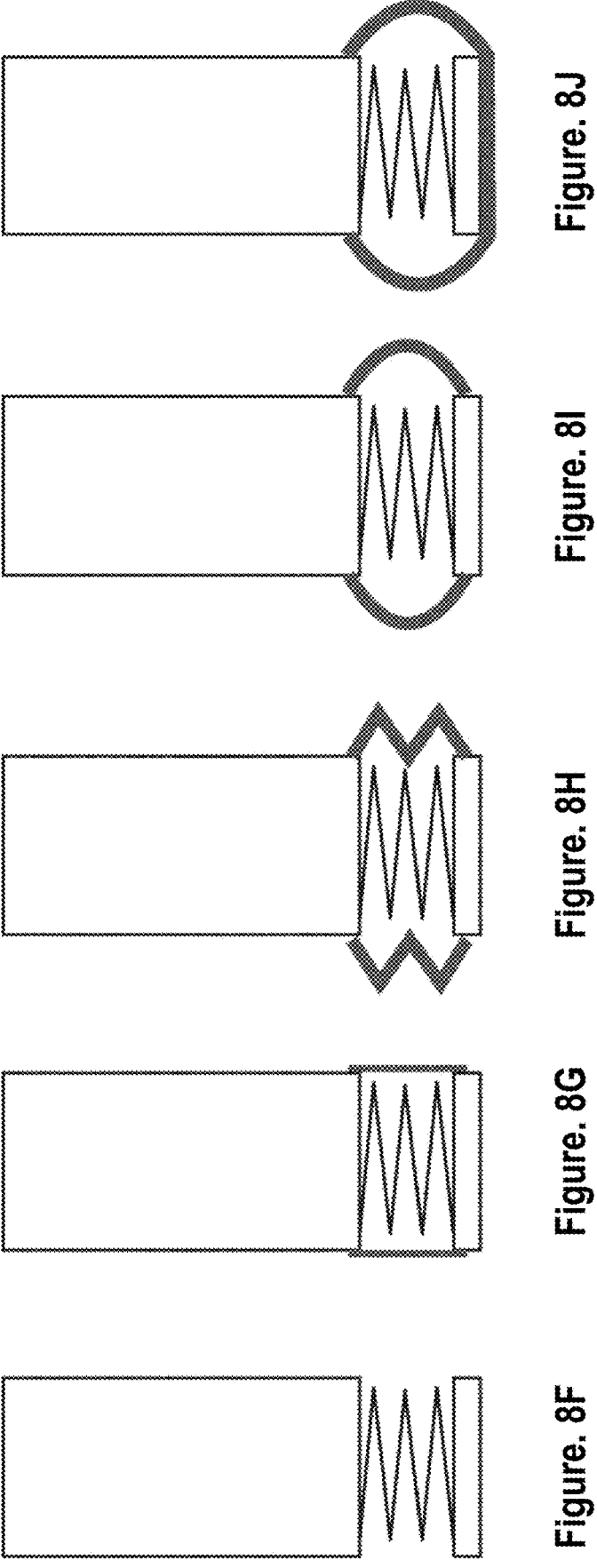
Figure 8L:
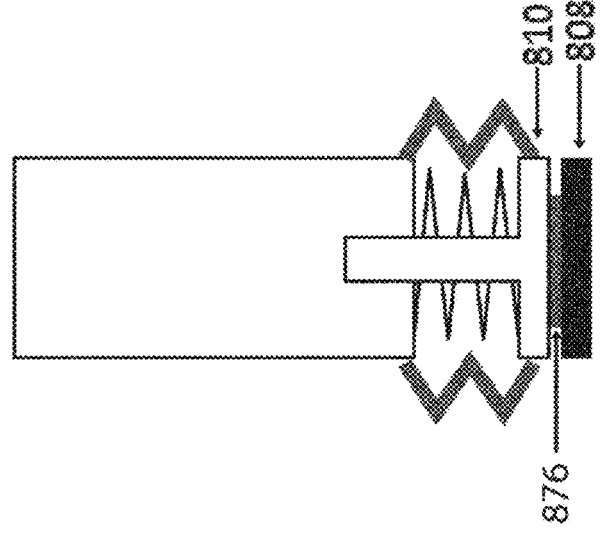
Figure 8K:
Figure 8K:
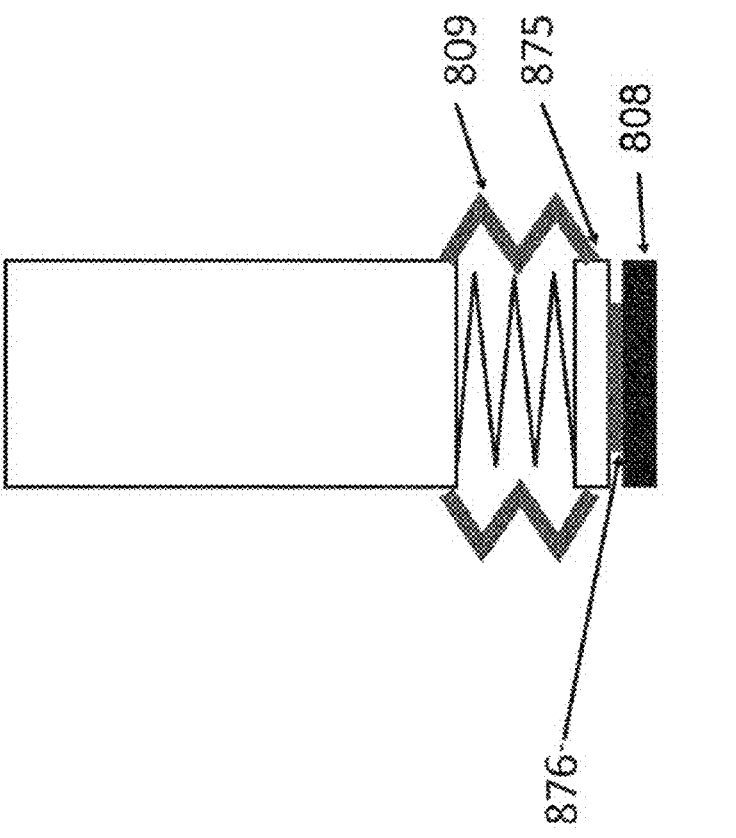
Figure 8M:
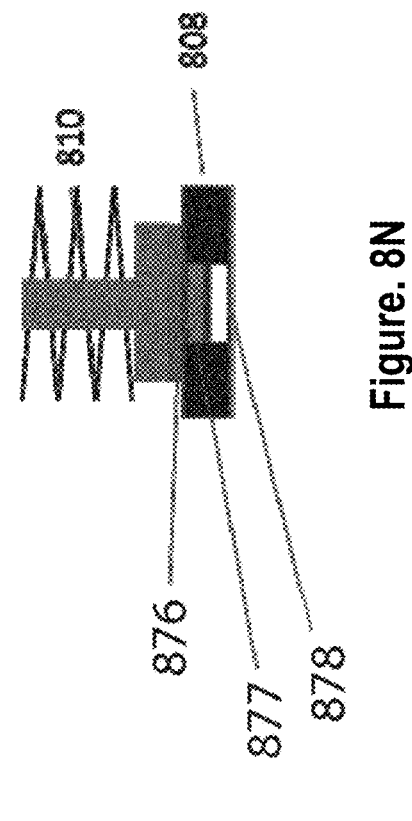
FIGS. 8M-8P illustrate embodiments of portions of a proximal end assembly with sensors incorporated into the skin perfusion pressure determination device.

In some embodiments, the optical sensor 877 can work over small ranges. The optical sensor 877 can be located in or on the proximal side of the proximal end cap 808 as illustrated in FIG. 8M. In some embodiments, the optical sensors 877 can shine red and infra-red light on the target tissue area and monitor the response. In some cases, the optical sensor 877 can have its own window that allows light to pass through.

Figure 8N:
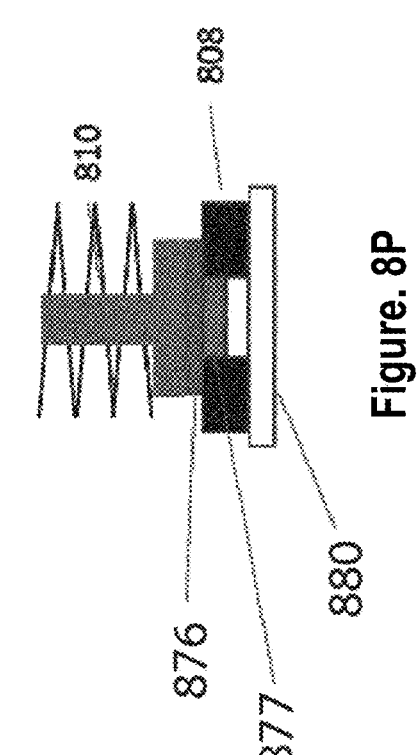

In some embodiments, as illustrated in FIG. 8N, the optical sensor and proximal end cap 808 can have an open proximal end or can utilize a transparent window 878 on the proximal side to allow optical communication with the target tissue area. When an open proximal side is used, then an optically transparent window can be provided in the region of the sensor within the proximal end cap 808 in order to protect the sensor and the sensor electronics and also to provide a skin-compatible interface as illustrated in FIG. 8N. In some embodiments, the sensor can be manufactured with a transparent window and the sensor with the integrated transparent window can be located in a recess in the proximal end cap 808. In some embodiments, if the integrated transparent window is biocompatible and deemed to be acceptable for skin or tissue contact, the sensor can sit flush with the proximal end of the proximal end cap 808 and be part of the target area interface of the device. In such embodiments, a separate transparent window is not needed in the proximal end cap 808. In some embodiments, a separate transparent window can be used with the proximal end cap 808 whether or not the optical sensor 877 has an integrated transparent window. In some embodiments the separate transparent window can be beneficial, for example for cleaning or skin-compatibility.

Figure 8O:
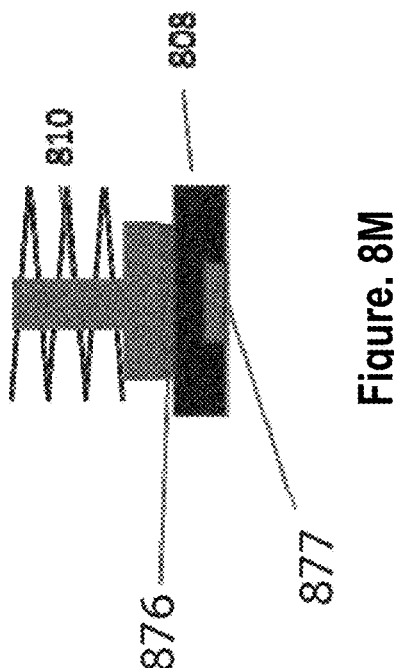
Figure 8P:
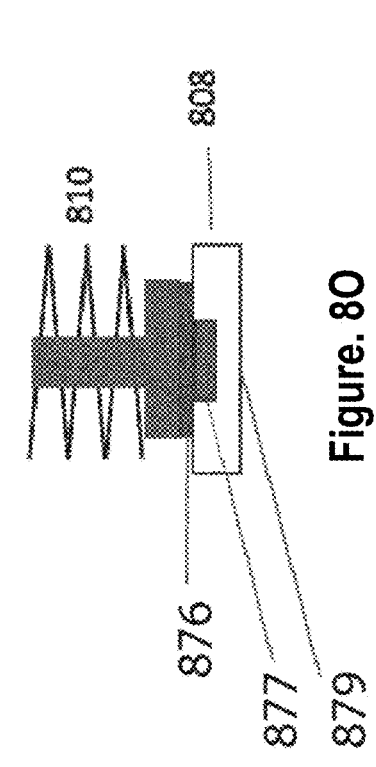

In some embodiments, the whole proximal end cap 808 could be made from a transparent material 879 as illustrated in FIG. 8O. FIG. 8P illustrates the use of a disposable skin-interfacing part 880 such as a disposable cover as described in more detail herein. The disposable skin-interfacing part 880 can be positioned at the proximal end of the skin perfusion pressure determination device on a proximal side of the proximal end cap 808. The disposable skin-interfacing part 880 could serve as the transparent window as well as providing a disposable cover. As illustrated in FIG. 8P, when the disposable skin-interfacing part 880 is used the optical sensor 877 can be housed in the proximal end cap 808 in a recess or hole. In some embodiments, the additional disposable component can then provide a transparent cover.

In some embodiments, as described herein, in addition to allowing for an optical measurement, the proximal end cap can also be used to apply the force to the target tissue area. As described herein, the proximal end of the proximal end cap 808 can be shaped to provide a more uniform application of the skin pressure, for example, it can be domed rather than be flat. In some embodiments, the material of the proximal end of the proximal end cap can be compliant so that the proximal end can deform as the pressure is applied. In some embodiments, the proximal end cap can be formed from any plastics and/or metals. In some embodiments, the material of the proximal end cap can be a composite or complex structure.

In some embodiments, the proximal end cap 808 can be useful for protecting the sensors, routing the connections to the force sensor and optical sensors, and can allow for cleanability of the device. In some embodiments, the proximal end cap 808 is optional. The proximal portion of the plunger 810 can be designed to fulfil many of the functions of the proximal end cap 808.

Figures 8Q, 8R, 8S, 8T:
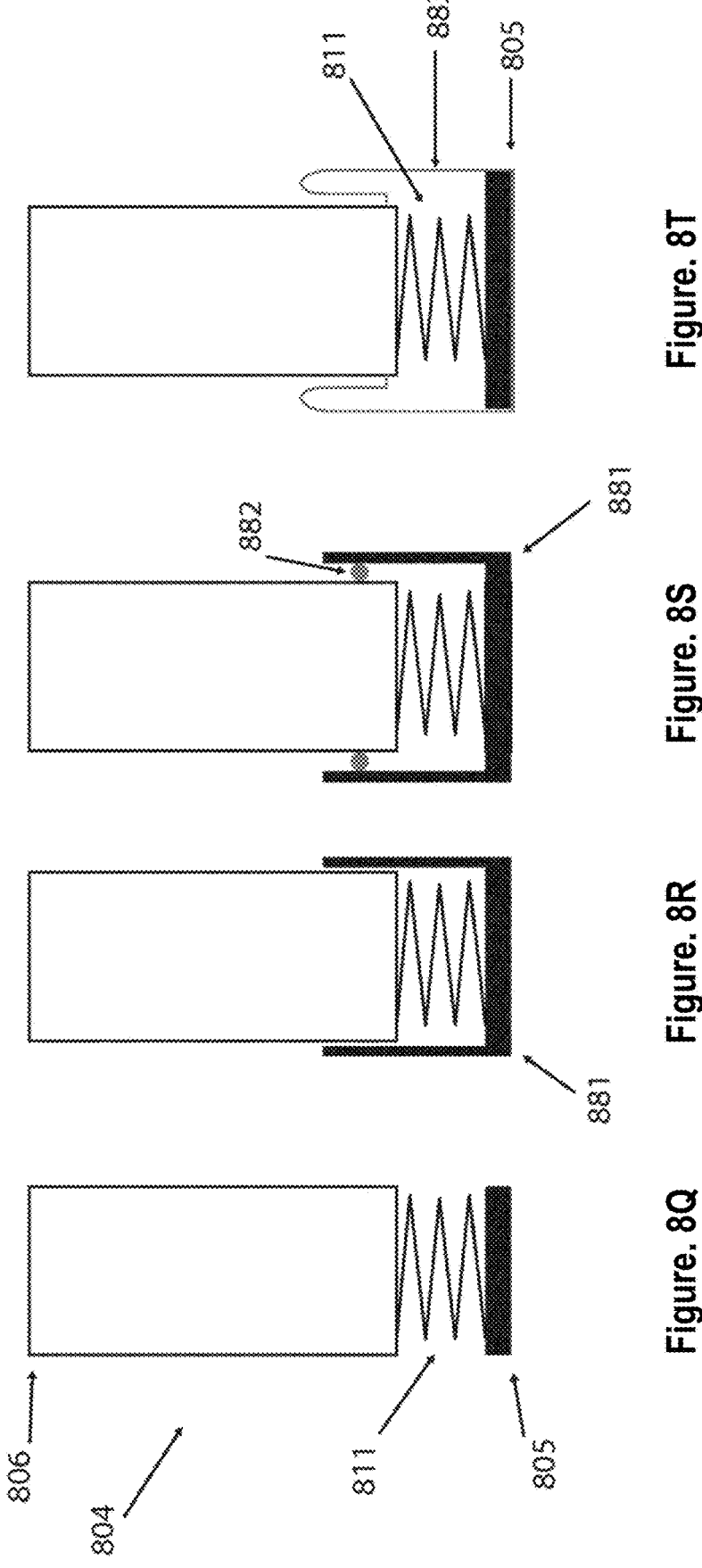
FIGS. 8Q-8T illustrates embodiments of a skin perfusion pressure determination device with various spring and/or bellows configurations.

FIGS. 8Q-8T illustrate embodiments of the skin perfusion pressure determination device 804 with various embodiments of the proximal end assembly components. In some embodiments, as described herein the proximal end 805 of the skin perfusion pressure determination device 804 can be connected to the distal portion of the skin perfusion pressure determination device 804 by a spring 811. In some embodiments, as illustrated in FIG. 8Q, the space between the proximal end 805 and the distal portion of the device can be open and the spring 811 would be accessible. In some embodiments, as illustrated in FIG. 8R, the proximal end cap 881 can have distally extending arms that overlap the sides of the portion of the skin perfusion pressure determination device 804 connected to the distal end of the spring 811. The overlapping proximal end cap 881 to create a telescopic-type of arrangement and the portion of the skin perfusion pressure determination device 804 connected to the distal end of the spring 811 can move distally to proximally or proximally to distally within the extended arms of the overlapping proximal end cap 881. In some embodiments, as illustrated in FIG. 8S, the overlapping proximal end cap 881 can have a sliding seal 882 between the two parts. Although in FIGS. 8R and 8S the portion of the skin perfusion pressure determination device 804 connected to the distal end of the spring 811 is shown inside of the arms of the overlapping proximal end cap 881, in some embodiments, the overlapping proximal end cap 881 can be positioned inside the walls of the portion of the skin perfusion pressure determination device 804 connected to the distal end of the spring 811. In some embodiments, a rolling diaphragm structure 883 can be used between the proximal end 805 and the portion of the skin perfusion pressure determination device 804 connected to the distal end of the spring 811 as shown in FIG. 8T.

FIG. 8B illustrates an exploded view of the skin perfusion pressure determination device 804. Distal to the proximal end assembly 807 the skin perfusion pressure determination device 804 includes a sensor assembly 814 and a control unit 815. In some embodiments, the control unit 815 can comprise one or more printed circuit boards (PCBs) 816. In some embodiments, the sensor assembly 814 can be a force sensor. The sensor assembly 814 and a control unit 815 can be surrounded by a casing 817 which forms part of the elongate housing. In some embodiments, the casing can be formed from one or more casing portions coupled together to form the casing or elongate housing and surround the electronic components including but not limited to the sensor assembly 814 and the control unit 815. For example, the casing 817 can be formed from two casing portions coupled together as illustrated in FIG. 8B. In other embodiments, the casing can be formed as a single integrated casing. The end cap 813, casing 817, and a distal end cap 818 can be coupled to enclose the sensor assembly 814 and control unit 815.

As described herein, as part of the operation of the skin perfusion pressure determination device 804, the user can apply a force to the skin of the patient using the skin perfusion pressure determination device 804 in order to reduce and temporarily stop the blood flow in the skin. Then the user can release this force slowly until blood flow is re-established. The user can apply this force directly as in some of the examples described herein. However, if, for example, the user applies this force directly by hand, then any small motion of the hand can lead to a significant change of force. Also, any jittering of the hand could also lead to a change in the force. In order to allow the user to have better control over the force applied, some compliance can be added to the skin perfusion pressure determination device. For example, as illustrated in FIG. 8D, the spring 811 can provided this compliance. The spring 811 can link the distal end of the housing 803 of the skin perfusion pressure determination device 804 which the user grips with the proximal part (including the proximal end 805) which applies the force to the proximal end of the skin perfusion pressure determination device. The proximal end 805 then in turn applies the force to the target area.

In some embodiments, the spring will generate a force on the target area as it is compressed. It can require a certain displacement to generate a certain force. With this spring in the path, the user will need to move the grip portion of the skin perfusion pressure determination device by a certain distance towards the target area, thereby compressing the spring 811 which in turn then applies a certain force to the target area. The softer the spring, the larger the displacement needs to be to generate a certain force on the target area. This compliance in the system can make it easier for the user to apply and release the force in a more controllable manner. In addition, small relative motions of the user's hand relative to the target area can have a smaller effect. FIG. 8E illustrates embodiments of a skin perfusion pressure determination device with different spring types. As illustrated in FIG. 8E, a softer spring can generate a smaller amount of force applied to the target area (illustrated with the device on the left side of FIG. 8E) and a tighter spring can cause a larger force to be applied to the skin (illustrated with the device on the right side of FIG. 8E). In some cases, when a small force is applied to the skin or target area, the spring can be compressed less (illustrated with the device on the left side of FIG. 8E) than if a larger amount of force is applied to the skin or target area (illustrated with the device on the right side of FIG. 8E).

As described herein, a number of different grip options can be used for the skin perfusion pressure determination device. Depending on the grip options, the user can apply and control the force applied to the skin perfusion pressure determination device in a different way. In addition, the spring can provide a mechanism for making the force control easier. Both the different grip options and the different spring options can help in giving the user better control of the force application.

In some embodiments, for the spring to control the force applied to the skin, the distal end of the housing of the skin perfusion pressure determination device and the proximal end need to be able to move relative to each other. In addition, the skin perfusion pressure determination device is used to measure the force applied to the skin, and therefore, the additional components in the system which links the distal end of the housing and the proximal end of the skin perfusion pressure determination device should be limited to avoid the additional components providing or taking up a significant amount for force. Additionally, the distal end of the housing and the proximal end can stay in alignment and move linearly relative to each other. This can require some guidance system, for example, the plunger 810 and slider 812.

Various mechanisms can be used to allow the distal end of the housing and the proximal end to move relative to each other. For example, FIGS. 8F-8J provides various options. In some embodiments, an open gap as shown in FIG. 8F. As illustrated in FIG. 8F, the proximal end 805 and distal end of the housing 803 can have an open gap in between them (i.e. a design without the bellows 809). However, there would then be an opening in the skin perfusion pressure determination device which exposes the interior of the skin perfusion pressure determination device to the outside world. Dirt and fluids could get inside and damage the electronics and/or the interior of the skin perfusion pressure determination device. Moreover, if the skin perfusion pressure determination device is intended to be reusable, the ability to clean the skin perfusion pressure determination device can be useful. With the open gap, this can be difficult to achieve.

In some embodiments, various features can be used to cover the space or break in the distal end of the housing created by positioning the spring between the distal end of the housing and proximal end. Covering the space can have a number of advantages, including, but not limited to, it is more aesthetically pleasing, provides a continuous outer shape of the skin perfusion pressure determination device, protects the interior components of the skin perfusion pressure determination device, and provides a cleaner interface and makes the device cleanable. In some embodiments, the structures used to close the gap provides a component which links the distal end of the housing to the proximal end and it can therefore have an influence on the force measurement. FIGS. 8G to 8J illustrate embodiments of structures that can be used to close the space or gap between the distal end of the housing and the proximal end. For simplicity, other components of the proximal end assembly or housing are not shown in FIGS. 8C-8J, however, any of the components describe herein for the skin perfusion pressure determination device can be used in combination with components described with reference to FIGS. 8C-8J.

As illustrated in FIG. 8G, the space can be closed with a tube made from an elastic material or any other flexible material. The material of the tube would then compress and/or stretch as the skin perfusion pressure determination device is operated.

FIG. 8H illustrates the use of a bellows as described herein. The advantage of a bellows can be that the bellows structure can be engineered to deform with a lower force. In additional to the elasticity of the material, the structure of the bellows can be designed to let it compress easily. For example, certain sections of the bellows can be thin out to help it compress with even lower forces as described in more detail herein.

FIG. 8I illustrates the use of a bag-like structure where there is some excessive material. In this embodiment, the bag-like structure deforms (as opposed to the material stretching) as the distal end of the housing and the proximal end move relative to each other. While this bag-like structure can change shape with very low force, it can be harder to clean than a bellows or tube structure.

FIG. 8J illustrates the use of a bag-like structure which encompasses the proximal end of the device. The bag material could be skin-compatible or biocompatible and not interfere with the operation of the optical sensor. In some embodiments, the bag can be replaceable and it can be changed between uses in order to provide a sterile interface to the target area (i.e. in this example, the bag is a one-use disposable component).

In some embodiments, the structure linking the distal end of the device and the proximal end and covering up the gap could be used as the spring. In such embodiments, the internal spring 811 is not required and the structure linking the distal end of the device and the proximal end and covering up the gap is used as a spring 811 is used in the skin perfusion pressure determination device 804. In some embodiments, a metal spring can allows the spring constants to be varied depending on the type of metal spring used.

The bellows 809, 909, 1109, 1209, and 1309 in FIGS. 7A-13K can be the gap closing structures described herein implemented in the form of bellows. In some embodiments, the bellows can be connected to the proximal end cap 808 and the proximal end of case 817. The force sensor which measures the force on the skin can be located between the proximal end cap 808 and the plunger 810. In such embodiments, there can be the possibility that some part of the force applied to the skin is taken up in the bellows and does not pass through the force sensor. If this is not taken account of, this can lead to measurement errors. In order to take account of this, several steps can be taken. In some embodiments, the bellows can be designed to compress very easily, i.e. with a very low force. This can be achieved by using soft materials and using the hinged structure in the bellows design. The force required to compress the bellows can be small in comparison to the forces that are applied to the target area and which would be measured. Additionally or alternatively, the force sensor can be calibrated with the bellows in place. This can take account of the force taken up/exerted by the bellows in the force sensor calculation and force calculation. In a bellows, the material properties are not only relied on to enable the compression of the structure, but structural features can be designed in, such as hinges or thinned out wall sections which aid in the compression. This will allow for the device to be less affected by changes in the material properties, which may occur due to ageing, temperature changes, etc. In some embodiments, the bellows 809 does not couple to the proximal end cap 808 but instead couple to an intermediate plate 875 as shown in FIG. 8K. A force sensor 876 can be used between the proximal end cap 808 and the intermediate plate 875. This would remove the influence of the bellows on the force measurement. In some embodiments, the optical sensor would still be located in the proximal end cap 808. In some embodiments, the force sensor 876 can be used instead of or in addition to force sensor described herein with the sensor assembly 814. In some embodiments, an end feature of the plunger 810 can be shaped to provide the function of this intermediate plate, as illustrated in FIG. 8L.

In some embodiments, the skin perfusion pressure determination device can determine the skin perfusion pressure or a measurement or index of skin perfusion pressure by positioning a proximal end of a skin perfusion pressure determination device on a target area of patient, the skin perfusion pressure determination device comprising a bellows portion. A force is then applied to the skin perfusion pressure determination device against the target area, causing the bellows portion to contract. The force and/or pressure applied to the target area by the skin perfusion pressure determination device can be measured using a first sensor within the device. The blood perfusion in the target area beneath the proximal end can be measured using a second sensor within the device. After the device detects that blood flow has been occluded in the target area, the force applied to the target area at a controlled rate can be released at a controlled rate by expanding the spring and the bellows portion as described herein. As used herein, obtaining or determining a skin perfusion pressure or taking a skin perfusion pressure measurement can refer to obtaining or determining an index or measurement which is based on a perfusion pressure and does not require that the perfusion pressure itself be measured. Additionally, as used herein, the one or more sensors used to sense or detect a parameter associated with an amount of blood perfusion at the target area can be detecting the onset of the pulse waveform (i.e. the onset of blood flow into the tissue) and/or the amount of perfusion. In some embodiments, the one or more sensors used to sense or detect a parameter associated with an amount of blood perfusion at the target area can detect that perfusion occurring and not necessarily how much or the amount of blood perfusion. For example, the one or more sensors used to sense or detect a parameter associated with an amount of blood perfusion at the target area can determine a measure for when perfusion starts or exists in a tissue area.

The skin perfusion pressure determination device can utilize various designs such as described above and as further described herein incorporating the sensors and signal processing elements into an elongate housing. In some embodiments, the skin perfusion pressure determination device described herein can be incorporate various features of the skin perfusion pressure determination device described in International Application No. PCT/EP2018/055940, filed Mar. 9, 2018, titled "DEVICE, APPARATUS AND METHOD OF DETERMINING SKIN PERFUSION PRESSURE," the disclosure of which is incorporated by reference herein. In some embodiments, the skin perfusion pressure determination device can incorporate features of International Application No. PCT/EP2018/055940, including, but not limited to, the displays, indicators, LEDs, symbols, methods of use, and any other features described in more details therein.

The skin perfusion pressure determination device can include an elongate housing having a proximal end and a distal end. The elongate housing can include a sensor module provided within the elongate housing and the sensor module can be used to detect a pressure exerted on a target area and/or an amount of blood perfusion at the target area. In some embodiments, the sensor module can be used to detect a pressure exerted on a target area and/or an amount of blood perfusion at the target area with methods or devices similar to those described herein, specifically with reference to the sensor module and signal processing elements described with reference to FIG. 2. In some embodiments, a proximal end assembly at the proximal end of the housing can include a proximal end cap at the proximal end of the proximal end assembly. In some embodiments, the proximal end cap and/or the proximal end assembly can contact and exert a pressure on the target area. In some embodiments, the elongate housing can include a display to provide feedback of the pressure exerted on a target area and/or the amount of blood perfusion at the target area. In some embodiments, a communication device can be used for providing data transfer from the skin perfusion pressure determination device to a control unit, remote computer, and/or data storage device. In some embodiments, the features, integers, characteristics or groups described in conjunction with any of the embodiments described in FIGS. 7-28 herein are to be understood to be applicable to any other of the embodiments described in FIGS. 7-28 or to any other aspect, embodiment or example described herein.

Figure 9A:
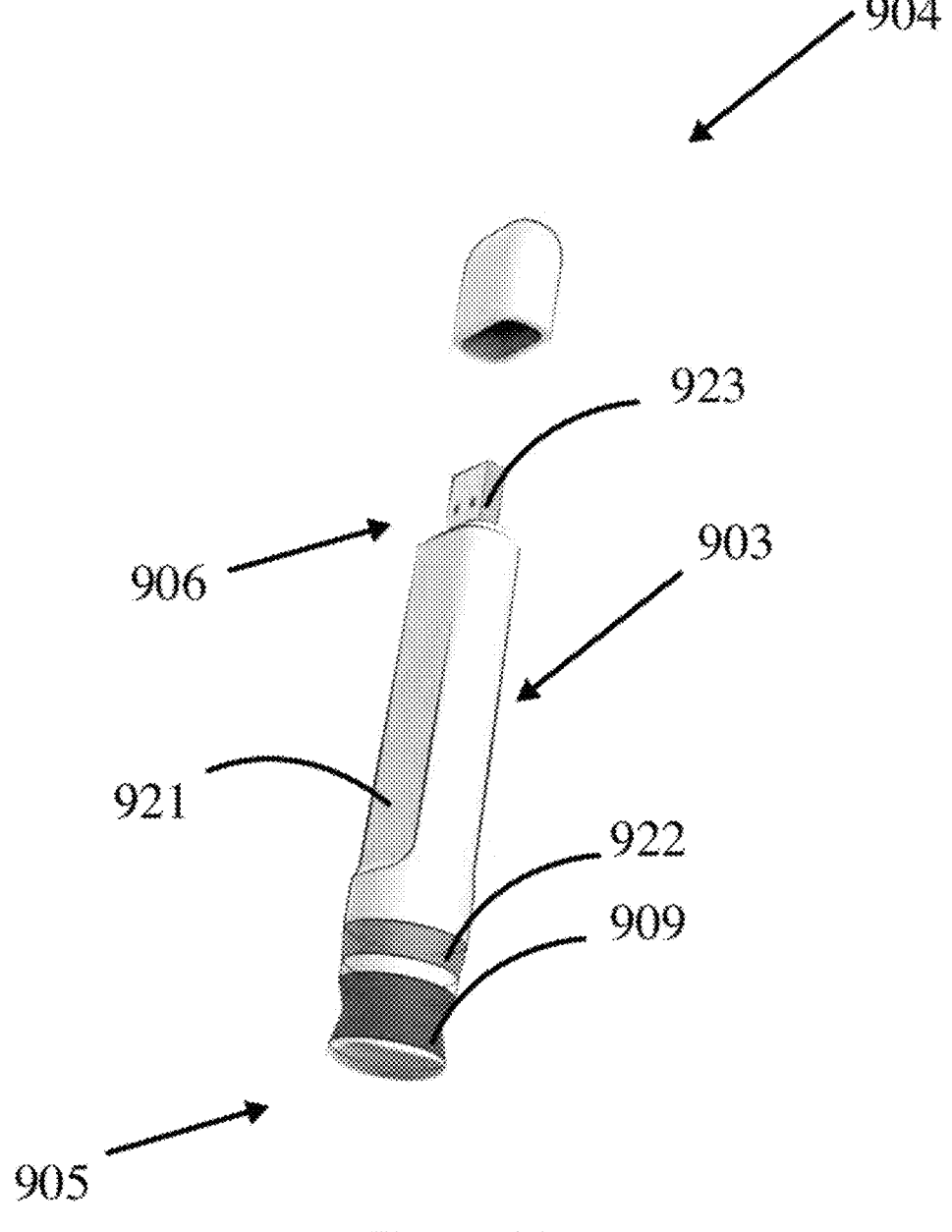
FIGS. 9A-9F illustrate an embodiment of a skin perfusion pressure determination device utilizing an integrated USB connector.
Figure 9B:
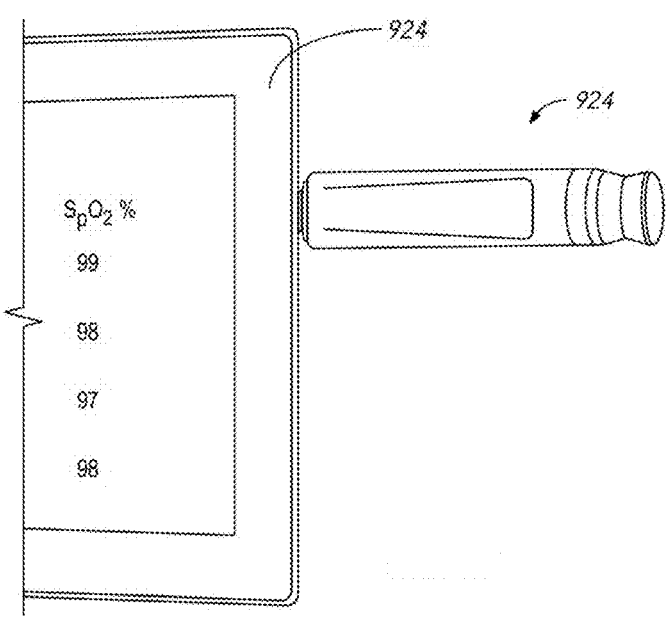
Figure 9C:
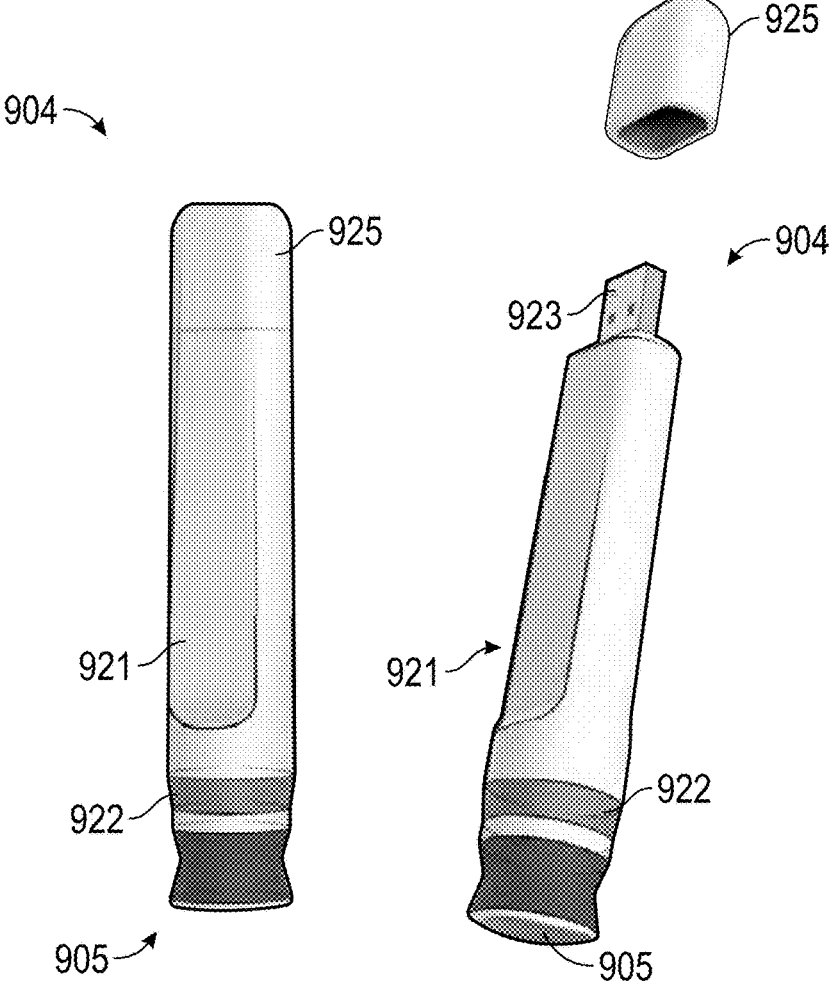

FIGS. 9A-9F illustrate an embodiment of a skin perfusion pressure determination device utilizing an integrated USB connector 923. The skin perfusion pressure determination device of FIGS. 9A-9F can be similar to and can include similar components as the skin perfusion pressure determination device described with reference to FIGS. 7A-7B and 8A-8B. The skin perfusion pressure determination device 904 can be a hand-held device with an elongate housing 903 including a grip portion 921 and a display 922. The grip portion 921 can be indented as illustrated in FIGS. 9A-9C to allow for the user to have a more comfortable and controlled grip on the device. The grip portion 921 can provide a surface which may include a flat surface for holding and controlling the skin perfusion pressure determination device. The grip portion 921 can include contoured sides of the elongate housing 903. In some cases, the grip portion 921 can have axial symmetry and as used herein, the contoured side can refer to a contour on the external face of a cylinder or the curved or contoured surface of the grip portion. The display 922 as illustrated in FIG. 9A-9C can be an LED circumferential display that wraps around the body of the device 904. The LED display can provide an indication of pressure or feedback of the pressure. As illustrated in FIG. 9A-9C, the LED display can be provided proximal to the grip portion and distal to the proximal end 905 of the elongate housing 903. However, the LED display can be provided anywhere on the device 904, including but not limited to, at the proximal or distal end of the device. The grip portion 921 of the device 904 can allow for the user to hold the device and provide control when the proximal end 905 of the skin perfusion pressure determination device 904 is placed on the target tissue area or skin surface.

In some embodiments, the elongate housing 903 can include a proximal end assembly and bellows portion as described with reference to FIGS. 7A and 8T. The bellows portion 909 can contract when the proximal end cap is in contact with the target tissue area and force is applied from the skin perfusion pressure determination device to the target area. In some embodiments, as described in more detail herein, when the proximal end cap is in contact with the target tissue area and force is applied from the skin perfusion pressure determination device to the target area, the spring within the proximal end assembly contracts which can cause the bellows portion 909 to contract. As illustrated in FIGS. 9A-9C the bellows portion can have a waisted shape and can contract inward when the force is applied. In other embodiments, the bellows portion can have a diamond, bulb, toroidal, or kicked out shape and can contract and extend outward or kick out when the force is applied.

The device 904 can include a USB connector 923 at the distal end 906 of the device for providing communication between the skin perfusion pressure determination device 904 and a computer. In some embodiments, the USB connector 923 can be used for charging the skin perfusion pressure determination device 904. For example, as illustrated in FIG. 9B, the USB connector 923 portion of the skin perfusion pressure determination device 904 can be plugged into a computer 924. In some embodiments, the device can incorporate any type of connector on the distal end 906. The device can use a USB connector or any other computer or device connectors that allows communication of data between computers or between a computer and computer peripherals.

In some embodiments, the devices described herein can communicate with an external device in several ways. For example, a cable can be attached permanently to the pen, a cable can be detached from the pen and connected via a connector when used, via a cradle, i.e. by placing the pen into a cradle after it has been used and the cradle is connected to the pc or external display, and/or wireless.

Figures 9D, 9E, 9F:
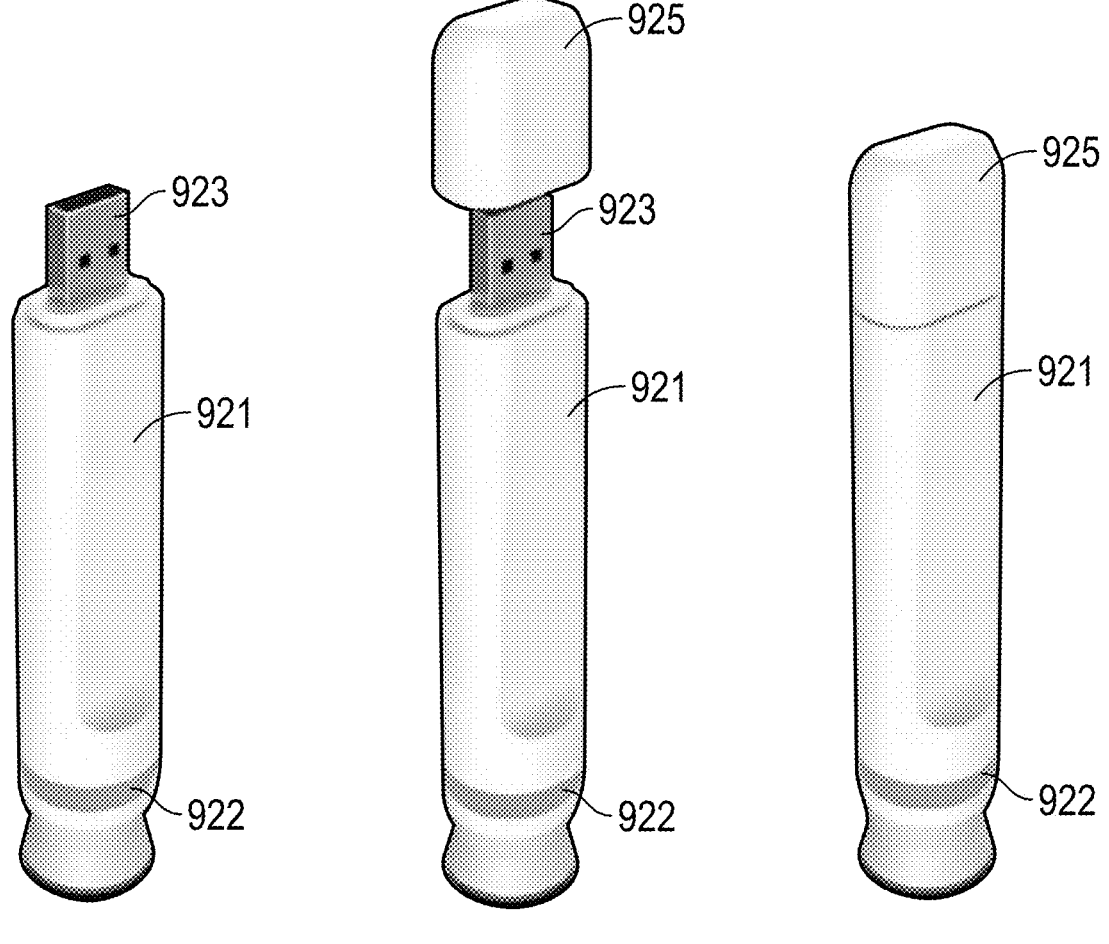

Data collected by the skin perfusion pressure determination device 904 can be transferred to the computer or other electronic device for storage and/or processing. FIG. 9C illustrates a removable end cap 925 that can be positioned over the USB connector 923 portion of the skin perfusion pressure determination device 904 when the USB connector 923 is not in use. FIG. 9C illustrates a skin perfusion pressure determination device 904 with the end cap 925 covering the USB connector 923 and a skin perfusion pressure determination device 904 with the end cap 925 removed from the USB connector 923. FIGS. 9D-9F illustrate embodiments of the skin perfusion pressure determination device 904 with the USB connector with the end cap 925 completely removed (FIG. 9D), positioned just above the USB connector 923 (FIG. 9E), and completely covering the USB connector 923 (FIG. 9F). In some cases, the USB can be on any portion of the device not just the distal end of the device. In some cases, the USB end cap does not have to be removable and instead can be hinged or can slide to expose the USB. In some cases, the USB end is not capped but covered with a piece of material that does not necessarily touch or cap the USB.

In some embodiments, the shape of the skin perfusion pressure determination device 904 can lead the user to instinctively hold the device in different ways. The gripping portion of the skin perfusion pressure determination device 904 can be designed to encourage or require a certain orientation of the device in the user's hand. The skin perfusion pressure determination device can require careful and steady (non-shaking) control of the pressure and/or the direction of pressure application at a 90-degree angle to the target tissue area. In some embodiments, the grip portion of the device can drive hand orientation. The hand orientation can drive arm alignment. In some embodiments, the skin perfusion pressure determination device 904 can be held in any orientation described herein, including the orientations suggested by the grip portions and shapes of the device described in later embodiments. For example, the palm grip shown in FIG. 10C, the pen grip shown in FIGS. 10E, 12C, 13I, 25A-25G, 26A-26B, 27A-27F, and 28A-28E, the barrel grip shown in FIGS. 11F-11G and 13H, and/or any other grip that allows the user to control the device can be used. The shape and size of the devices can require or encourage a different grip and arm alignment. In some embodiments, the different grip and/or arm alignment can change the degree of control over the steady application and/or removal of pressure on the target area. In some embodiments, the grip portion 921 can guide and/or aid the user to correctly orient and hold the pen at the correct angle.

In some embodiments, the display can be circumferential light guide illuminated by a LED. For example, a color or multiple colors can be used to guide the user through the procedure and use of the device. In some embodiments, the light guide can be any LED or arrangement of LEDs, not necessarily circumferential, to guide the user through the procedure.

Figure 10A:
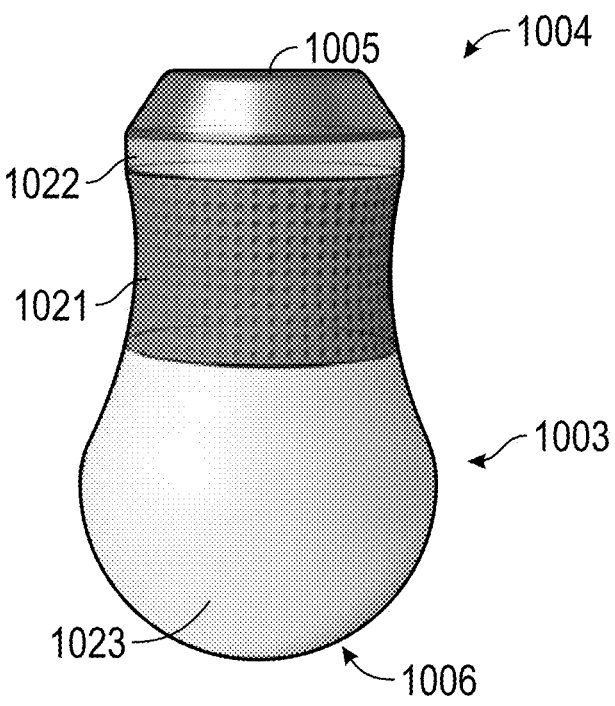
FIGS. 10A-10F illustrate embodiments of a skin perfusion pressure determination device with a palm grip.

FIGS. 10A-10F illustrate embodiments of a skin perfusion pressure determination device with a palm grip. The skin perfusion pressure determination device of FIGS. 10A-10F can be similar to and include similar components as the skin perfusion pressure determination device described with reference to FIGS. 7A-7B and 8A-8B. FIG. 10A illustrates a skin perfusion pressure determination device 1004 with an elongate housing 1003 comprising a proximal end 1005 and a distal end 1006. The elongate housing 1003 can be shaped and sized to be gripped with the palm of a user's hand.

Figure 10B:
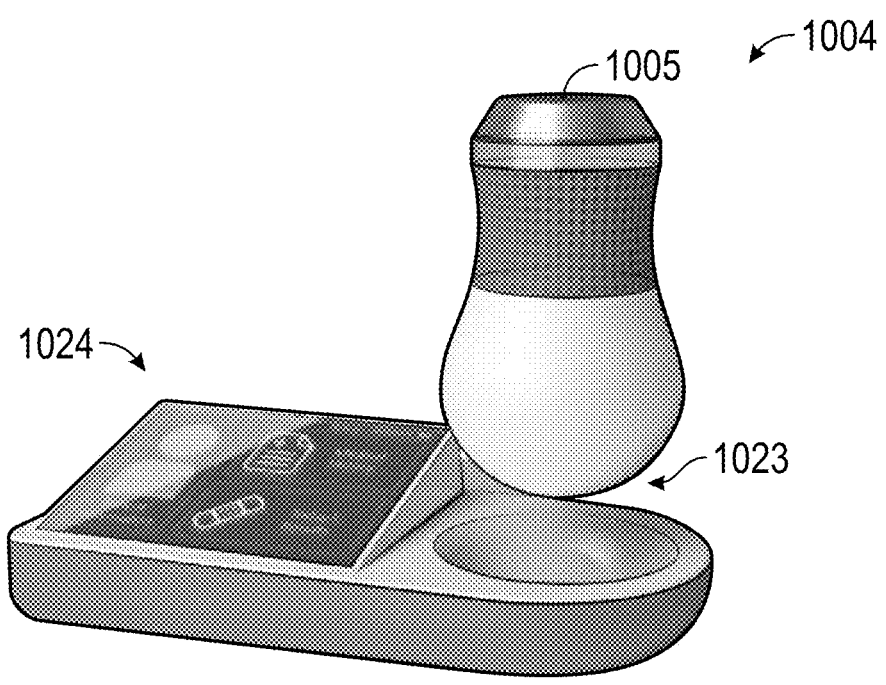

The skin perfusion pressure determination device 1004 can include a display 1022. The display 1022 as illustrated in FIG. 10A-10B can be a LED circumferential display that wraps around the body of the device 1004. The LED display can provide an indication of pressure or feedback of the pressure. The LED display can be provided anywhere on the device 1004, including but not limited to, the proximal or distal end of the device.

The skin perfusion pressure determination device 1004 can include a contoured or waisted grip portion 1021 and a rounded distal end 1006 that provides a palm grip portion 1023. The waisted grip portion 1021 can provide a surface for holding and controlling the skin perfusion pressure determination device. The grip portion 1021 can include a waisted contour of the elongate housing. The palm grip portion 1023 can have a bulb-like shape that allows for the skin perfusion pressure determination device 1004 to rest comfortably in the palm of a user's hand as illustrated in FIGS. 10C-10F. The waisted grip portion 1021 and the palm grip portion can allow for the user to hold the device in the palm of their hand and provide control when the proximal end 1005 of the skin perfusion pressure determination device 1004 is placed on the skin surface. In some embodiments, the grip portion can be made of a grip material. The grip material can be a non-slip material that improves the users grip on the device and provides stability. In some embodiments, the grip material can have protrusions or bumps to provide an improved gripping surface. The grip material can be a rubber, foam, and/or fabric material.

As illustrated in FIG. 10A-10B, the LED display can be provided proximal to the waisted grip portion 1021 and distal to the proximal end 1005 of the elongate housing 1003. However, the LED display can be provided anywhere on the device 1004, including but not limited to, at the proximal or distal end of the device.

FIG. 10B illustrates an embodiment of the skin perfusion pressure determination device 1004 docked to a docking station. As illustrated in FIG. 10B, the skin perfusion pressure determination device 1004 can be docked on the docking station 1024. The docking station can allow for data transfer and/or charging of the skin perfusion pressure determination device 1004. In some embodiments, the data transfer and/or charging can be conducted through a wireless contact connection (shown in FIG. 10B) or the device can be electrically connected through an electrical connector. In some embodiments, the docking station can be a computer or other control unit. Data collected by the skin perfusion pressure determination device 1004 can be transferred to the computer or other electronic device for storage and/or processing.

The docking station 1024 can include a display that can be used to display information or data collected by the skin perfusion pressure determination device 1004 and/or provide controls or settings for the skin perfusion pressure determination device 1004. In some embodiments, the docking station can be used to calibrate the skin perfusion pressure determination device 1004. In some embodiments, the docking station provides a housing for storing the skin perfusion pressure determination device 1004. The skin perfusion pressure determination device 1004 can be docked into the docking station 1024 with the palm grip portion 1023 resting in the docking station as shown in FIG. 10B. In other embodiments, the skin perfusion pressure determination device 1004 can be docked into the docking station 1024 with the proximal or skin contacting end resting in the docking station or in any other configuration.

Figure 10C:
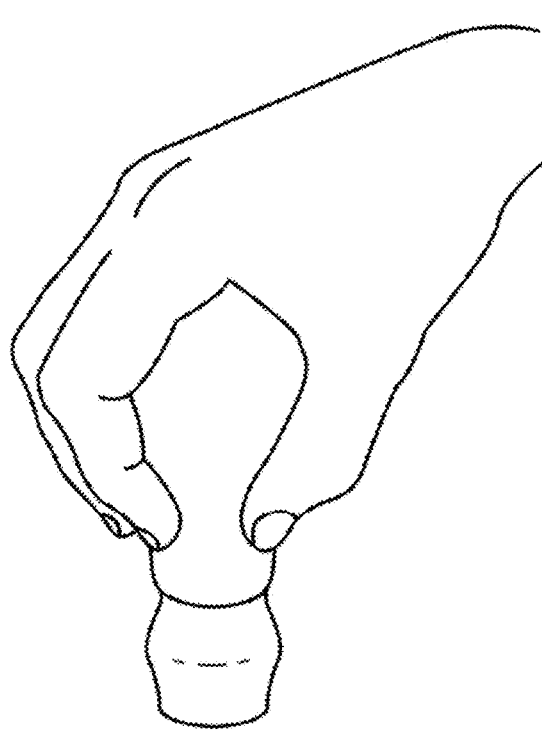
Figure 10D:
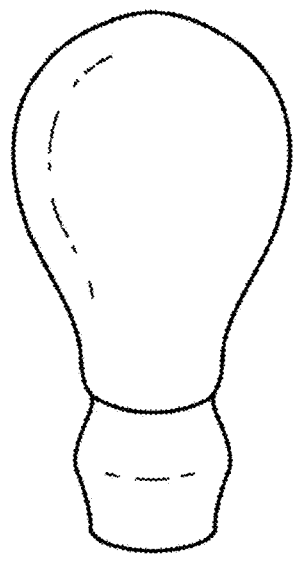
Figure 10E:
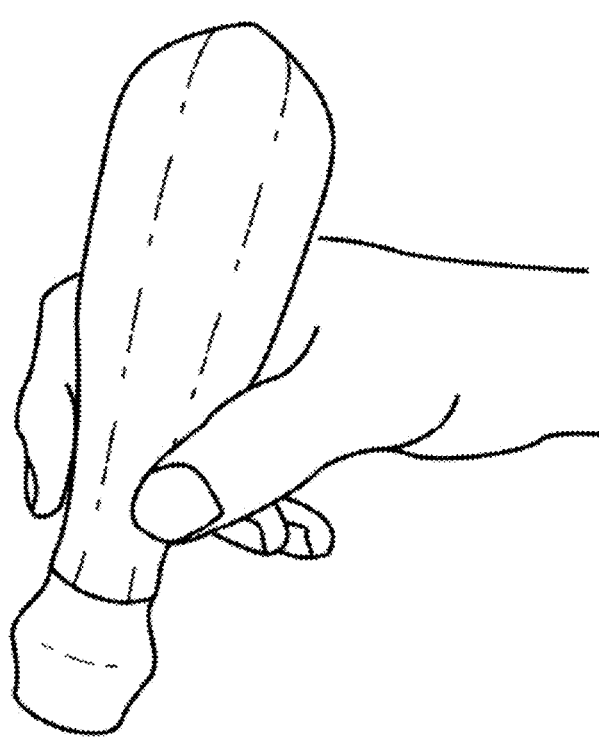
Figure 10F:
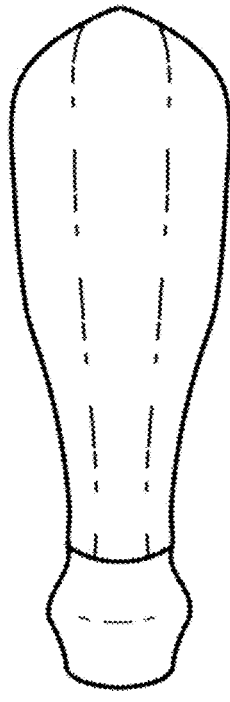

FIGS. 10C-10F illustrate various embodiments of a skin perfusion pressure determination device 1004 similar to the device described with reference to FIGS. 10A-10B. FIGS. 10C and 10E illustrate embodiments of the skin perfusion pressure determination device 1004 being gripped by a user. In some embodiments, the shape of the device can lead the user to instinctively hold the devices in different ways. For example, in FIG. 10C, the skin perfusion pressure determination device is held by the user at the distal end and the users palm covers the distal end. As illustrated in FIG. 10E, the skin perfusion pressure determination device can be held by the user like a pen, for example, between a thumb and index finger of the user. A grip where the device is positioned between the thumb and index finger of the user can be referred to herein as the pen grip or the external precision grip where the device is pinched between the thumb and index finger and the grip has two extra components of support for the device in the cleft of the thumb and support for the whole hand along its medial edge.

The skin perfusion pressure determination device can require careful and steady (non-shaking) control of the pressure and/or the direction of pressure application at a 90-degree angle to the target tissue area. In some embodiments, the grip portion of the device can drive hand orientation. In some embodiments, the hand orientation can drive arm alignment. For example, with the palm over a bulb or rounded surface similar to the palm grip portion 1023, a user is likely to naturally push down on the device. In some embodiments, when a user's hand grips a wide tube or pen shape the user's hand and arm can be at right angles to the direction of force. For example, the skin perfusion pressure determination device can be a tube-shaped device as illustrated in FIGS. 11A-11J (described later) and the user's hand can grip or wrap around the tube-shaped device with the user's hand and arm at right angles to the direction of force as illustrated in FIGS. 11F-11G. A grip where the hand can grip or wrap around the tube-shaped or elongate device can be referred to herein as a barrel grip or power grip where the user's fingers are bunched firmly around an object and in some instances overlapped by the thumb. In some variations of the barrel grip or power grip, the thumb can be positioned out straight along the handle. As shown in FIGS. 10C and FIGS. 11F-11G, the shape and size of the devices can require or encourage a different grip and arm alignment. In some embodiments, the different grip and/or arm alignment can change the degree of control over the steady application and/or removal of pressure on the target area. In some embodiments, the grip portion 1021 can guide and/or aid the user to correctly orient and hold the pen at the correct angle.

Various different grips can be used for the devices described herein including, but not limited to, a power grip, a pinch grip, an external precision grip, an internal precision grip, an ulnar storage grip, or other grips. In some embodiments, the skin perfusion pressure determination device 1004 can be held in any orientation described herein, including the orientations suggested by the grip portions and shapes of the device described in other embodiments. For example, the palm grip shown in FIG. 10C, the pen grip shown in FIGS. 10E, 12C, and 13I, the barrel grip shown in FIGS. 11F-11G and 13H, and/or any other grip that allows the user to control the device can be used.

In some embodiments, the display can be circumferential light guide illuminated by a LED. For example, a color or multiple colors can be used to guide the user through the procedure and use of the device. In some embodiments, the light guide can be any LED or arrangement of LEDs, not necessarily circumferential, to guide the user through the procedure.

In some embodiments, the elongate housing 1003 can include a proximal end assembly and bellows portion as described with reference to FIGS. 7A-7B and 8A-8B. In some embodiments, the bellows portion can contract when the proximal end cap is in contact with the target tissue area and force is applied from the skin perfusion pressure determination device to the target area. In some embodiments, the bellows portion can have a waisted shape and can contract inward when the force is applied. In other embodiments, the bellows portion can have a diamond, bulb, toroidal, or kicked out shape and can contract and extend outward or kick out when the force is applied.

Figure 11A:
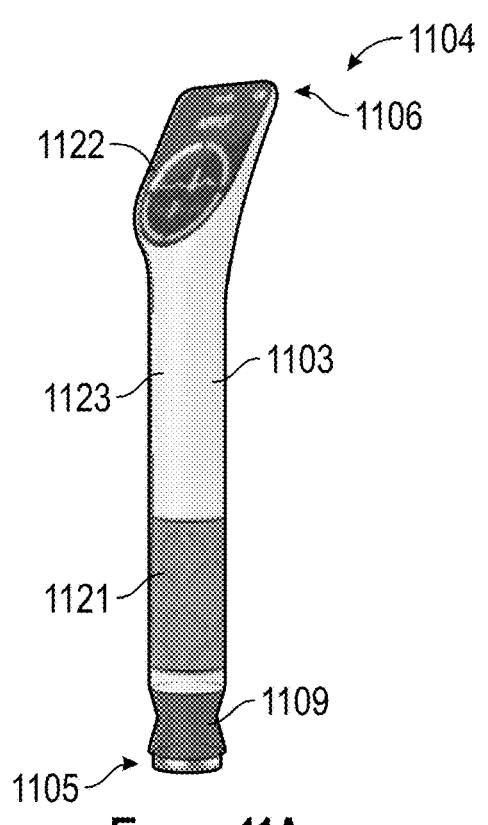
FIGS. 11A-11J illustrate embodiments of a skin perfusion pressure determination device with a display.
Figure 11B:
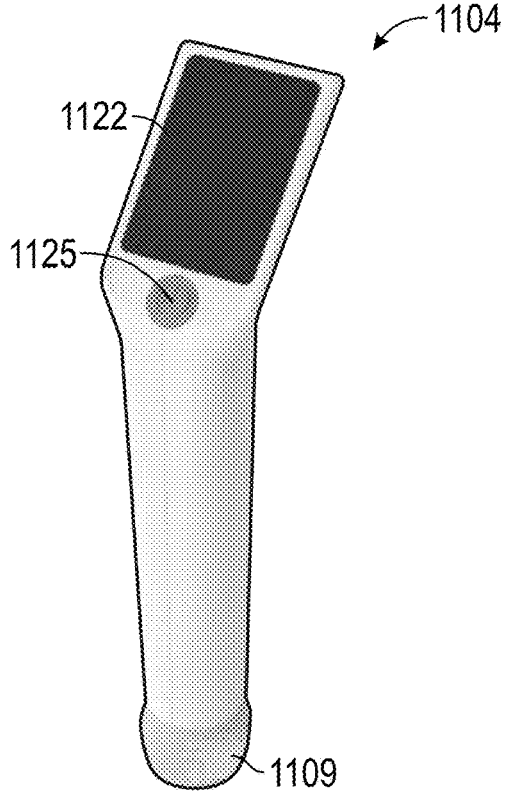
Figure 11C:
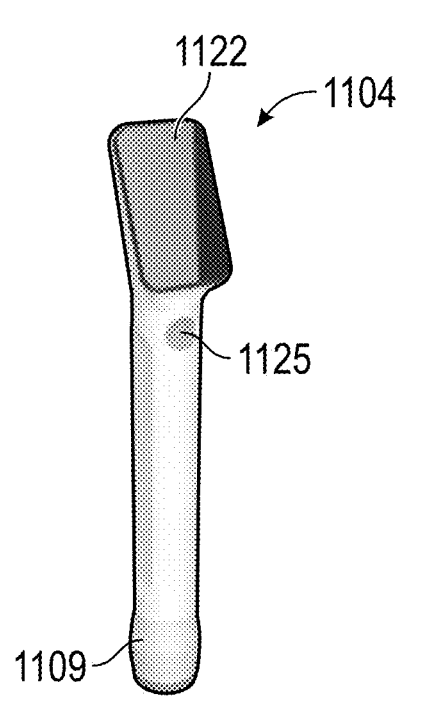
Figure 11D:
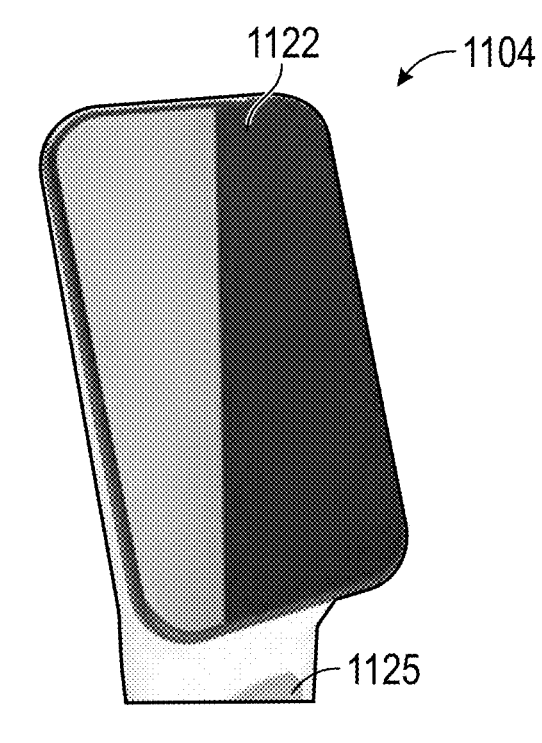
Figure 11E:
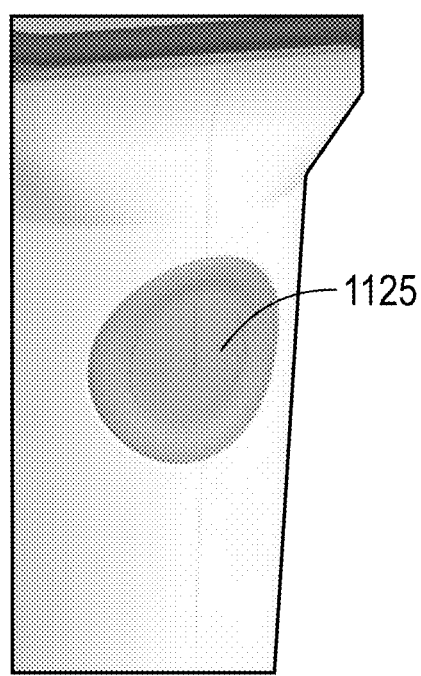
Figure 11F:
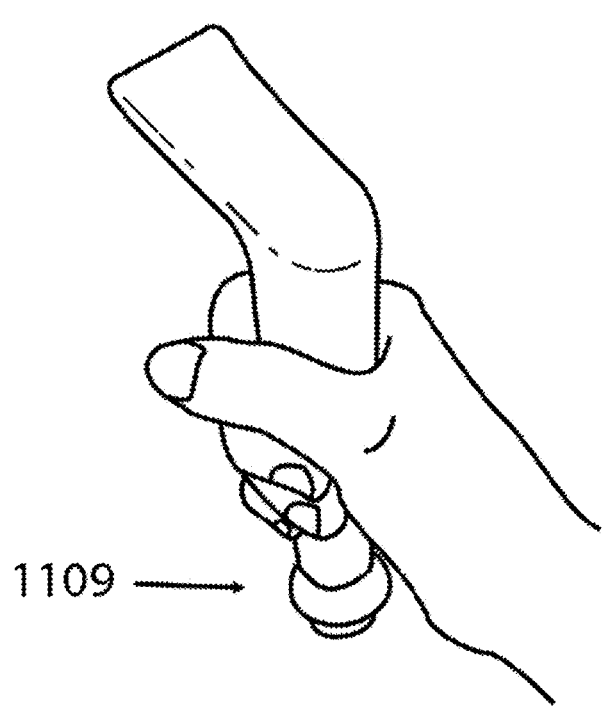
Figure 11G:
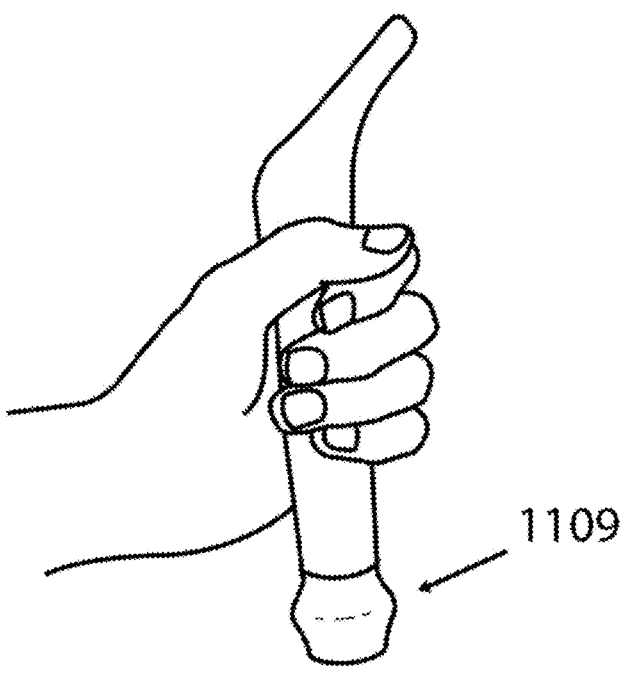

FIGS. 11A-11J illustrate embodiments of a skin perfusion pressure determination device with a display. The skin perfusion pressure determination device of FIGS. 11A-11J can be similar to and include similar components as the skin perfusion pressure determination device described with reference to FIGS. 7A-7B and 8A-8B. FIG. 11A illustrates a skin perfusion pressure determination device 1104 with an elongate housing 1103 that includes a display screen 1122. The elongate housing 1103 can have a proximal end 1105 and a distal end 1106. The skin perfusion pressure determination device 1104 can include a front facing display screen 1122 to aid in orientation and provide information and feedback to the user during use. In some embodiments, the front facing display screen 1122 can guide the user to hold the device in a certain orientation. The display screen 1122 as illustrated in FIG. 11A-11E can be positioned at the distal end 1106 of the device. This positioning can allow for the display to be readable as the proximal or skin contacting end 1105 of the skin perfusion pressure determination device 1104 is contacting the skin. The screen display 1122 can provide an indication of skin perfusion pressure, pressure applied to the skin, and/or feedback to the user. The screen display 1122 can be provided anywhere on the device 1104.

In some embodiments, the skin perfusion pressure determination device 1104 can incorporate a communication device for providing data transfer from the skin perfusion pressure determination device to a computer or control unit. In some embodiments, the skin perfusion pressure determination device 1104 can incorporate wireless communication to communicate with a computer or control unit. The skin perfusion pressure determination device 1104 can include a grip to provide a surface for holding and controlling the skin perfusion pressure determination device. The grip can include a grip portion 1121 and a palm grip portion 1123. The palm grip portion 1123 can have a cylindrical shape and can allow the skin perfusion pressure determination device 1104 to rest comfortably in the palm of a user's hand as illustrated in FIGS. 11F-11G and can allow for the user to hold the device in the palm of their hand and provide control when the proximal end 1105 of the skin perfusion pressure determination device 1104 is placed on the skin surface. The grip portion 1121 can include a grip material positioned on the proximal end of the housing proximal to the screen. In some embodiments, the palm grip portion 1123 can include a grip material (not shown). In some embodiments, the grip material can be a non-slip material that improves the users grip on the device and provides stability. In some embodiments, the grip material can have protrusions or bumps to provide an improved gripping surface. The grip material can be a rubber, foam, and/or fabric material. In some embodiments, the grip portion 1121 and/or the palm grip portion 1123 can be a grooved, centrally thickened, or hilted design to prevent or reduce the user's hand and/or finger from sliding down the housing. These can prevent the user's hand from slipping down onto the target area, for example, the patient skin or wound. The grooved, centrally thickened, or hilted design, can be useful for use with gloves or wet conditions where the grip on the device may be compromised.

As described previously herein, FIGS. 11F-11G illustrate an embodiment of the skin perfusion pressure determination device 1104 being gripped by a user. As described herein, the shape of the device can lead the user to instinctively hold the devices in different ways. The skin perfusion pressure determination device can require careful and steady (non-shaking) control of the pressure and/or the direction of pressure application at a 90-degree angle to the target tissue area. In some embodiments, the grip portion of the device can drive hand orientation. The hand orientation can drive arm alignment. In some embodiments, the skin perfusion pressure determination device 1104 can be held in any orientation described herein, including the orientations suggested by the grip portions and shapes of the device described in other embodiments. For example, the palm grip shown in FIG. 10C, the pen grip shown in FIGS. 10E, 12C, and 13I, the barrel grip shown in FIGS. 11F-11G and 13H, and/or any other grip that allows the user to control the device can be used. The shape and size of the devices can require or encourage a different grip and arm alignment. In some embodiments, the different grip and/or arm alignment can change the degree of control over the steady application and/or removal of pressure on the target area. In some embodiments, the grip portion 1121 can guide and/or aid the user to correctly orient and hold the pen at the correct angle.

In some embodiments, the display can be a light guide illuminated by a LED or a screen. For example, a color or multiple colors can be used to guide the user through the procedure and use of the device.

As illustrated in FIGS. 11B-11E, the skin perfusion pressure determination device 1104 can include a power button or switch 1125. In some embodiments, the power button or switch 1125 can be located on any portion of the skin perfusion pressure determination device 1104. The switch can be used to turn the skin perfusion pressure determination device on and/or off. In some embodiments, the display screen 1122 can include a touch screen. The touch screen display screen can include the power button or switch 1125.

In some embodiments, the elongate housing 1103 can include a proximal end assembly and bellows portion 1109 as described with reference to FIGS. 7A-7B and 8A-8B. In some embodiments, the bellows portion 1109 can contract when the proximal end cap is in contact with the target tissue area and force is applied from the skin perfusion pressure determination device to the target area. In some embodiments, as described in more detail herein, when the proximal end cap is in contact with the target tissue area and force is applied from the skin perfusion pressure determination device to the target area, the spring within the proximal end assembly contracts which can cause the bellows portion 909 to contract. In some embodiments, as illustrated in FIG. 11A, the bellows portion 1109 can have a waisted shape and can contract inward when the force is applied. In other embodiments, as illustrated in FIGS. 11B-11C and 11F-11J, the bellows portion 1109 can have a diamond, bulb, toroidal, or kicked out shape and can contract and extend outward or kick out when the force is applied.

Figure 11H:
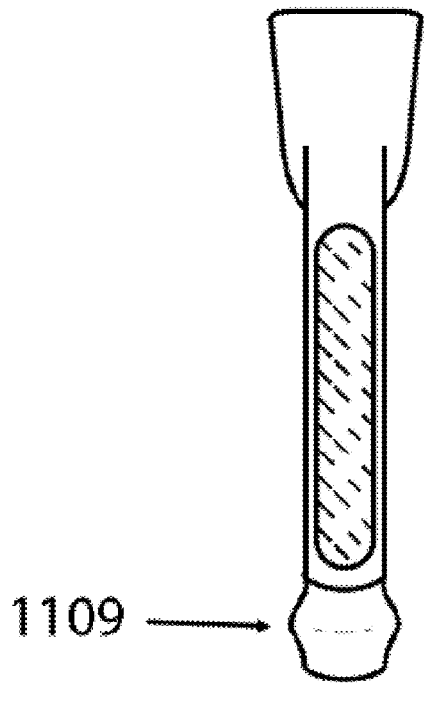
Figure 11I:
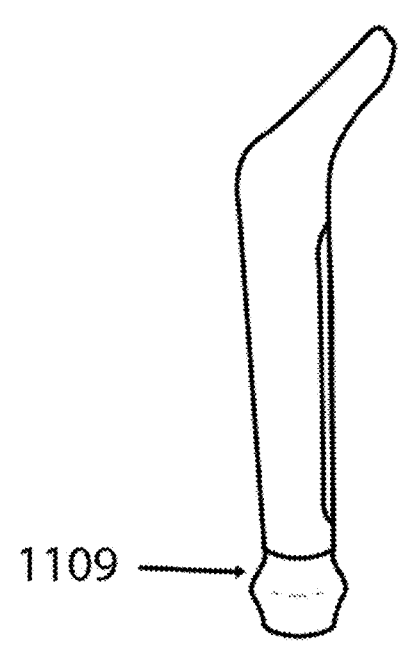
Figure 11J:
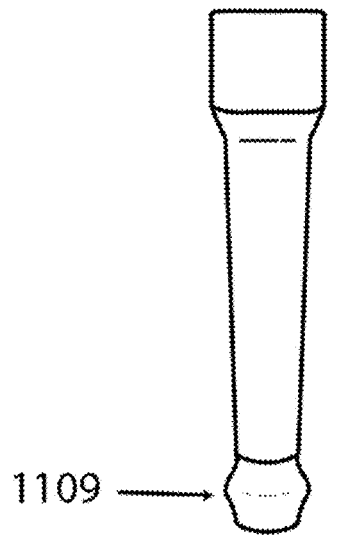

FIG. 11H illustrates a back side of an embodiment of the skin perfusion pressure determination device 1104. FIG. 11I illustrates a side view of an embodiment of the skin perfusion pressure determination device 1104. FIG. 11J illustrates a front view of an embodiment of the skin perfusion pressure determination device 1104.

Figures 12A, 12B:
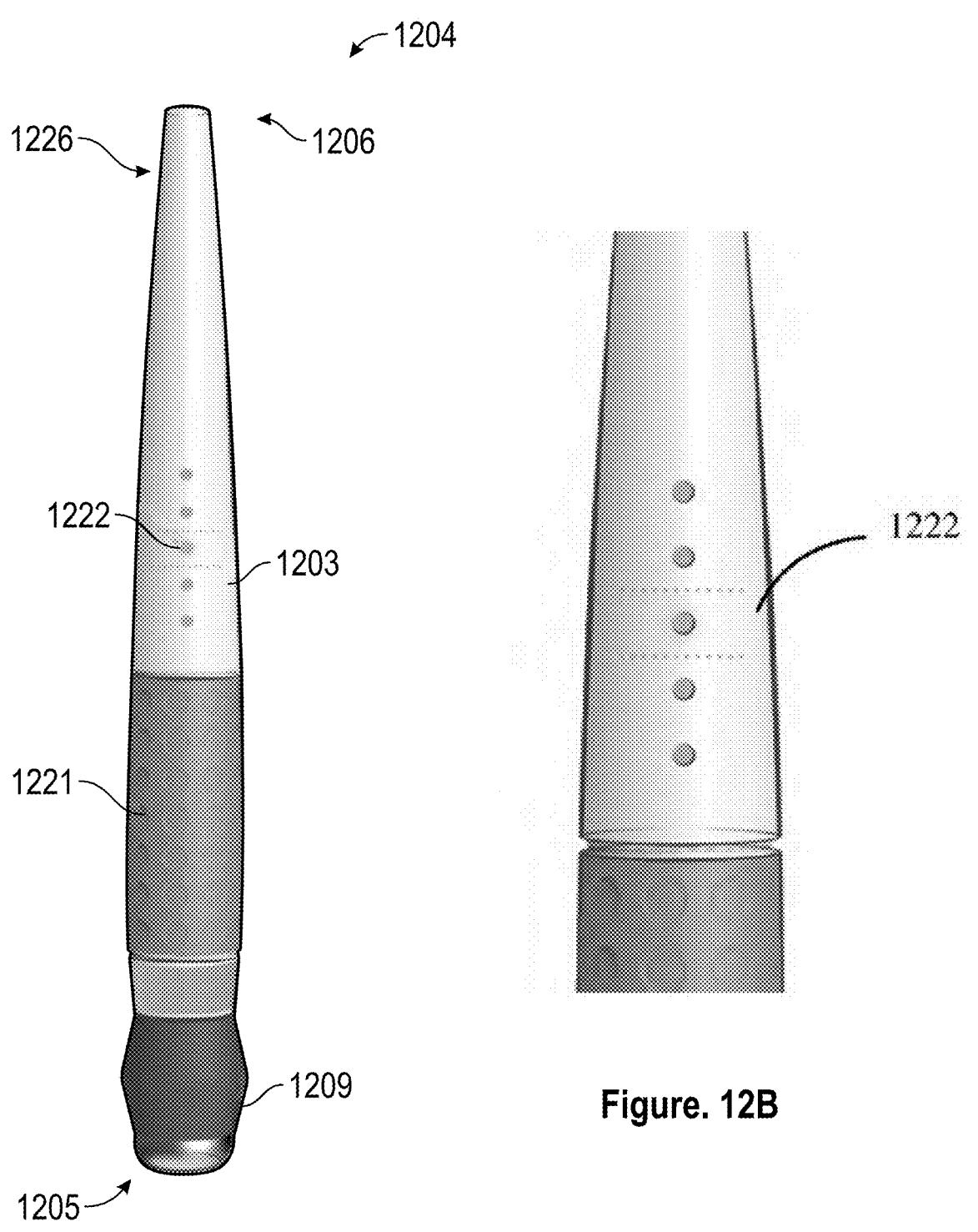
FIGS. 12A-12D illustrate embodiments of a skin perfusion pressure determination device with indicators.

FIGS. 12A-12E illustrate embodiments of a skin perfusion pressure determination device with indicators. The skin perfusion pressure determination device of FIGS. 12A-12F can be similar to and include similar components as the skin perfusion pressure determination device described with reference to FIGS. 7A-7B and 8A-8B. The skin perfusion pressure determination device 1204 can comprise an elongate housing 1203. The elongate housing 1203 can have a proximal end 1205 and a distal end 1206. FIG. 12A illustrates a skin perfusion pressure determination device 1204 that includes a display 1222. The skin perfusion pressure determination device 1204 can include a display 1222 with one or more LEDs as illustrated in FIG. 12B. The LED display can provide an indication of the pressure applied to the skin and/or feedback to the user.

In some embodiments, the LED display can provide feedback of the pressure exerted on a target area and/or the amount of blood perfusion at the target area. The LED display can be provided anywhere on the elongate housing 1203 of the device 1204. This positioning can allow for the display to be readable as the proximal or skin contacting end 1205 of the skin perfusion pressure determination device 1204 is contacting the skin.

Figure 12C:
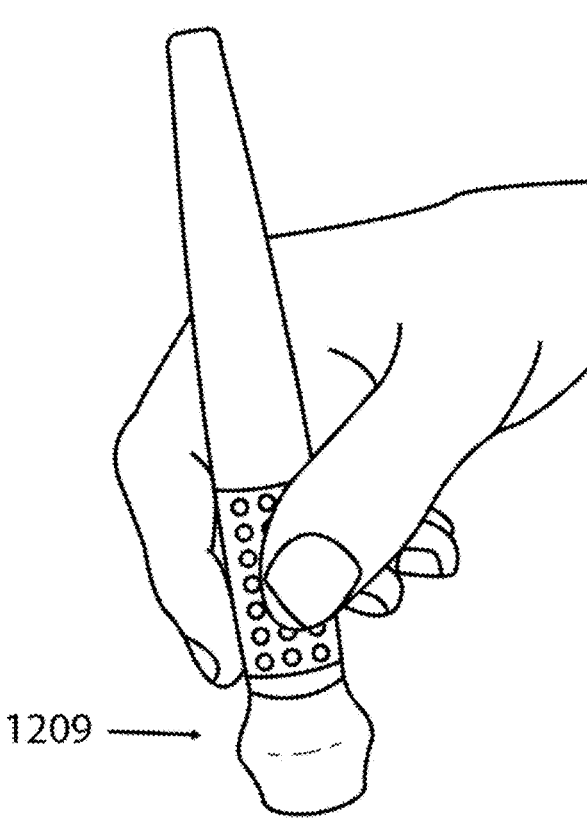
Figure 12D:
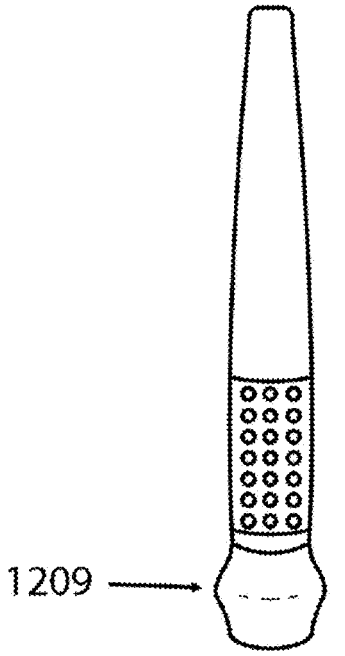

The skin perfusion pressure determination device 1204 can include a grip portion 1221 and a tapered distal end 1226. The grip portion can provide a surface for holding and controlling the skin perfusion pressure determination device. The grip portion 1221 comprises a grip material positioned on the proximal end of the elongate housing. The grip portion 1221 can have a cylindrical shape and can allow the skin perfusion pressure determination device 1204 to rest comfortably in a user's hand as illustrated in FIGS. 12C-12D and can allow for the user to hold the device in a controlled position when the proximal or skin contacting end 1205 of the skin perfusion pressure determination device 1204 is placed on the skin surface. In some embodiments, the grip material can be a non-slip material that improves the users grip on the device and provides stability. In some embodiments, the grip material can have protrusions or bumps to provide an improved gripping surface. The grip material can be a rubber, foam, and/or fabric material.

In some embodiments, the LED display can be positioned on the elongate housing 1203 distal to the grip portion 1221 and proximal to the tapered distal end 1226. The skin perfusion pressure determination device 1204 can be connected to a control unit, remote computer, electrical or charging assembly, or any other device. The skin perfusion pressure determination device can include a communication device for providing data transfer from the skin perfusion pressure determination device to a computer or control unit. In some embodiments, the communication device can include an electrical wiring connecting the skin perfusion pressure determination device 1204 to a control unit. In some embodiments, the communication device can include a connector which can be coupled to a cable or electrical wiring which links the device to a control unit. In some embodiments, the tapered distal end 1226 of the skin perfusion pressure determination device 1204 can include a cable assembly (not shown) that connects the distal end of the skin perfusion pressure determination device 1204 to a control unit or other device. In other embodiments, the communication device comprises a device for wireless communication.

Connecting the skin perfusion pressure determination device 1204 to a control unit or device can allow for data transfer and/or charging of the skin perfusion pressure determination device 1204. In some embodiments, the data transfer and/or charging can be conducted through an electrical connector extending from the tapered distal end 1226. In some embodiments, the electrical connector extending from the tapered distal end 1226 can be connected to a computer or other control unit. Data collected by the skin perfusion pressure determination device 1204 can be transferred to the computer or other electronic device for storage and/or processing. The electrical connector extending from the tapered distal end 1226 can be used to transfer data collected by the skin perfusion pressure determination device 1204 and/or provide controls or settings for the skin perfusion pressure determination device 1204. In some embodiments, the skin perfusion pressure determination device 1204 can be thin and have a minimal footprint. In some embodiments, the slim design of the skin perfusion pressure determination device 1204 can ease handling of the device and improve accuracy.

In some embodiments, the elongate housing 1203 can include a proximal end assembly and bellows portion 1209 as described with reference to FIGS. 7A-7B and 8A-8B. In some embodiments, the bellows portion 1209 can contract when the proximal end cap is in contact with the target tissue area and force is applied from the skin perfusion pressure determination device to the target area. In some embodiments, as illustrated in FIGS. 12A-12D, the bellows portion 1209 can have a diamond, bulb, toroidal, or kicked out shape and can contract and extend outward or kick out when the force is applied. In other embodiments, the bellows portion 1209 can have a waisted shape and can contract inward when the force is applied.

FIG. 12C illustrates an embodiment of the skin perfusion pressure determination device 1204 being gripped by a user. As described herein, the shape of the device can lead the user to instinctively hold the devices in different ways. The skin perfusion pressure determination device can require careful and steady (non-shaking) control of the pressure and/or the direction of pressure application at a 90-degree angle to the target tissue area. In some embodiments, the grip portion of the device can drive hand orientation. The hand orientation can drive arm alignment. In some embodiments, the skin perfusion pressure determination device 1204 can be held in any orientation described herein, including the orientations suggested by the grip portions and shapes of the device described in other embodiments. For example, the palm grip shown in FIG. 10C, the pen grip shown in FIGS. 10E, 12C, and 13I, the barrel grip shown in FIGS. 11F-11G and 13H, and/or any other grip that allows the user to control the device can be used. The shape and size of the devices can require or encourage a different grip and arm alignment. In some embodiments, the different grip and/or arm alignment can change the degree of control over the steady application and/or removal of pressure on the target area. In some embodiments, the grip portion 1221 can guide and/or aid the user to correctly orient and hold the pen at the correct angle.

In some embodiments, the display can be circumferential light guide illuminated by a LED. For example, a color or multiple colors can be used to guide the user through the procedure and use of the device. In some embodiments, the light guide can be any LED or arrangement of LEDs, not necessarily circumferential, to guide the user through the procedure.

Figure 13B:
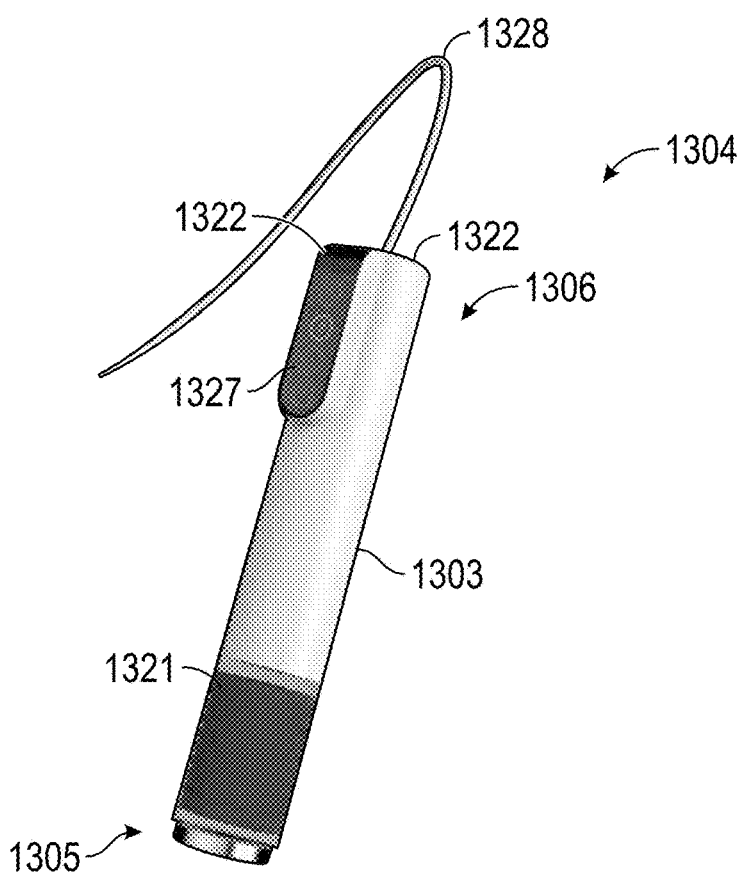
Figure 13B:
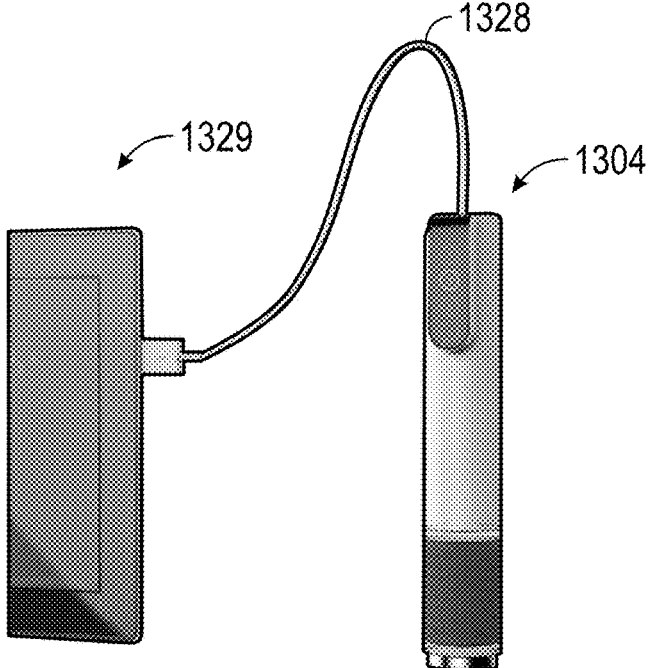

FIGS. 13A-13K illustrate embodiments of a skin perfusion pressure determination device. The skin perfusion pressure determination device of FIGS. 13A-13K can be similar to and include similar components as the skin perfusion pressure determination device described with reference to FIGS. 7A-7B and 8A-8B. The skin perfusion pressure determination device 1304 can comprise an elongate housing 1303. The elongate housing 1303 can have a proximal end 1305 and a distal end 1306. FIG. 13A illustrates a skin perfusion pressure determination device 1304 that includes a display to provide feedback of the pressure exerted on a target area and/or the amount of blood perfusion at the target area. In some embodiments, the display can include a plurality of LED displays.

In some embodiments, the skin perfusion pressure determination device 1304 includes a first display 1322 and a second display 1327. The first display 1322 can include an LED positioned on the top or distal most end 1306 of the skin perfusion pressure determination device 1304 as illustrated in FIG. 13F-13G. The second display 1327 can be positioned on the side of the skin perfusion pressure determination device 1304. In some embodiments, the first LED display 1322 can include a top display on the distal most end of the elongate housing and a second LED display 1327 can include a side display on a side of the proximal end of the elongate housing. The second display can include a row of indicators as illustrated in FIGS. 13A-13B and 13E-13F. The row of indicators can include number, color, symbol, and/or any other indicators. The first and/or second display 1322 and 1327 can provide an indication of the pressure applied to the skin and/or feedback to the user.

In some embodiments, the first display 1322 can provide an indication of pressure feedback and the second display 1327 can provide a location indicator and/or reading or measurement. This positioning of the first and second displays 1322 and 1327 can allow for the display to be readable as the proximal or skin contacting end 1305 of the skin perfusion pressure determination device 1304 is contacting the skin.

The skin perfusion pressure determination device 1304 can include a grip portion 1321. The grip portion 1321 can provide a surface for holding and controlling the skin perfusion pressure determination device 1304. The grip portion 1321 can include a grip material positioned on the proximal end of the elongate housing as illustrated in FIG. 13B. The grip portion 1321 can have a cylindrical shape and can allow the skin perfusion pressure determination device 1304 to rest comfortably in a user's hand as illustrated in FIGS. 13H-13I and can allow for the user to hold the device in a controlled position when the proximal or skin contacting end 1305 of the skin perfusion pressure determination device 1304 is placed on the skin surface. In some embodiments, the grip material can be a non-slip material that improves the users grip on the device and provides stability. In some embodiments, the grip material can have protrusions or bumps to provide an improved gripping surface. The grip material can be a rubber, foam, and/or fabric material.

The skin perfusion pressure determination device 1304 can include a communication device for providing data transfer from the skin perfusion pressure determination device to a computer or control unit. The skin perfusion pressure determination device 1304 can be connected to a control unit, remote computer, electrical or charging assembly, or any other device. In some embodiments, the distal end 1306 of the skin perfusion pressure determination device 1304 can include an electrical wire or cable 1328 that connects the distal end of the skin perfusion pressure determination device 1304 to a computer 1329 as illustrated in FIG. 13B.

Connecting the skin perfusion pressure determination device 1304 to a computer, control unit, or other device can allow for data transfer and/or charging of the skin perfusion pressure determination device 1304. In some embodiments, the data transfer and/or charging can be conducted through an electrical wire or cable 1328 extending from the distal end 1306. In some embodiments, the electrical wire or cable 1328 extending from the distal end 1306 can be connected to a computer, control unit, or other device. Data collected by the skin perfusion pressure determination device 1304 can be transferred to the computer or other electronic device for storage and/or processing. The electrical wire or cable 1328 extending from the distal end 1306 can be used to transfer data collected by the skin perfusion pressure determination device 1304 and/or provide controls or settings for the skin perfusion pressure determination device 1304.

Figure 13C:
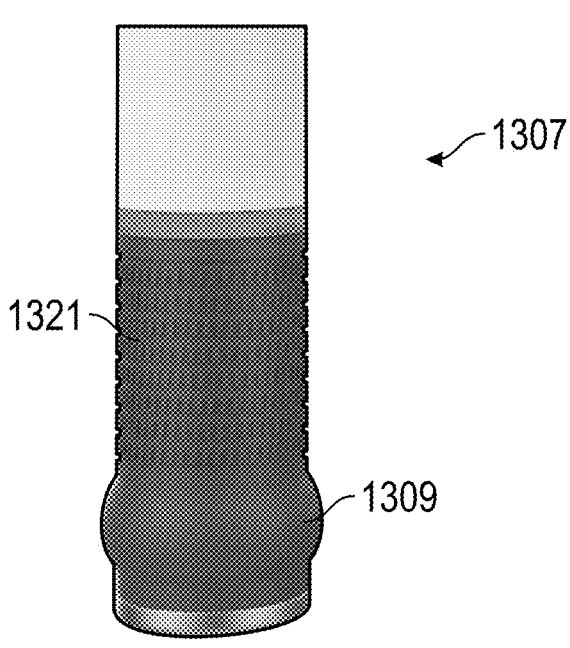
Figure 13D:
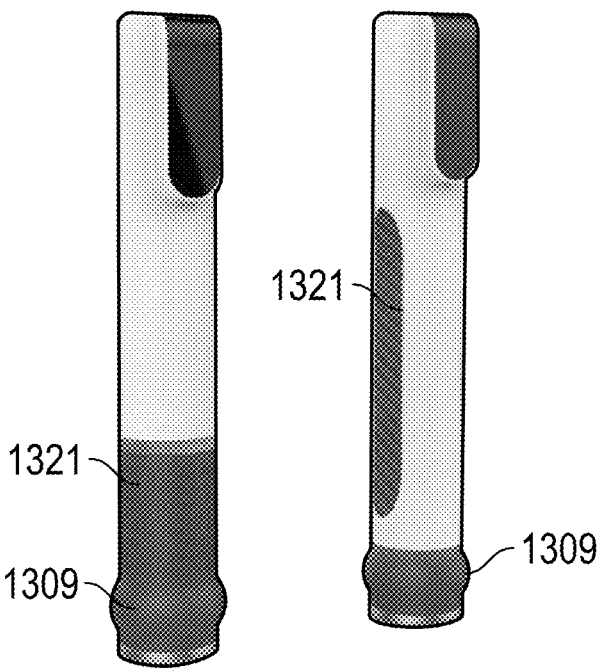

FIG. 13C illustrates a zoomed in view of the proximal end assembly 1307 of an embodiment of a skin perfusion pressure determination device 1304 shown in FIG. 13D. FIG. 13D illustrates two different grip portions 1321 of an embodiment of the skin perfusion pressure determination device 1304. The grip portion 1321 can be provided as a strip of material on the side of the skin perfusion pressure determination device 1304. In other embodiments, the grip portion 1321 can be provided as a piece of material wrapped around the barrel of the proximal end assembly as shown in one of the embodiment on the left side of FIG. 13D and the embodiment in FIG. 13C. In some embodiments, the grip portion can be formed integrally as part of the housing, as part of the moulding process, via in-mould decoration or two-shot moulding.

In some embodiments, the elongate housing 1303 can include a proximal end assembly and bellows portion 1309 as described with reference to FIGS. 7A-7B and 8A-8B. In some embodiments, the bellows portion 1309 can contract when the proximal end cap is in contact with the target tissue area and force is applied from the skin perfusion pressure determination device to the target area. In some embodiments, as illustrated in FIGS. 13C-13D and 13H-13K, the bellows portion 1309 can have a diamond, bulb, toroidal, or kicked out shape and can contract and extend outward or kick out when the force is applied. In other embodiments, the bellows portion 1309 can have a waisted shape and can contract inward when the force is applied.

Figure 13E:
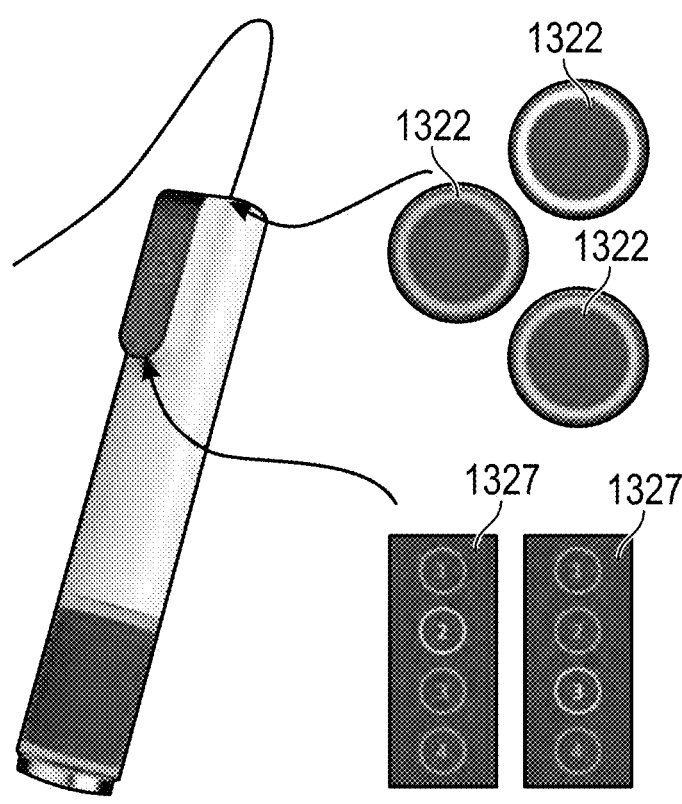
Figure 13F:
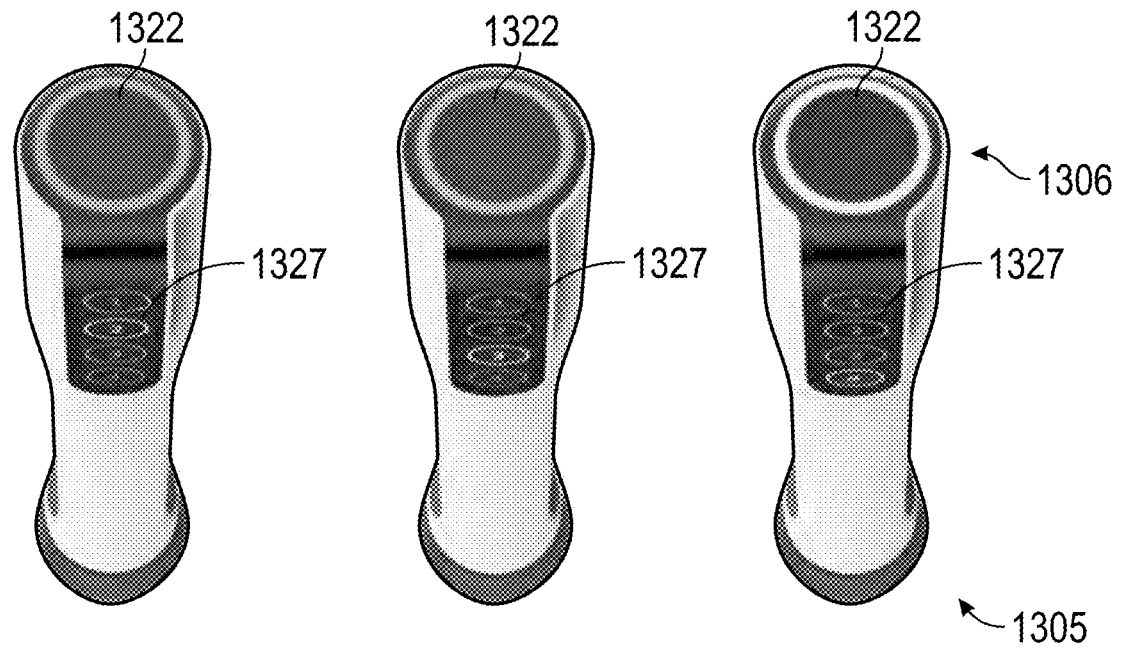
Figure 13G:
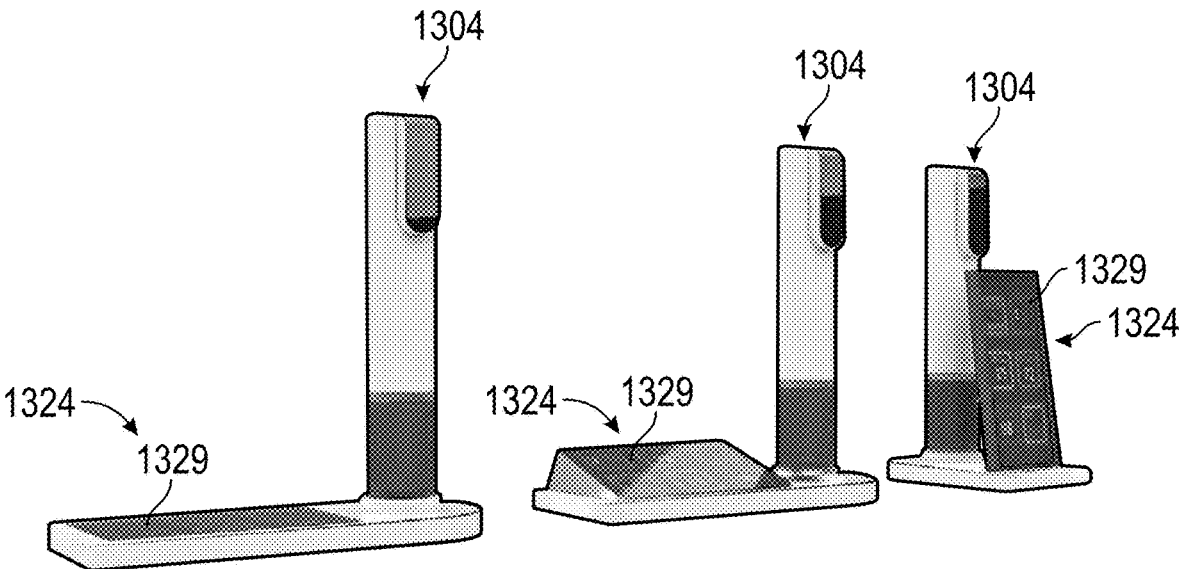
Figure 13H:
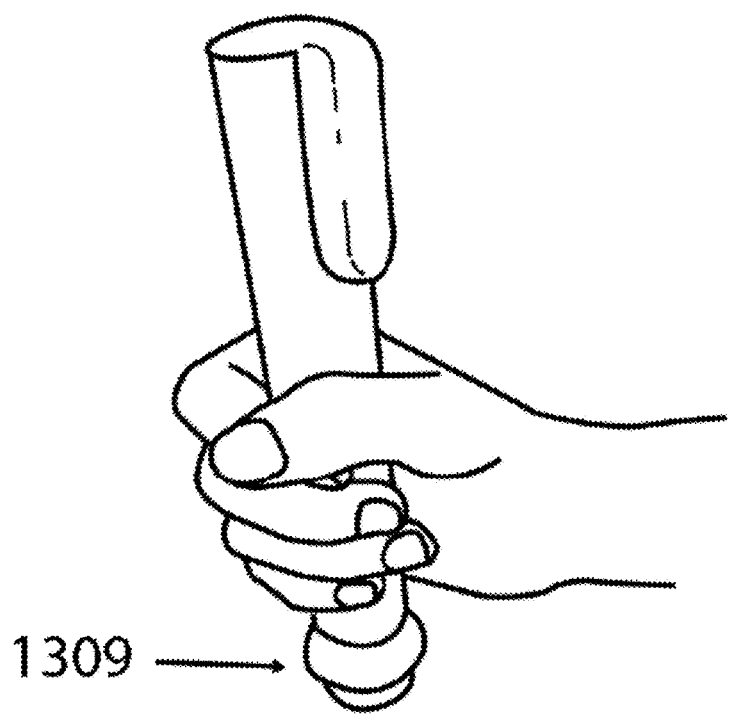
Figure 13I:
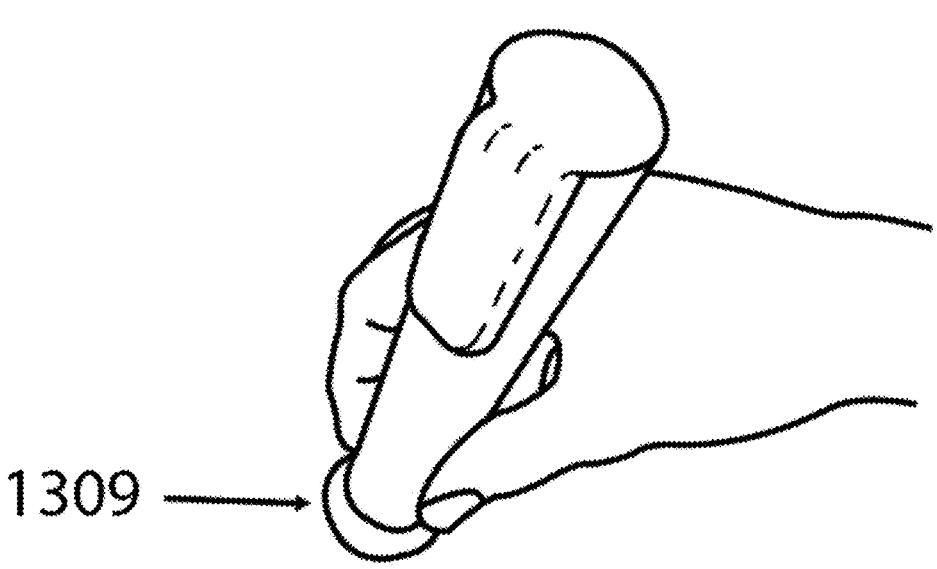

FIG. 13E illustrates the several examples of the first and second display 1322 and 1327 on the skin perfusion pressure determination device 1304. FIG. 13F illustrates embodiments of the skin perfusion pressure determination device 1304 with a first display 1322 and a second display 1327.

FIG. 13G illustrates the skin perfusion pressure determination device 1304 similar to the skin perfusion pressure determination device 1304 described with reference to FIGS. 13A and 13B except the skin perfusion pressure determination device 1304 shown in FIG. 13G is wireless. The wireless skin perfusion pressure determination device 1304 can be docked on a docking station 1324. The docking station 1324 can allow for data transfer and/or charging of the skin perfusion pressure determination device 1304. In some embodiments, the data transfer and/or charging can be conducted through a wireless contact connection or the device can be electrically connected through an electrical connector on the docking station 1324.

In some embodiments, the docking station 1324 can be a computer or other control unit. Data collected by the skin perfusion pressure determination device 1304 can be transferred to the computer or other electronic device for storage and/or processing.

The docking station 1324 can include a display 1329 that can be used to display information or data collected by the skin perfusion pressure determination device 1304 and/or provide controls or settings for the skin perfusion pressure determination device 1304. In some embodiments, the docking station 1324 can be used to calibrate the skin perfusion pressure determination device 1304. In some embodiments, the docking station 1324 provides a housing for storing the skin perfusion pressure determination device 1304. The skin perfusion pressure determination device 1304 can be docked into the docking station 1324 with the proximal or skin contacting end resting in the docking station as illustrated in FIG. 13G. In other embodiments, the skin perfusion pressure determination device 1304 can be docked into the docking station 1324 with the distal end resting in the docking station or in any other configuration.

Figure 13J:
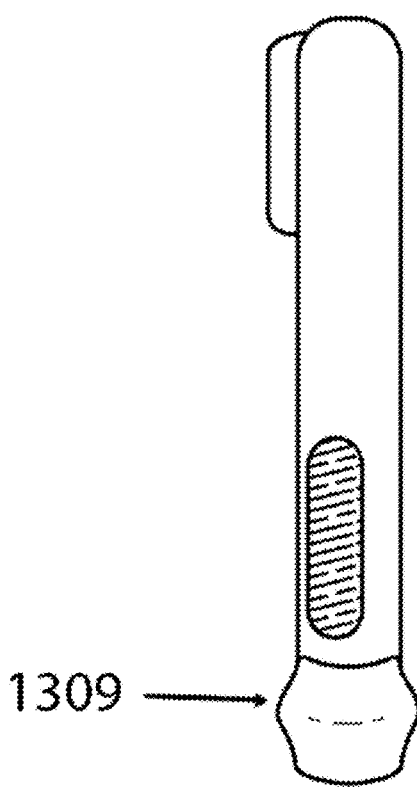
Figure 13K:
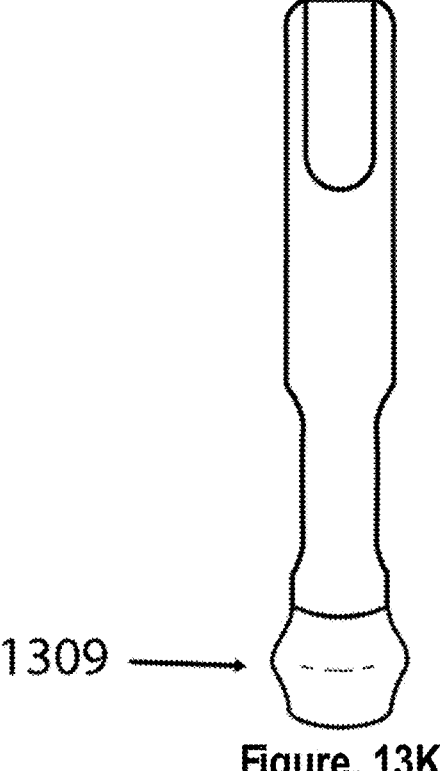

FIGS. 13H and 13I illustrate an embodiment of the skin perfusion pressure determination device 1304 held by a user to apply pressure to the skin to obtain a skin perfusion measurement 1304. FIGS. 13H-13I illustrate an embodiment of the skin perfusion pressure determination device 1304 being gripped by a user. As described herein, the shape of the device can lead the user to instinctively hold the devices in different ways. The skin perfusion pressure determination device can require careful and steady (non-shaking) control of the pressure and/or the direction of pressure application at a 90-degree angle to the target tissue area. In some embodiments, the grip portion of the device can drive hand orientation. The hand orientation can drive arm alignment. In some embodiments, the skin perfusion pressure determination device 1304 can be held in any orientation described herein, including the orientations suggested by the grip portions and shapes of the device described in other embodiments. For example, the palm grip shown in FIG. 10C, the pen grip shown in FIGS. 10E, 12C, and 13I, the barrel grip shown in FIGS. 11F-11G and 13H, and/or any other grip that allows the user to control the device can be used. The shape and size of the devices can require or encourage a different grip and arm alignment. In some embodiments, the different grip and/or arm alignment can change the degree of control over the steady application and/or removal of pressure on the target area. In some embodiments, the grip portion 1321 can guide and/or aid the user to correctly orient and hold the pen at the correct angle. FIG. 13J illustrates a side view of an embodiment of the skin perfusion pressure determination device 1304. FIG. 13K illustrates a front view of an embodiment of a skin perfusion pressure determination device 1304.

In some embodiments, the display can include a circumferential light guide illuminated by a LED. For example, a color or multiple colors can be used to guide the user through the procedure and use of the device. In some embodiments, the light guide can be any LED, arrangement of LEDs or screens, not necessarily circumferential, to guide the user through the procedure.

The skin perfusion pressure determination devices described herein can be powered by one or more power options. In some embodiments, the skin perfusion pressure determination device can be powered by metal contact points. Metal contact points can use contact points to transmit power to a battery within the device. Metal contact points can allow the skin perfusion pressure determination device to be flush with the charging device. Additionally, by removing openings or recess for charging, the metal contact point charging can maintain cleanliness of the device. In some embodiments, metal contact points can have the potential for conductivity to be affected by cleaning chemicals and the construction of the device can require more complicated molding. In some embodiments, the device can be powered during its operation by a internal battery and the battery can then be recharged and data can be transferred in/out using the metal connector points. In some cases, the battery can be removable and/or replaceable and can be changed instead of being recharged.

In some embodiments, the skin perfusion pressure determination devices described herein can be powered by USB charging. The battery of the skin perfusion pressure determination device can be charged using a USB cable connection. In some embodiments, the device can be powered during its operation by a internal battery and the battery can then be recharged and data can be transferred in/out using the USB connector. In some embodiments, the USB connection can create a space for bacteria, volatile organic compounds (VOCs), or other harmful components to be harbored at the connection point. In some embodiments, a fixed USB connector can be used to power the skin perfusion pressure determination device. The fixed USB can connect the skin perfusion pressure determination device to a power source. The fixed USB could be used without a battery to delivery power to the device. The fixed USB connector can be used to attach a cable in order to connect the skin perfusion pressure determination device to a power source. Therefore, the skin perfusion pressure determination device can only be used within the limited distance of the power source allowed by the cable. The design with the fixed USB connector and without an internal battery can require a power source or computer to always be connected while the skin perfusion pressure determination device is in use. In some embodiments, any design which does not use an internal battery, can require a power source or computer to always be connected while the skin perfusion pressure determination device is in use In some embodiments, wireless or induction charging can be used to charge the skin perfusion pressure determination device. The skin perfusion pressure determination device can be charged on a charging station or docking station similar to the docking stations discussed herein. The wireless or induction charging can provide a seamless housing for the skin perfusion pressure determination device since the housing does not have to include a recess or cord for charging. In some embodiments, the skin perfusion pressure determination device can have a removable battery. The removable battery could be switched out with a new battery when the old battery runs down. The opening in the device for receiving the battery can allow for bacteria, VOCs, or other harmful components to be harbored at the attachment point. In such cases, the opening that allows for the battery to be changed can be closed or sealed to prevent bacterial, VOCs, or other harmful components from entering the device.

In some embodiments, as described herein the skin perfusion pressure determination devices can transfer data collected by the sensors to a computer, control unit, or other device through various methods. In some embodiments, data can be transferred through metal contact points similar to the metal contact points used to power the device. In some embodiments, data can be wirelessly transferred from the skin perfusion pressure determination device to a computer, control unit, or other device. The data can be transferred over Bluetooth, zigbee, or other wireless technology. The wireless communication device can be embedded in the skin perfusion pressure determination device. In some embodiments, data can be transferred from the skin perfusion pressure determination device to computer, control unit, or other device by using a USB cable. The USB cable would limit the distance between the skin perfusion pressure determination device to computer, control unit, or other device. In some embodiments a contactless data transfer can be used. The data can be transferred from the skin perfusion pressure determination device to computer, control unit, or other device via a RF/NFC link. The contactless data transfer can have a limited distance. In some embodiments, a smaller amount of data can be transferred than with other methods. In some embodiments, data can be transferred from the skin perfusion pressure determination device to computer, control unit, or other device using infrared. Infrared data transfer can require line of sight between the two devices.

Various cables can be used to transfer data or charge the skin perfusion pressure determination device. A cable jacket can be formed from PVC or TPE (Thermoplastic Elastomer). In some embodiments, the cable can be shielded with aluminium foil or braided SPC with aluminium foil underneath. In some embodiments, the connection moulding of the cable can include overmoulded nylon, overmoulded TPE with an injection moulded cover, overmoulded PP, overmoulded nylon with injection moulded cover, or overmoulded nylon with injection moulded PP cover. In some embodiments, the connection strain relief of the cable can be nylon, TPE, or PP.

As described previously with reference to FIG. 4, the skin perfusion pressure determination devices described herein can be used to determine a skin perfusion pressure measurement. Such measurements may be used to aid the prediction of wound healing. As described herein to obtain a measurement of skin perfusion pressure, a clinician (or the patient themselves) presses the sensor module and/or the proximal end of the skin perfusion pressure determination device against the target area of a patient's body to occlude the blood vessels within the tissue below the target area. The amount of force is increased until the pulsatile component of the trace drops below a predetermined level or ceases to be evident. Once the trace drops below the predetermined level, the clinician continues to hold the sensor module in the skin perfusion pressure determination device against the target area to ensure that the pulsatile arterial blood flow has ceased in the tissue at the target area. The clinician begins to reduce the force applied to the sensor module in the skin perfusion pressure determination device slowly until the pressure module in the skin perfusion pressure determination device has been released completely and pulsatile arterial blood flow in the tissue at the target area is completely restored.

In some embodiments, it can be useful to incorporate an automatic or controlled force application or force withdrawal mechanism. This can assist the user in obtaining a measurement of skin perfusion pressure by controlling the amount of force applied to occlude the blood vessels within the tissue below the target area. Additionally, an automatic or controlled withdrawal of force can allow for a slow and measured release of pressure over the target area until the blood flow in the tissue at the target area is completely restored. In some embodiments, even with an automatic or controlled application or withdrawal of force, a user can still be required to keep their hand reasonably still and/or withdraw it slightly. In some embodiments, the control or withdrawal mechanism described herein can be used to assist the user and allow the force to be reduced in a more controlled way. For example, in some embodiments, if the user suddenly moves their hand (and the skin perfusion pressure determination device) towards or away the skin, they can overcome the control or withdrawal mechanism. The control or withdrawal mechanisms can be used to help the user to apply and/or withdraw the applied force slowly. The automatic or controlled withdrawal of force can allow for more accurate and repeatable measurements provided by the skin perfusion pressure determination device. Various mechanisms can be utilized to automate or control the force application of the skin perfusion pressure determination device.

FIGS. 14A-17C illustrate embodiments of withdrawal mechanisms for use with a skin perfusion pressure determination device.

In some embodiments, there are two different principles used to automate and control the application and/or withdrawal of force applied to the tissue area. In the first the user applies a force and, when the device detects that the pulse has stopped (i.e. the blood flow has been occluded), the device slowly releases the force applied to the skin. This release can be controlled using, for example, one or more of the withdrawal mechanisms described in FIGS. 14A-17C. In the second the user can control the force applied to the skin using a control mechanism. This force can be controlled using, for example, one or more of the control mechanisms described in FIGS. 18A-19B. The automated pressure application and/or withdrawal mechanisms described in the following paragraphs can be used in combination with and incorporated into any of the embodiments, of the skin perfusion pressure determination device incorporating a sensor module for obtaining a measurement of skin perfusion pressure as described herein, including but not limited to the embodiments described with reference to FIGS. 7A-13K.

In some embodiments, when using a withdrawal or control mechanism the user's hands provides as a minimum an end stop that the device presses against. However, in some embodiments, hand movements of the user, if they interfere with the operation of the device, can be (partially) compensated for. In some embodiments, the withdrawal or control mechanisms described herein can also be used with the integrated approaches shown in FIG. 1, where the band provides the end stop the device presses again to generate the force.

The skin perfusion pressure determination device can utilize various designs incorporating the sensors and signal processing elements into an elongate housing. The skin perfusion pressure determination device can include an elongate housing having a proximal end and a distal end similar to and include features of the elongate housing and skin perfusion pressure determination device described with reference to FIGS. 7A-13K. The elongate housing can include a sensor module provided within the elongate housing and/or the proximal end assembly configured to detect a pressure exerted on a target area and an amount of blood perfusion at the target area. The elongate housing can include a proximal end assembly configured to exert a pressure on the target area. The proximal end assembly can include a withdrawal mechanism to automatically control the pressure exerted on the target area by the proximal end assembly.

In some embodiments, a skin perfusion pressure can be determined by positioning a proximal end of a skin perfusion pressure determination device on a target area of patient. A force can be applied to the skin perfusion pressure determination device against the target area. The force or a pressure applied to the target area by the skin perfusion pressure determination device can be measured using a first sensor within the device. Blood perfusion in the target area beneath the proximal end can be measured using a second sensor within the device. After the device detects that blood flow has been occluded in the target area, the device can automatically withdraws the force applied to the target area at a controlled rate.

Figure 14A:
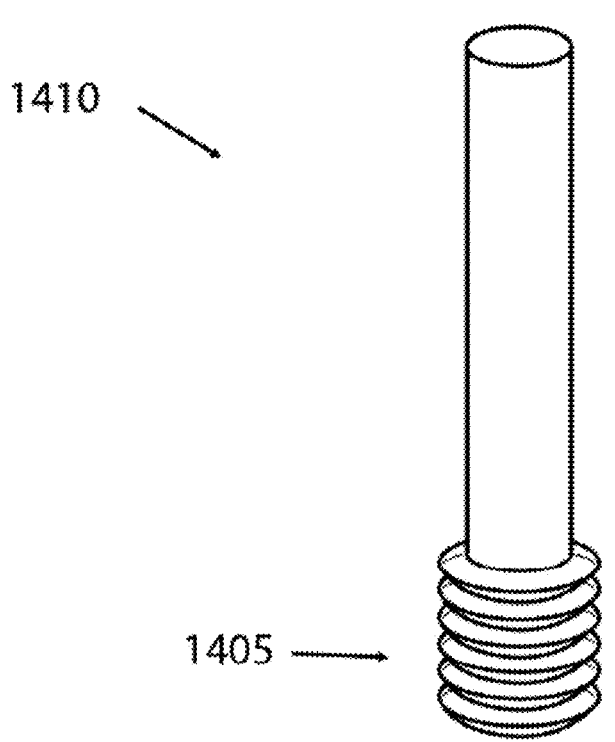
FIGS. 14A-14B illustrate an embodiment of a withdrawal mechanism with air bellows.
Figure 14B:
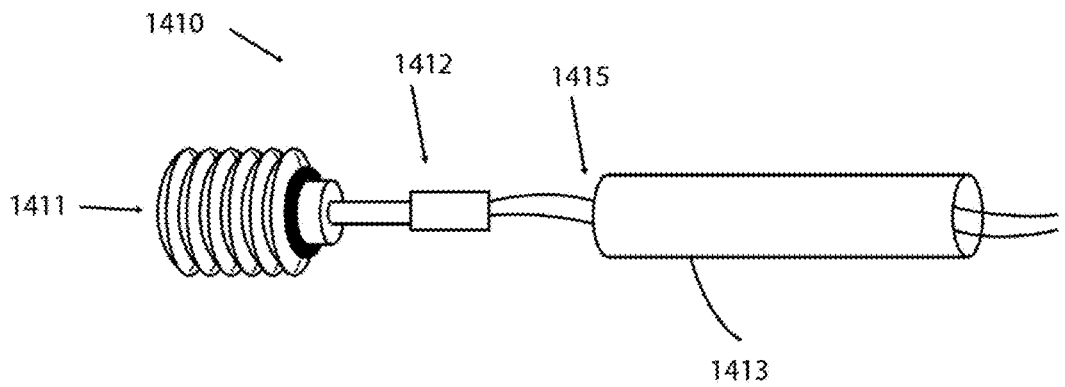

FIGS. 14A-14B illustrate an embodiment of a withdrawal mechanism with air bellows. In some embodiments, the air bellows device 1410 can be used with the elongate housing of the skin perfusion pressure determination device described herein. In some embodiments, the air bellows device 1410 can be provided within the elongate housing. In some embodiments, air bellows device 1410 can be integrated into the housing of the elongate housing, for example, in some embodiments, the air bellows device 1410 can be integrated with the components of the proximal end assembly described herein. In some embodiments, the air bellows device 1410 can be provided within the proximal end assembly of the skin perfusion pressure determination device described herein. The air bellows device 1410 can utilize the release of (trapped) air from a reservoir using a pulsed valve to reduce/control the force applied to the skin. The air bellows device 1410 can include bellows, a flexible air container, or air spring 1411 that can include a proximal end 1405 for contacting the target tissue area. The air bellows device can use a valve or control mechanism 1412. The valve or control mechanism 1412 can be positioned within a housing 1413 when in use. The bellows 1411 can be connected to a proximal end of the housing 1415. The valve or control mechanism 1412 can be used to release air from the bellows 1411 in a controlled manner. In some embodiments, the withdrawal mechanism includes the bellows device 1411 in fluid communication with the control valve 1412. The bellows device 1411 can contract when the proximal end assembly is in contact with the target area and force is applied from the proximal end assembly to the target area. The bellows are configured to expand when the control valve is opened allowing air to fill the bellows. In some embodiments, the expansion of the bellows can be due to the bellows itself or via a mechanism, for example, a spring can be included which expands the bellows when the valve is open.

For example, the valve or control mechanism can include an on/off valve, an on/off valve with flow restrictor, a proportional/analog valve, and/or other known valve control mechanisms. The on/off valve can be manually or electrically operated. An electrically operated on/off valve can utilize a control system to control the time the valve is opened. The electrically operated on/off valve can allow for pulse-width modulated control (length of on-time is varied) with frequency fixed. In some embodiments, the frequency can be varied with a fixed opening time. In some embodiments, the frequency and duty cycle can be varied.

The on/off valve with flow restrictor can utilize the same control systems as the on/off valve. The on/off valve with flow restrictor can additionally manually or electronically control the flow resistance of flow restrictor.

In some embodiments, the proportional/analog valve can be manually controlled and/or electronically controlled.

The air bellows device 1410 can be a self resetting mechanism. When the valve or control mechanism has released all pressure, the air bellows device 1410 has been reset. In some embodiments, the valve or control mechanism can be run with a preprogramed algorithm to open or pulse at a predetermined rate until the desired pressure is achieved. In some embodiments, the user can use the measured force and/or the measured pressure detected by the sensors in the skin perfusion pressure determination device to adjust the bellows or application of force from the bellows.

In some embodiments, the bellows can reduce the force in a more controlled way by letting air out after the perfusion has stopped or the blood flow in the target area is occluded. In some embodiments, the bellows can reduce the force applied to the target tissue area in the initial force application phase as the user presses the device into the target tissue area. If too large a force is detected, the valve could open up, release air and therefore reduce the force applied to the target tissue area, therefore reducing the risk of damage to the target tissue area.

Figure 15A:
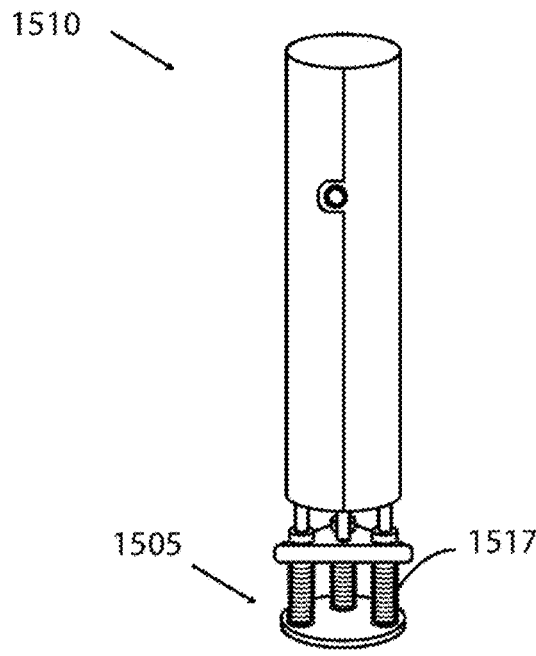
Figure 15B:
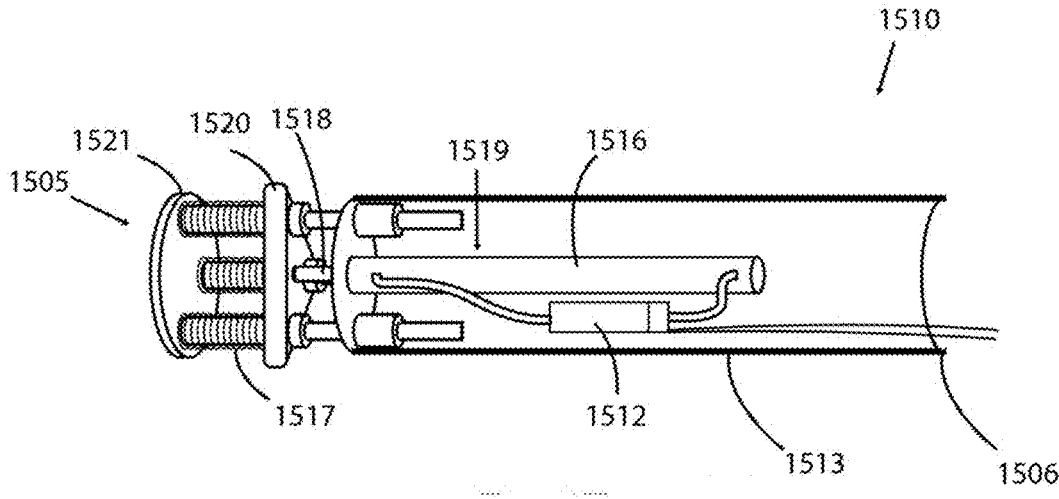

FIGS. 15A-15D illustrate an embodiment of a withdrawal mechanism with a fluid damper device 1510. In some embodiments, the fluid damper device 1510 can be provided within the elongate housing of the skin perfusion pressure determination device described herein. In some embodiments, the fluid damper device 1510 can be provided within the proximal end assembly of the skin perfusion pressure determination device described herein. The fluid damper device 1510 can include a spring 1517 that can include a proximal end 1505 for contacting the target tissue area. The fluid damper device 1510 can use a liquid filled piston 1516. The passage of the fluid out of one chamber of the piston 1516 can be controlled using a pulsed valve or control mechanism 1512. This allows for a controlled rate of release of the force from the skin. The fluid damper device 1510 includes a spring portion 1517 and a housing 1513 as illustrated in FIG. 15B. The control system can control the fluid flow from one chamber of the piston 1516 to the other. The compressed spring 1517 exerts a force on the intermediate platform 1520 and therefore the piston 1518. This causes fluid to flow from one end of the cylinder to the other, allowing the piston to move vertically upward or toward the distal end 1506 of the device and allowing the spring 1517 to expand and therefore reduces the force on the skin. In the initial state the piston is extended and the valve is closed. As the valve is closed, the piston is locked in this position. The user exerts a force onto the skin via the skin perfusion pressure determination device and compresses the spring 1517. The larger the applied force, the greater the compression of the spring. When the perfusion has stopped, the valve starts to allow passage of fluid form one chamber to the other. The spring via the piston pressurizes the fluid in one chamber which forces fluid to flow when the valve is open. This fluid flow in turn then allows the piston to move which expands the spring and reduces the force.

The liquid filled piston 1516 can include the proximal end and the distal end. The liquid filled piston comprises a first chamber at the distal end and a second chamber at the proximal end with the seal of the piston separating the two chambers. The liquid filled piston 1516 can be in fluid communication with a control valve 1512. The spring 1517 can include a proximal end and a distal end. The spring 1517 can be positioned proximal to the liquid filled piston 1516 and the intermediate platform 1520 positioned at the proximal end of the liquid filled piston 1516 and at the distal end of the spring 1517. In a first position, the piston is extended and the valve is closed and the piston is locked in this position because the valve is closed. The spring 1517 can be compressed by a force applied to the skin perfusion pressure determination device. The control valve can be opened to allow fluid to move from the first chamber to the second chamber of the fluid filled piston 1516 allowing the piston to move which expands the spring and reduces the force. The valve 1512 can be used to control the movement of the fluid (and piston) within the cylinder 1519. When the piston 1516 is in the extended position the base platform 1521 at the proximal end 1505 is applying a maximum pressure to the target tissue area. To release the pressure applied to the target tissue area, the valve 1512 can be opened and fluid can be allowed to move from the distal compartment to the proximal compartment (not shown) of the cylinder 1519. This will allow the piston and intermediate platform 1520 to move toward a distal end 1506 of the device, allowing the spring 1517 to expand and reducing the force applied to the skin.

As illustrated in FIGS. 15A-15D, the spring portion 1517 can include one or more springs connected to a base platform 1521 and an intermediate platform 1520. This spring portion 1517 can allow for better control and more even application of the force to the tissue area. For example, small vibrations of the hand are less likely to cause a large change in force applied to the tissue area.

The valve 1512 can be used to control the movement of fluid in the system in a controlled manner. For example, the valve or control mechanism can include an on/off valve, an on/off valve with flow restrictor, a proportional/analog valve, and/or other known valve control mechanisms. The on/off valve can be manually or electrically operated. An electrically operated on/off valve can utilize a control system to control the time the valve is opened. The electrically operated on/off valve can allow for pulse-width modulated control (length of on-time is varied) with frequency fixed. In some embodiments, the frequency can be varied with a fixed opening time. In some embodiments, the frequency and duty cycle can be varied.

The on/off valve with flow restrictor can utilize the same control systems as the on/off valve. The on/off valve with flow restrictor can additionally manually or electronically control the flow resistance of flow restrictor.

In some embodiments, the proportional/analog valve can be manually controlled and/or electronically controlled.

FIGS. 16A-16D illustrate an embodiment of a withdrawal mechanism with a magnetic brake device 1610. In some embodiments, the magnetic brake device can be an electromagnetic clutch or electromagnetic brake. In some embodiments, the magnetic brake device 1610 can be provided within the elongate housing of the skin perfusion pressure determination device described herein. In some embodiments, the magnetic brake device 1610 can be provided within the proximal end assembly of the skin perfusion pressure determination device described herein. The magnetic brake device 1610 can include a spring 1617 that can include a proximal end 1605 for contacting the target tissue area. The magnetic brake device 1610 can use a magnetic clutch 1641 and a ratchet arm 1643 to hold the proximal end 1605 in place and apply the force to the target tissue area. The magnetic clutch 1641 can include a wheel with teeth 1642 that interacts with teeth 1644 of the arm 1643. Then, when required, the magnetic clutch 1641 can slowly release the force applied to the skin by gradually allowing two parts of the mechanism to slip relative to each other. As the magnetic clutch 1641 slips, the gear wheel 1642 can rotate which in turn allows the arm 1643 to move. The movement of the arm 1643 can allow the spring 1617 to expand, thereby reducing the force applied to the tissue. In some embodiments, the proximal end 1605 is not moved but the spring is expanded which reduces the force which the spring exerts on the proximal end and therefore also the force which the proximal end exerts on the spring.

Figure 16A:
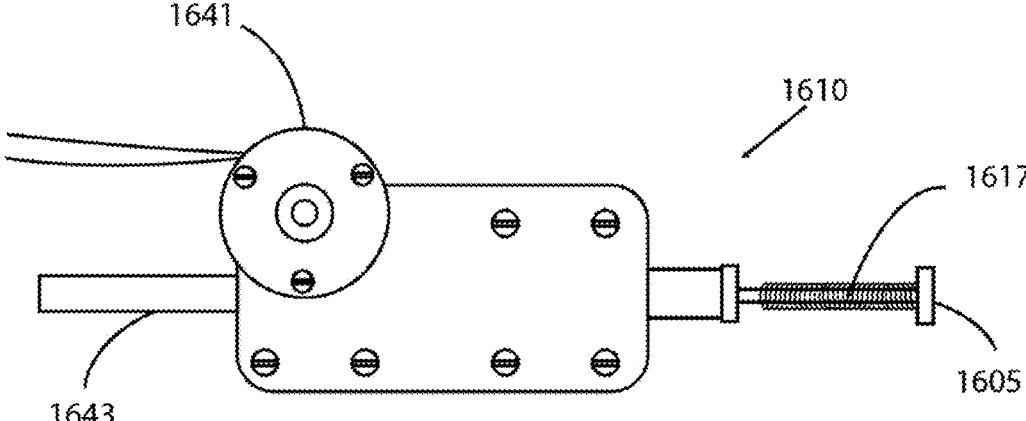
FIGS. 16A-16D illustrate an embodiment of a withdrawal mechanism with a magnetic brake device
Figure 16B:
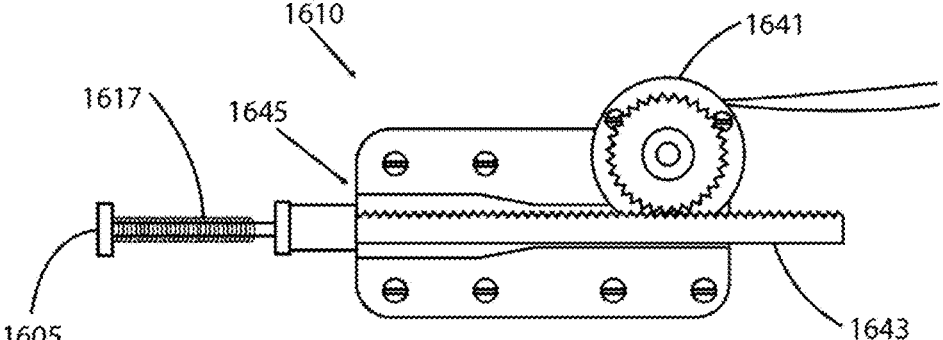
Figure 16C:
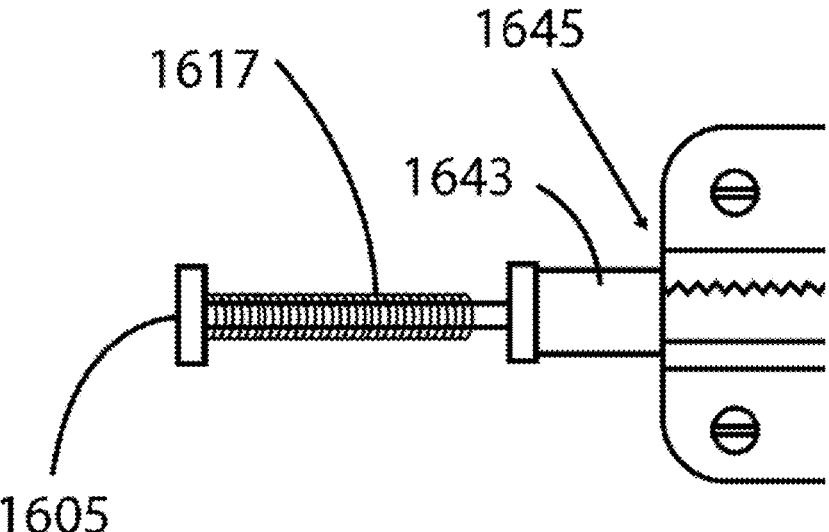
Figure 16D:
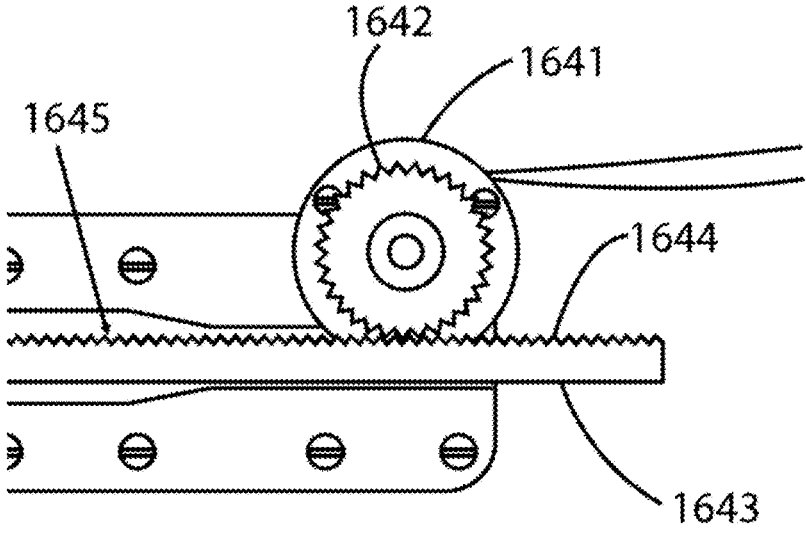

In some embodiments, the arm 1642 can move through a channel or guide 1645 as shown in FIG. 16B-16D to provide stability and guide the movement of the arm. The withdrawal mechanism can include the magnetic brake device 1610 including the magnetic clutch 1641 with a gear with teeth. The spring 1617 can be positioned at a proximal end of the device. The ratchet arm 1643 with teeth can be positioned distal to the spring 1617 and can exert a pressure on the spring 1617 in a first position. The teeth of the ratchet arm can be in communication with the teeth of the gear on the magnetic clutch 1641. The magnetic brake device 1610 can allow for the gear to turn in response to a magnetic field. When the gear is allowed to turn, the ratchet arm can apply a torque to turn the gear and the gear can move the ratchet arm 1643 toward the distal end of the elongate housing releasing the pressure on the spring 1617. Although FIGS. 16A-16D illustrate a rectangular shaped housing, the magnetic brake device 1610 can be any shape or size necessary to fit in the skin perfusion pressure determination device systems similar to the devices described herein.

A magnetic field can be applied to control the magnetic brake. A current can be applied through the magnetic brake with different voltages or different currents across the brake. A wide range power supply and control systems can be used to apply the current. The magnetic brake device can have an on/off control that can be manually or electrically operated. The electrically operated on/off control can deactivate the magnetic brake for brief periods of time by electronic signals (pulses). In some embodiments, the electrically operated on/off control can use a pulse-width modulated control (length of on-time is varied) with a frequency fixed. In some embodiments, the electrically operated on/off control can vary the frequency with a fixed opening time. In some embodiments, the electrically operated on/off control can vary frequency and duty cycle. In some embodiments, the magnetic brake can have a proportional/analog control that can be manually released and/or electronically controlled. The proportional/analog control that can be electronically controlled where friction is changed in an analogue manner by applying different voltage levels or passing different current levels through the coil in the magnetic brake.

Figure 17A:
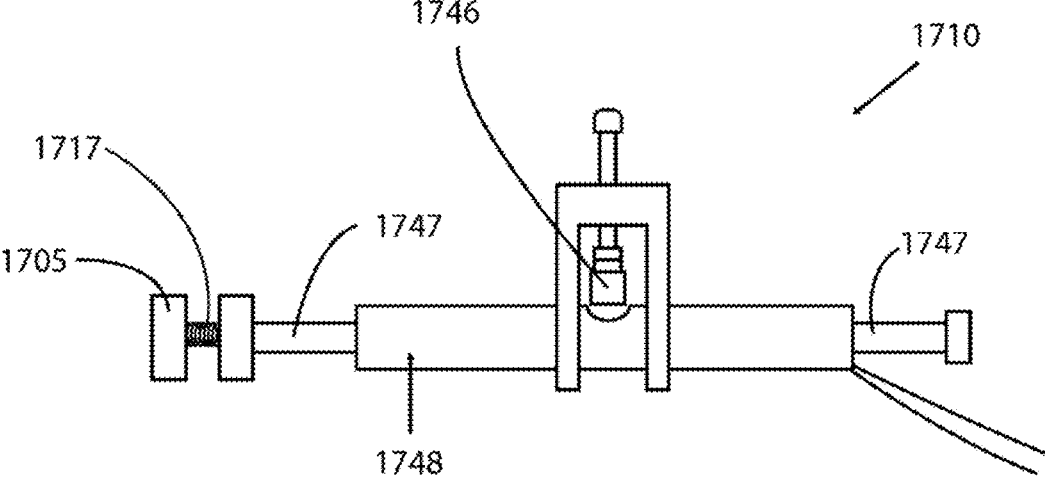
FIGS. 17A-17C illustrate an embodiment of a withdrawal mechanism with a magneto-rheological fluid device.
Figure 17B:
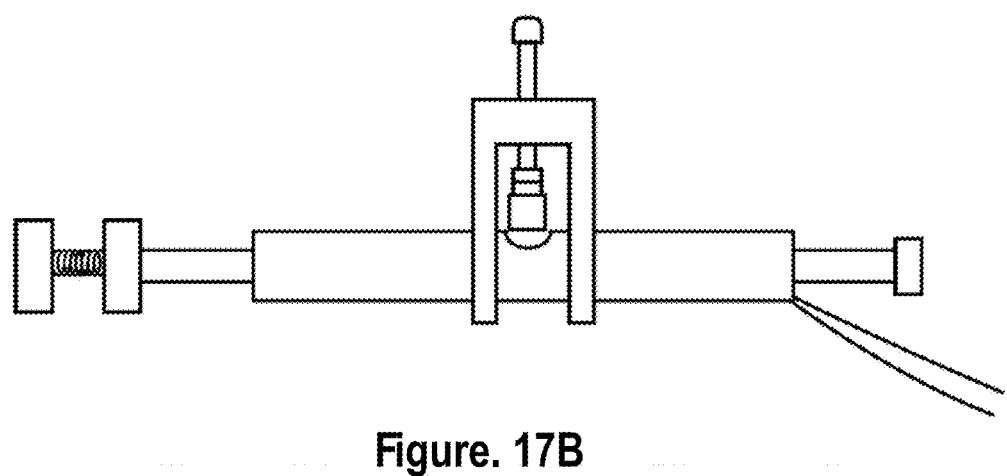
Figure 17C:
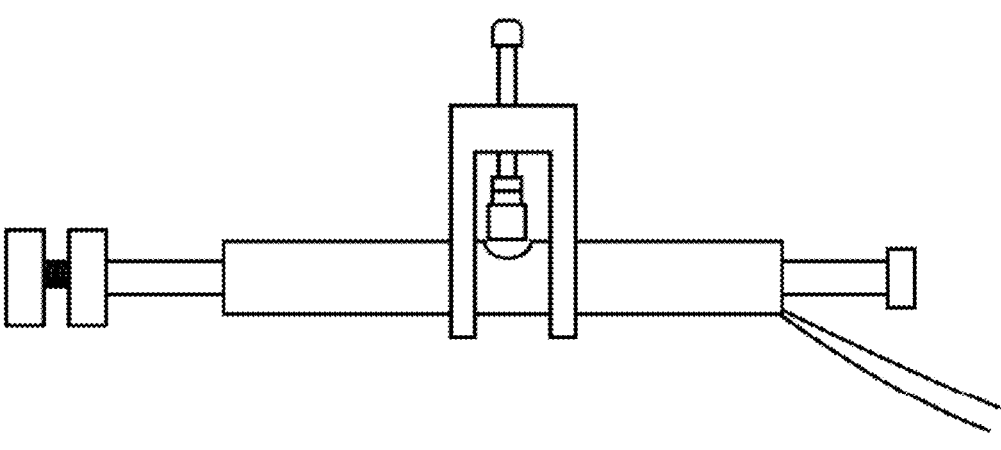

FIGS. 17A-17C illustrate an embodiment of a withdrawal mechanism with a magneto-rheological fluid device 1710. In some embodiments, the magneto-rheological fluid device 1710 can be provided within the elongate housing of the skin perfusion pressure determination device described herein. In some embodiments, the magneto-rheological fluid device 1710 can be provided within the proximal end assembly of the skin perfusion pressure determination device described herein. The magneto-rheological fluid device 1710 uses an adjustment of the viscosity of a magnetorheological fluid to reduce the force applied to the skin. The magneto-rheological fluid device 1710 illustrated in FIGS. 17A-17C uses two syringes or housings or reservoir 1748 with plungers 1747 with magneto-rheological fluid inside the syringe housing. A magnet (e.g., electromagnet) 1746 can be used to apply a magnetic field to the magneto-rheological fluid which in turn adjusts the viscosity of the fluid. By controlling the viscosity of the fluid, a user can control how the fluid flows from one syringe to the other.

The magneto-rheological fluid device system controls the flow of a magneto-rheological fluid within the syringe system. In some embodiments, the reservoir can include two syringes or housings 1748 connected by an orifice. Each chamber of the syringes or housings 1748 can receive a plunger which can move within the chamber. The magneto-rheological fluid device system controls the flow of a magneto-rheological fluid within the reservoir by controlling the viscosity of the fluid as it flows through an orifice in the housings and thereby allowing the plungers to move within the reservoir. Once the viscosity of the fluid is such that it can flow through an orifice, the spring can be allowed to expand and exert a force on the plungers to move the plungers and fluid within the housings. The viscosity of the fluid is adjusted by changing the magnetic field in the region of the orifice. The magnetic field can be created using and controlled by one or more permanent magnets and/or a coil wound around the reservoir and/or orifice. The movement of the one or more permanent magnets can be controlled manually including, but not limited to, changing the distance between the magnet and container/orifice, changing orientation, bringing in additional magnet(s) to increase the field, and/or bringing in additional magnet(s) to decrease/cancel field.

In some embodiments, a system can be used which is analogous to the fluid filled cylinder described herein with reference to FIGS. 15A-15D. The cylinder can be filled with the magneto-rheological fluid. In such embodiments, in place of the valve used in the embodiments described with reference to FIGS. 15A-15D, a magnet or electromagnet can be used to apply a magnetic field over a section of the tube linking the two cylinder chambers. The mode of operation is exactly the same as described above, except that the magnetic flied instead of pulsing the valve is used to control the movement of fluid in the cylinder.

The withdrawal mechanism 1710 can include a magneto-rheological fluid device with a magneto-rheological fluid that can change viscosity in response to a change in a magnetic field applied to the magneto-rheological fluid. The reservoir 1748 can include a first plunger 1747 on the proximal end of the reservoir 1748, a second plunger 1747 on the distal end of the reservoir 1738. The first plunger 1748 and the second plunger 1748 can move within the reservoir in a proximal to distal direction and/or a distal to proximal direction. In some embodiments, the reservoir can consist of two chambers which are linked by pipe or orifice, for example, with the magnetic field being applied to the pipe or orifice. One plunger would be in one chamber, the other plunger would be in the second chamber. The magneto-rheological fluid can be contained in the reservoir between the first plunger and the second plunger. The spring 1717 can be in communication with a proximal end of the first plunger. FIG. 17B illustrates the spring 1717 in a compressed position. FIG. 17C illustrate the spring 1717 in an extended position.

The magnet and/or a coil wrapped around the reservoir and/or orifice containing the magneto-rheological fluid 1746 can generate a magnetic field. The first and second plunger 1747 can have a first proximal position including the first plunger extended from the proximal end of the reservoir and the second plunger inserted into the reservoir. The viscosity of the magneto-rheological fluid can prevent movement of the plungers within the reservoir. The magnetic field can change the viscosity of the magneto-rheological fluid and can allow the magneto-rheological fluid to move within the reservoir. The spring can then expand and move the first plunger to a second distal position which can move the fluid from the proximal chamber to the distal chamber. The second distal position can include the first plunger inserted within the reservoir and the second plunger extending from the distal end of the reservoir. In some embodiments, the movement of the one or more permanent magnets can be electrically operated. Electronically controlled mechanisms can be used such as, but not limited to, an electromechanical actuator (e.g. motor, solenoid or other actuators) to change distance between magnet and container/orifice, change orientation, bring in additional magnet(s) to increase field, and/or bring in additional magnet(s) to decrease/cancel field.

In some embodiments, the coil wound around the reservoir and/or orifice containing the magneto-rheological fluid can be electronically controlled by passing a current through the coil to generate the magnetic field. An on/off control can be used to apply the field for certain periods of time. The on/off control can utilize a pulse-width modulated control (current on-time is varied) with frequency fixed, varied frequency with a fixed current on-time, and/or frequency and duty cycle can be varied. Electronic proportional control can also be used. The electronic proportional control can change the magnitude of current in an analogue manner by applying different voltage levels or passing different current levels through the coil.

FIGS. 18A-19B illustrate embodiments of control mechanisms for use with a skin perfusion pressure determination device. The control mechanisms can be used for the application and/or withdrawal of force on the tissue at the target area. The control mechanism can control the force applied to the skin by using a pump driven device (shown in FIG. 18A-18B) or a motor driven device (shown in FIGS. 19A-19B). The skin perfusion pressure determination device can utilize various designs incorporating the sensors and signal processing elements into an elongate housing. The skin perfusion pressure determination device can include an elongate housing having a proximal end and a distal end similar to and including features of the elongate housing and skin perfusion pressure determination device described with reference to FIGS. 7A-13K. The elongate housing can include a proximal end and a distal end. The elongate housing can include a sensor module provided within the housing and/or the proximal end assembly. The sensor module can detect a pressure exerted on a target area and an amount of blood perfusion at the target area. The elongate housing can include a proximal end assembly similar to the proximal end assembly described with reference to FIGS. 7-8. The proximal end assembly can include a control mechanism configured to automatically control the pressure exerted on the target area by the sensor module.

In some embodiments, a method of determining skin perfusion pressure can be used as described herein. The skin perfusion pressure can be determined by positioning a proximal end of a skin perfusion pressure determination device on a target area of patient. A force can be applied to the skin perfusion pressure determination device against the target area. The force or a pressure applied to the target area by the skin perfusion pressure determination device can be measured using a first sensor within the device. The blood perfusion in the target area beneath the proximal end can be measured using a second sensor within the device. The device can control the application and/or withdrawal of force by the skin perfusion pressure determination device against the target area.

Figure 18A:
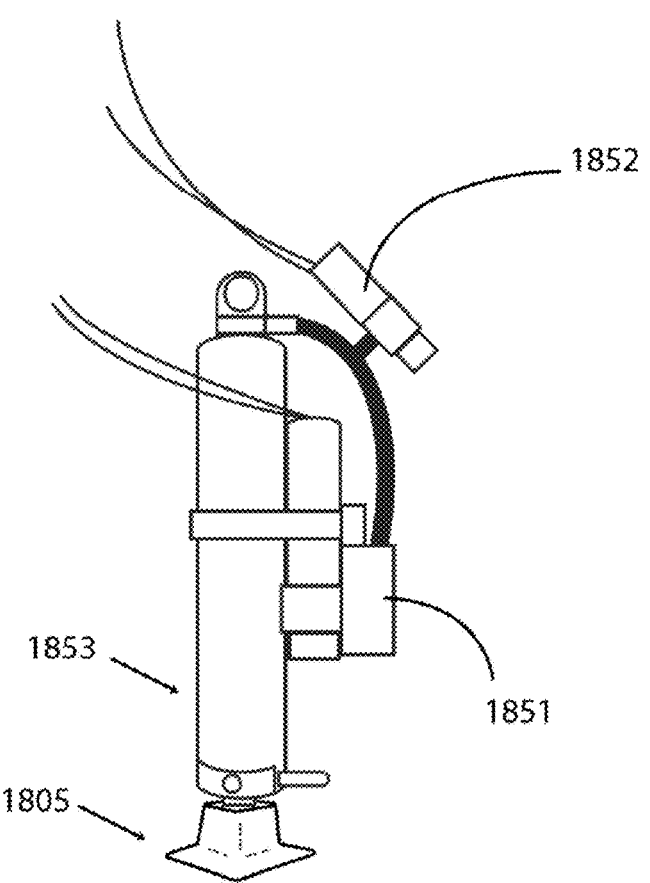
FIGS. 18A-18B illustrate an embodiment of a pump-driven device for use with a skin perfusion pressure determination device.
Figure 18B:
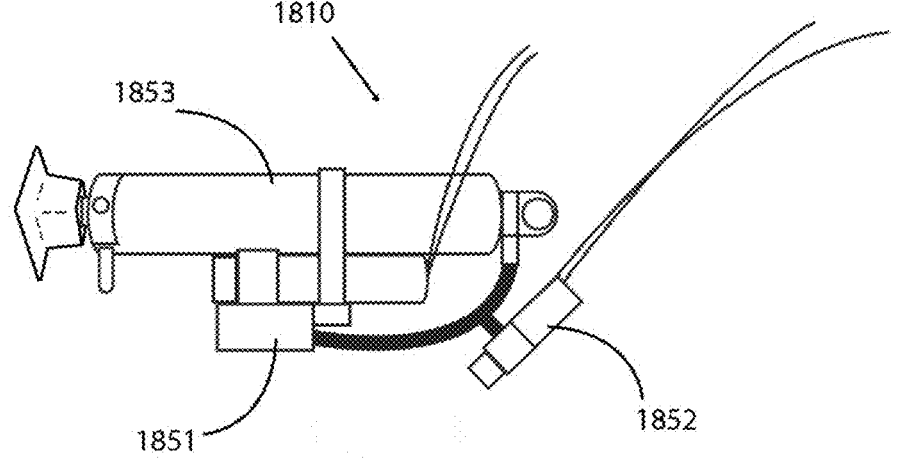

FIGS. 18A-18B illustrate an embodiment of a pump-driven device 1810 for use with a skin perfusion pressure determination device. The pump-driven device 1810 can use a pump 1851 and a valve 1852 to pump air into a reservoir 1853 and release air from the reservoir 1853, respectively. The pressure in the reservoir can be adjusted which in turn adjusts the force applied to the target tissue area by the skin perfusion pressure determination device. The pump-driven device 1810 controls the force applied to the target tissue area by controlling the pressure in the reservoir 1853. The pressure can be controlled by the interplay of the pump 1851 which pumps air into the system and the valve 1852 which lets air out of the system. The pump driven device can include the reservoir 1853 and the pump 1851 in fluid communication with the control valve 1852. The pump 1851 can pump air into the reservoir 1853 or allow air to escape from the reservoir 1853. The control valve 1852 can control the amount of air that fills or escapes the reservoir 1853. A rod (not shown) can move within the reservoir 1853 and extend from the proximal end of the reservoir 1853. The pump driven device 1810 can include a first position wherein the reservoir is filled with air thereby causing the rod to extend proximally from the reservoir to allow the skin perfusion pressure determination device to exert pressure on the target area. The pump driven device 1810 can include a second position wherein the rod is contained within the reservoir as illustrated in FIG. 18A-18B.

In some embodiments, the pump and the valve can work with any working fluid. The use of air can be convenient, as the atmosphere can be used as an unlimited reservoir. A tank of the working fluid can be used to pump the working fluid out of and then release it back into. Any other gases or liquids can be used. In the case of an incompressible liquid, an additional spring can be used between the piston and the component which applies the force to the target area as the extension/position of the piston would be controlled rather than the pressure inside it.

The pump 1851 can incorporate several features that can control the force applied to the target tissue area. The pump speed can be electronically controlled. Analogue/proportional control can be used by controlling the magnitude of voltage applied to pump and/or the frequency of the control signal applied to pump. An on/off valve can be used to control the pump speed electronically. In some embodiments, the on/off valve can control the pump speed by controlling open time with a control system, using pulse-width modulated control (length of on-time is varied) with frequency fixed, varying frequency with a fixed opening time, varying frequency and duty cycle.

The valve 1852 can incorporate several features that can control the force applied to the target tissue area. The valve 1852 can use an on/off valve that is manually or electrically operated. In some embodiments, the on/off valve can be electrically operated by controlling open time with a control system, using pulse-width modulated control (length of on-time is varied) with frequency fixed, varying frequency with a fixed opening time, varying frequency and duty cycle. An on/off valve with a flow restrictor can be used and the on/off valve with a flow restrictor can utilize the same control systems as the on/off valve described above. The on/off valve with flow restrictor can additionally manually or electronically control the flow resistance of flow restrictor. In some embodiments, a proportional/analog valve can be used that can be manually controlled and/or electronically controlled.

Figure 19A:
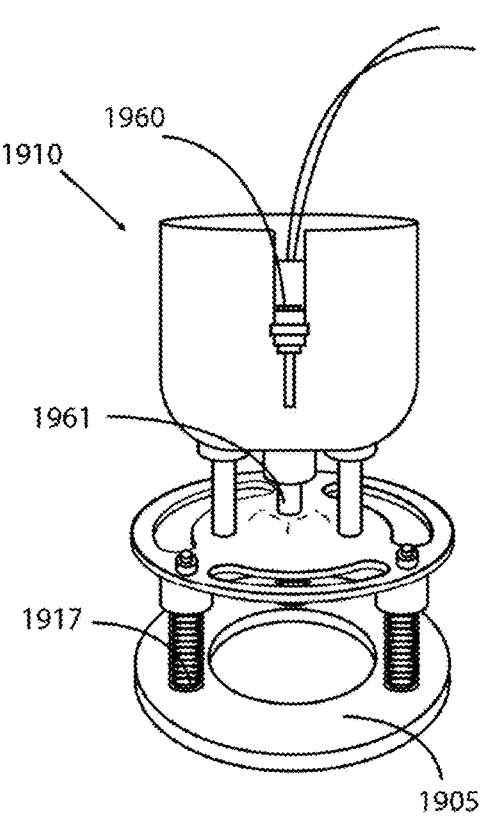
FIG. 19A-19B illustrates an embodiment of a motor driven device for use with a skin perfusion pressure determination device.
Figure 19B:
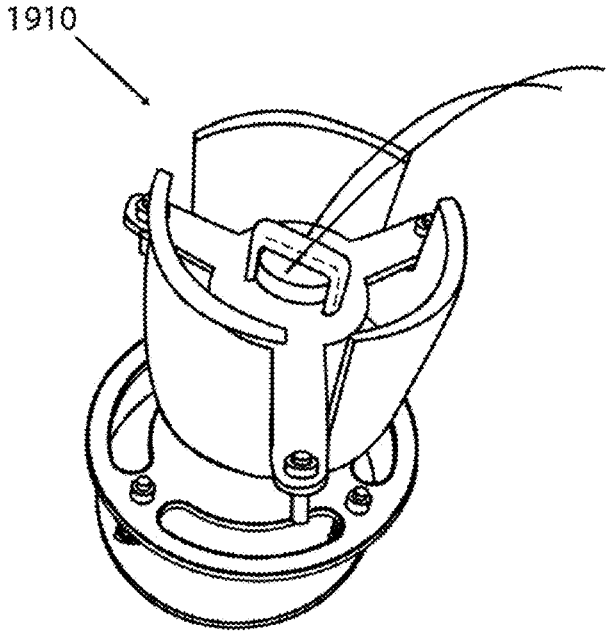

FIG. 19A-19B illustrate an embodiment of a motor driven device 1910 for use with a skin perfusion pressure determination device. The motor driven device 1910 can use a motor 1960 coupled to lead-screw 1961 and a spring 1917 to adjust the force applied to the target tissue area by the proximal end 1905 of the skin perfusion pressure determination device. The motor driven device 1910 can control the force applied to the target tissue area by compressing or extending a spring 1917 using a motor 1960. A wide range of motors could be used including, for example, DC motors, AC motors, piezo motors, or other motors. In some embodiments, electromechanical actuators can be used in place of a motor, for example, a solenoid, an electric linear actuator/cylinder, or other electromechanical actuators. In some embodiments, the displacement could also be adjusted manually. The motor driven device 1910 can include a motor 1916 and a lead screw 1961 coupled to the motor 1916. The lead screw 1961 can within the proximal end assembly in a proximal to distal and/or distal to proximal direction. The spring 1917 can be coupled to the lead screw 1916. The spring 1917 can move within the proximal end assembly in a proximal to distal and/or distal to proximal direction and can adjust the force applied to the target tissue area by the proximal end of the proximal end assembly. The lead-screw is configured to extend or move in a proximal direction exerting a force on the spring which exerts a force on the target tissue area. The lead-screw can retract or move in a distal direction releasing the force exerted on the spring.

Figure 20C:
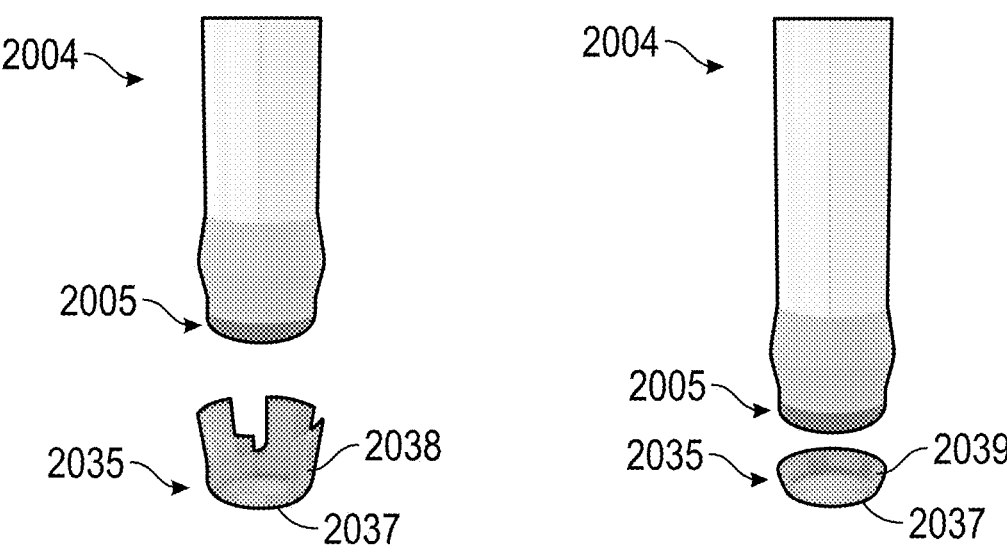
Figure 20C:
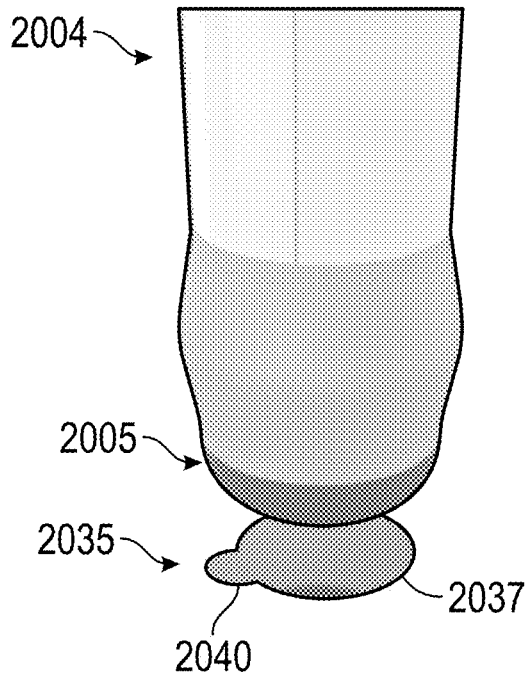

FIGS. 20A-20C illustrate protective cover 2035 that can be placed over the proximal tissue contacting end 2005 of a skin perfusion pressure determination device 2004, which can be any of the devices described herein. The protective cover 2035 can be a thin film or material for covering the tissue contacting end 2005 of the device 2004. The protective cover 2035 can be helpful for sterilizing or cleaning the device between uses. For example, the skin perfusion pressure determination device 2004 with a first protective cover can be applied to a first tissue area for a first measurement. Then the skin perfusion pressure determination device 2004 can be removed from the first tissue area and the protective cover 2035 can be removed and discarded. A second protective cover can be applied to the skin perfusion pressure determination device 2004. Then the skin perfusion pressure determination device 2004 with the second protective cover can be applied to a second tissue area for a second measurement.

FIGS. 20A-20C illustrate embodiments of protective covers with a central portion 2037. FIG. 20A illustrates a protective cover 2035 with extended pieces of material 2038 extending from the central portion 2037. The extended pieces of material 2038 can wrap around the proximal end 2005 of the skin perfusion pressure determination device 2004. FIG. 20B illustrates a protective cover 2035 with a lip 2039 extending from the central portion 2037. The lip 2039 can wrap around the proximal end 2005 of the skin perfusion pressure determination device 2004. FIG. 20C illustrates a protective cover 2035 with a tab 2040 extending from the central portion 2037. The tab 2040 can wrap around the proximal end 2005 of the skin perfusion pressure determination device 2004 and can be used to place or remove the protective cover 2035 from the proximal end 2005. In some embodiments, the protective cover can be a clip-on cup and/or adhesive patch.

In some embodiments, the protective cover 2035 can be formed from a material that is biocompatible or capable of contacting the skin and that does not interfere with the measurement. For example, the protective cover 2035 can be optically transparent so as not to interfere with the sensor readings. The protective cover 2035 does not need to be completely transparent as long as the sensors in the skin perfusion pressure determination device can detect the required wavelengths. In some embodiments the protective cover can be formed from a thermoplastic polymers such as polylactic acid (PLA) or polypropylene (PP). In some embodiments, the protective cover can be made of glass materials, for example, a high strength glass material such corning or gorilla glass. In some embodiments, the protective cover can be made of any material including the materials described herein with reference to the proximal end of the skin perfusion pressure determination device.

Figure 21A:
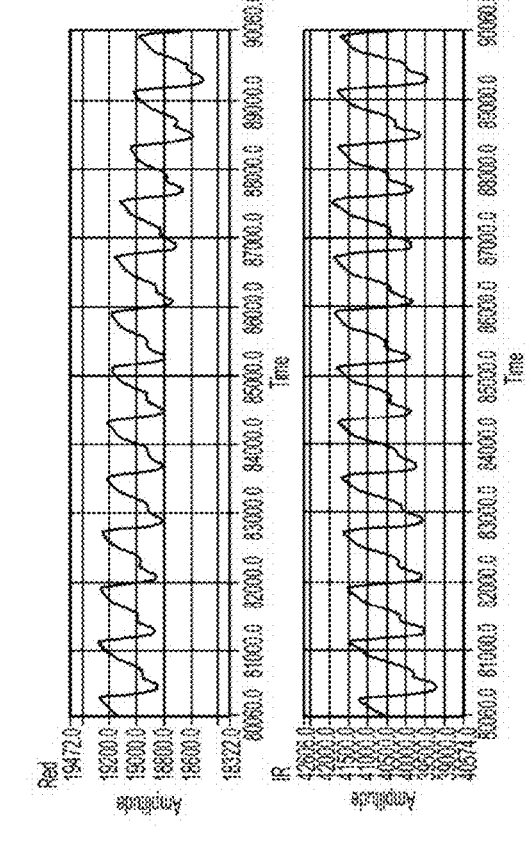
FIG. 21A illustrates the results of sensor readings from a skin perfusion pressure determination device with no protective cover (left side) and with a protective cover made from PLA (right side)
Figure 21A:
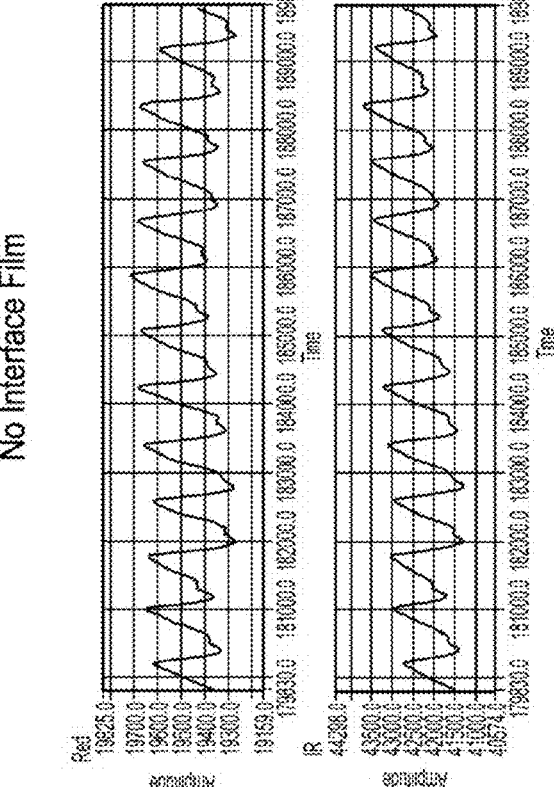

FIG. 21A illustrates the results of sensor readings from a skin perfusion pressure determination device with no protective cover (left side) and with a protective cover made from PLA (right side). As illustrated in FIG. 21A the protective cover made from PLA does not interfere with the sensors or measurement ability of the skin perfusion pressure determination device.

Figure 21B:
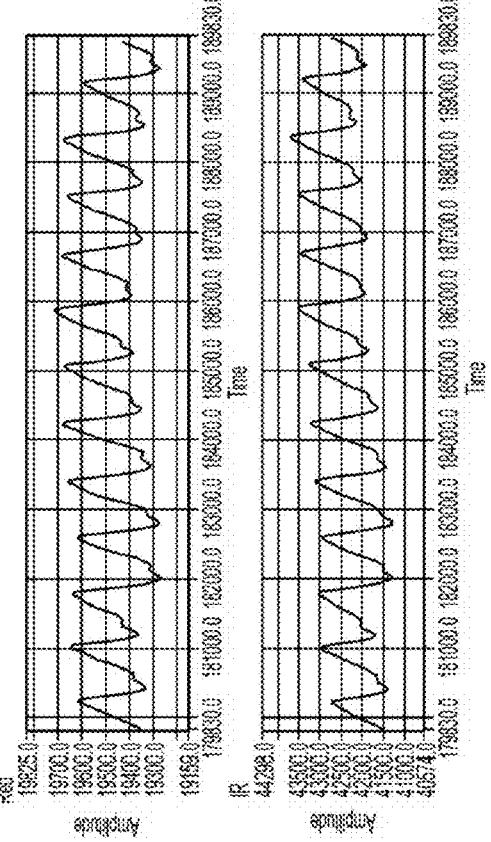
FIG. 21B illustrates the results of sensor readings from a skin perfusion pressure determination device with no protective cover (left side) and with a protective cover made from PP (right side)

FIG. 21B illustrates the results of sensor readings from a skin perfusion pressure determination device with no protective cover (left side) and with a protective cover made from PP (right side). As illustrated in FIG. 21B the protective cover made from PP does not interfere with the sensors or measurement ability of the skin perfusion pressure determination device.

Figure 22:
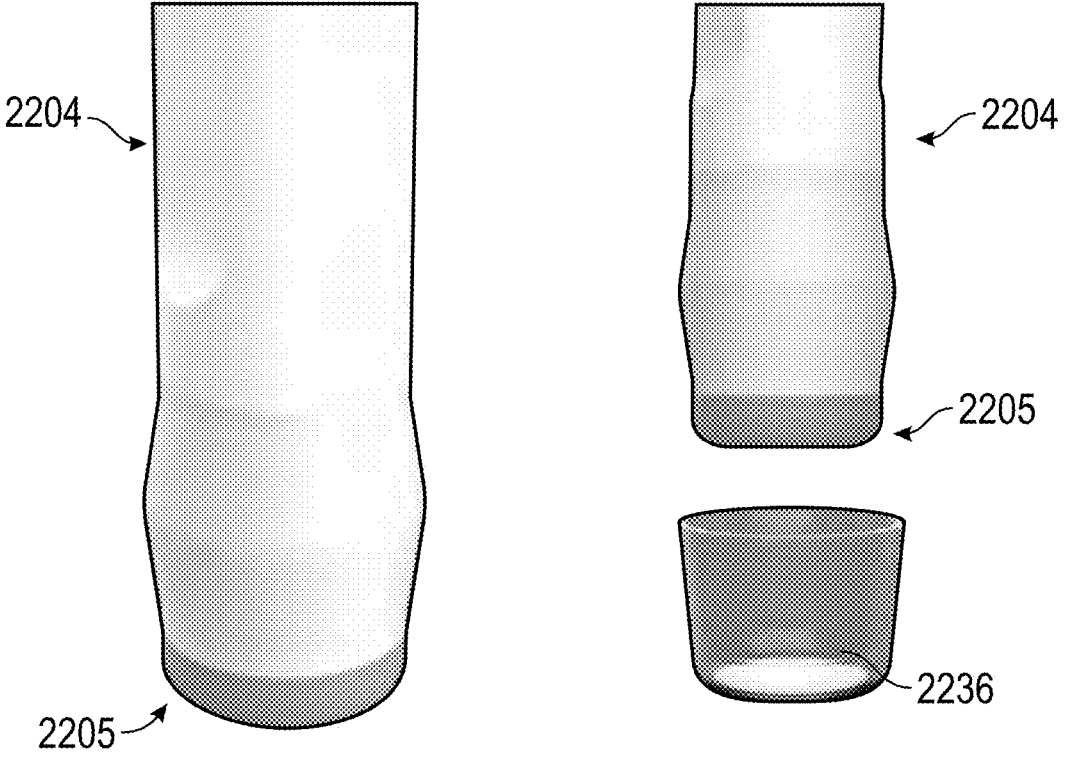
FIG. 22 illustrates an embodiment of a skin perfusion pressure determination device.

FIG. 22 illustrates a skin perfusion pressure determination device 2204 with a proximal tissue contacting end 2205. A cover 2236 can be used to cover the tissue contacting end 2205 of the skin perfusion pressure determination device 2204 when the skin perfusion pressure determination device 2204 is stored. The cover 2236 can protect the tissue contacting end 2205 of the skin perfusion pressure determination device 2204 and help maintain the cleanliness of the device.

Figure 23A:
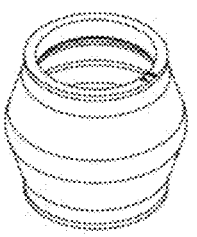
FIGS. 23A-23C illustrate embodiments of bellows designs for use with the skin perfusion pressure determination device.
Figure 23A:
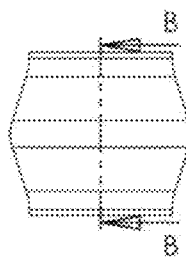
Figure 23A:
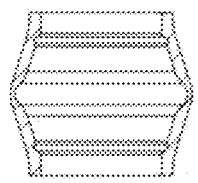
Figure 23B:
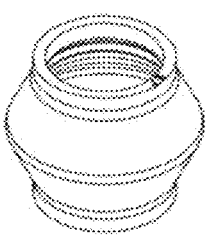
Figure 23B:
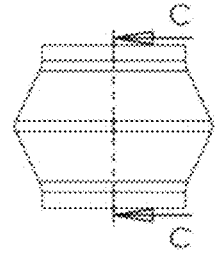
Figure 23B:
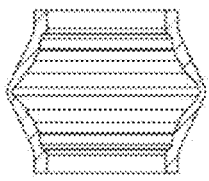
Figure 23C:
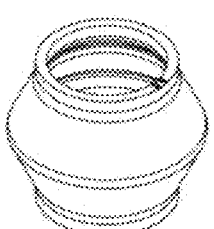
Figure 23C:
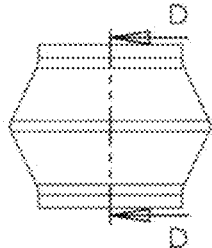
Figure 23C:
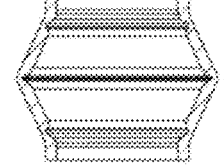

FIGS. 23A-23C illustrate embodiments of bellows designs for use with any of the skin perfusion pressure determination devices described herein. The bellows design can be part of the proximal end assembly (as described with reference to FIGS. 8A-8D) that applies force to a target area. The bellows can be designed so that the bellows do not apply a force and instead will compress or crumble easily when the user applies force to the skin perfusion pressure determination device at a target area. The cross-sectional views of the bellows designs are illustrated on the right most image in FIGS. 23A-23C.

The bellows designs of FIG. 23A-23C can include sections where the walls are thinned down to enable the bellows to collapse. The thinned wall sections are illustrated in the cross-section shown in FIG. 23A-23C. The thinned walls can allow for a controlled way of bending and collapsing and a controlled compression and extension of the bellows. The controlled bending of the bellows can protect the components positioned within the bellows. As discussed herein, the skin perfusion pressure determination device includes an interior chamber with one or more PCB, electronic components, and/or electrical wiring. The contraction of the bellows during the application of force to the target area can reduce breakage of the one or more PCB, electronic components, and/or electrical wiring. The minimum kick out of the bellows can provide greater protection for not trapping the PCB or wires and preventing the pinch of the edges of the bellows during contraction.

FIG. 23A illustrates a bellows design with an abrupt material cut-outs that provide a shallow kick out. The bellows design illustrated in FIG. 23A can also have a softer outer radius. FIG. 23B illustrates a bellows design with a gradual varied material thickness and a softer inner radius. The bellows design illustrated in FIG. 23B provides a pronounced kick out when the bellows are contracted. FIG. 23C illustrates a bellows design with sharp inner cut-outs and a controlled and minimized kick out of the bellows when contracted.

Figure 24A:
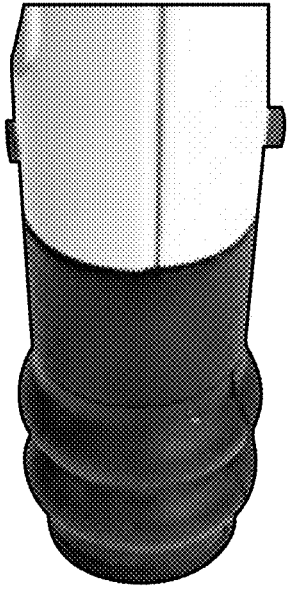
FIGS. 24A-24B illustrate an embodiment of a proximal end assembly with a bellows design.
Figure 24B:
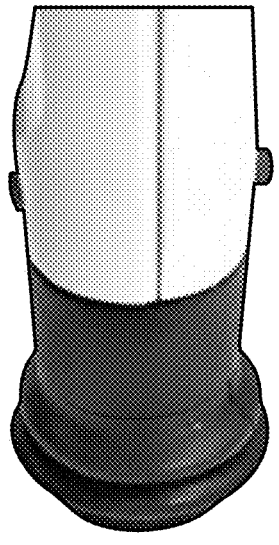
Figure 24C:
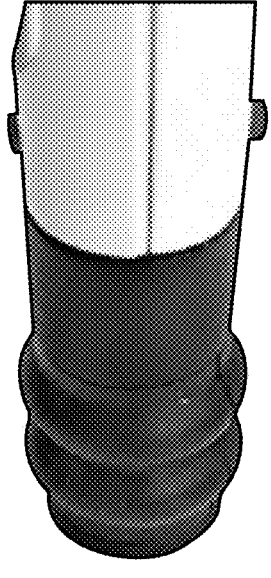
FIGS. 24C-24D illustrate embodiments of a proximal end assembly with different bellows designs.
Figure 24D:
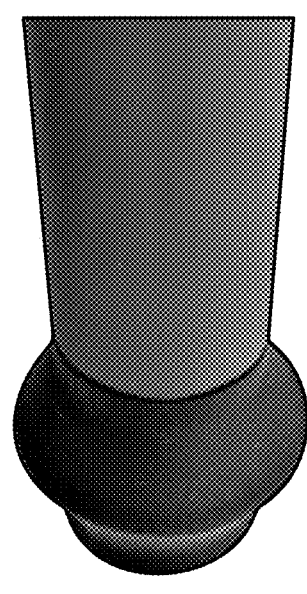

FIGS. 24A-24B illustrate an embodiment of a proximal end assembly with a bellows design. FIG. 24A illustrates the bellows in an expanded configuration and FIG. 24B illustrates the bellows in a contracted configuration. FIGS. 24C-24D illustrate embodiments of a proximal end assembly with different bellows designs.

Figures 25A, 25B:
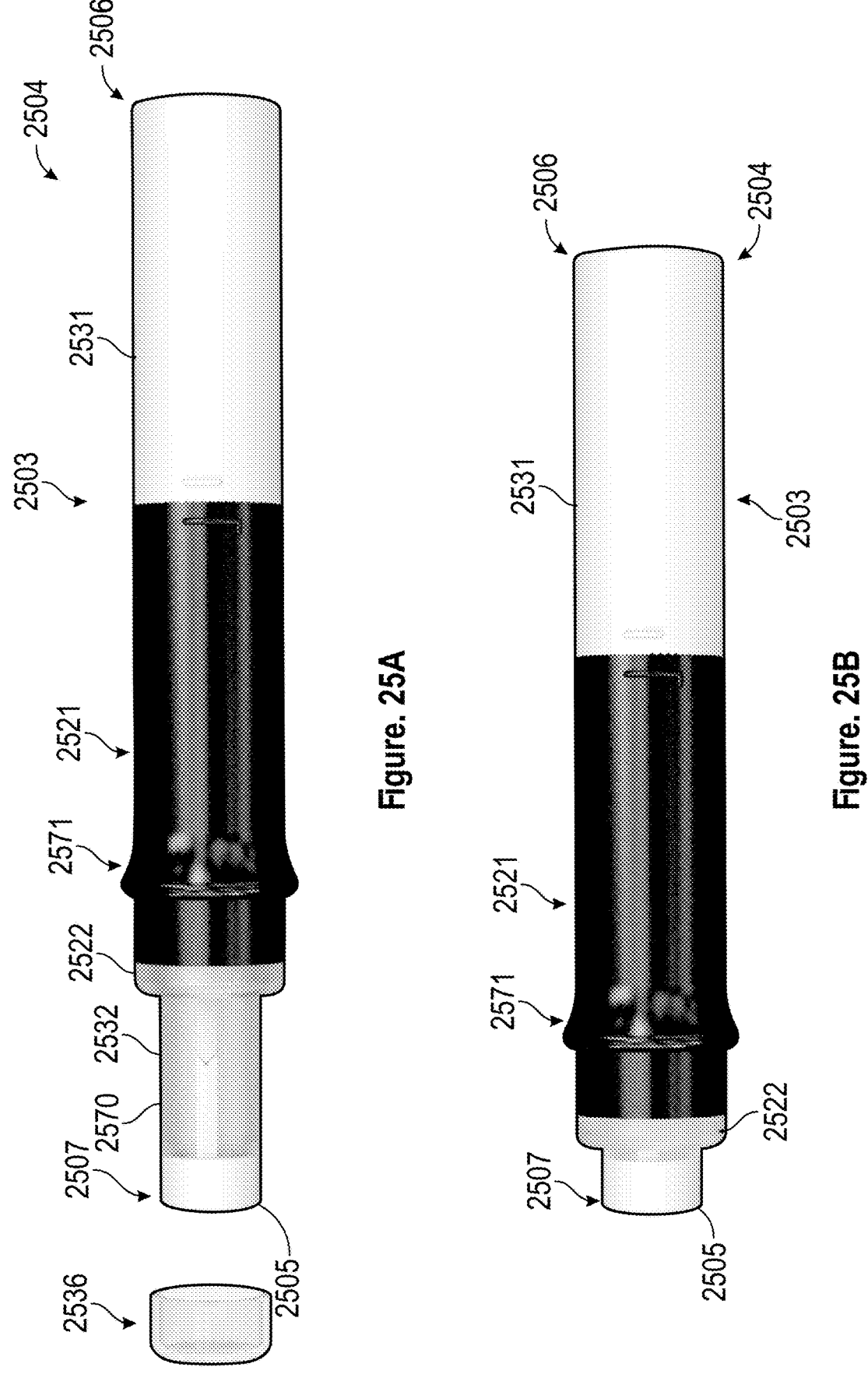
FIGS. 25A-25G and 26A-26B illustrate an embodiment of a skin perfusion pressure determination device with a plunger assembly.

FIGS. 25A-25G illustrate an embodiment of a skin perfusion pressure determination device. The skin perfusion pressure determination device of FIGS. 25A-25G can be similar to and can include similar components as the skin perfusion pressure determination device described with reference to FIGS. 7A-7B and 8A-8B. The skin perfusion pressure determination device 2504 can be a hand-held device with an elongate housing 2503 including a grip portion 2521 and a casing 2531. The grip portion 2521 and casing 2531 can be cylindrical tube like housings. The grip portion 2521 and the casing 2531 can act as a housing or casing enclosing the interior of the skin perfusion pressure determination device. The skin perfusion pressure determination device 2504 can include a proximal end 2507 and a distal end 2506. The skin perfusion pressure determination device 2504 can have a tissue contacting portion 2505 at the proximal most end of the device. The skin perfusion pressure determination device 2504 can include a plunger assembly 2570 that can move relative to the grip portion 2521 and the casing 2531 of the housing. The plunger assembly 2570 can include a sleeve 2532. The skin perfusion pressure determination device 2504 can include an indicator portion 2522. The indicator portion can be a part of the elongate housing that is formed from a translucent or transparent material as illustrated in FIGS. 25A and 25B. As illustrated in FIG. 25A, the skin perfusion pressure determination device 2504 can be provided with a removable and/or replaceable cover 2536 which can be used to cover the tissue contacting end 2505. The cover 2536 can be similar to the cover described herein with reference to other skin perfusion pressure determination device embodiments. In other cases, the skin perfusion pressure determination device 2504 can be used without a cover and instead the proximal end cap of the skin perfusion pressure determination device 2504 can be cleaned between use or application.

The skin perfusion pressure determination device can be sterilized or cleaned in various ways between use. In some cases, the tip can be sterile. In some cases, the tip or proximal end cap (described in more detail below) could be disposable. In some cases, the tip or proximal end cap can be cleaned and not sterile. The skin perfusion pressure determination device can have the ability to be cleaned between uses and/or patients. In some cases, the proximal end of the skin perfusion pressure determination device can be cleaned with isopropyl alcohol (IPA) or ethanol wipes. In some cases, the skin perfusion pressure determination device can be cleaned with an autoclave. In some cases, the skin perfusion pressure determination device can be cleaned or sanitized using some other disinfectant. In some cases, the skin perfusion pressure determination device can be cleaned or sanitized by placing the device in a container or receptacle of cleaning fluid, for example, alcohol or disinfectant.

In some cases, the skin perfusion pressure determination device can have a seal between the grip portion 2521/casing 2531 and the plunger assembly 2570 with the intent of preventing ingress of contaminated liquid or other foreign material from getting into a location that would be difficult to clean. In some cases, the plunger assembly 2570 can be designed to be removable from the grip portion 2521 and the casing 2531 and both the plunger assembly 2570 and the grip portion 2521 and the casing 2531 can be designed to allow for easy cleaning, sanitation, and/or sterilization prior to or between use.

FIGS. 25A-25B illustrate an embodiment of a skin perfusion pressure determination device 2504 with a grip portion 2521 that can encourage appropriate use of the skin perfusion pressure determination device 2504 by the user. The grip portion 2521 can be designed to require the user to hold the skin perfusion pressure determination device 2504 in a certain configuration as described herein. The skin perfusion pressure determination device 2504 illustrated in FIGS. 25A-25B can be held by the user like a pen, for example, between a thumb and index finger of the user. A grip where the device is positioned between the thumb and index finger of the user can be referred to herein as the pen grip or the external precision grip where the device is pinched between the thumb and index finger and the grip has extra components of support for the device in the cleft of the thumb and support for the whole hand along its medial edge. As illustrated in FIGS. 25A-25B, the grip portion 2521 can include a flared portion 2571. The flared portion 2571 can provide for slip protection. In some cases, the skin perfusion pressure determination device 2504 can be sized (with an appropriate diameter) to be held comfortably within the hand of a user in a pen grip. This hold and configuration can enable a controlled force application onto the tissue area. In some cases, the flared portion 2571 can assist in keeping the user's hands or fingers away from the plunger assembly. In some cases, the body of the grip portion 2521 can be between 10 mm to 40 mm (about 10 mm to 40 mm) and the flared portion 2571 can be between 1 mm to 10 mm (about 1 mm to 10 mm) wider than the body of the grip portion 2521. Therefore, the total diameter of the flared portion 2571 (body of grip portion including the flared portion) can be between 11 mm-50 mm (about 11 mm-50 mm). In some cases, the body of the grip portion 2521 can be 8 mm to 16 mm (about 8 mm to about 16 mm. In some cases, the body of the grip portion 2521 can be 16 mm (about 16 mm). In some cases, the surface contour of the flared portion 2571 can be 2 mm to 3 mm (about 2 mm to about 3 mm).

Figure 25D:
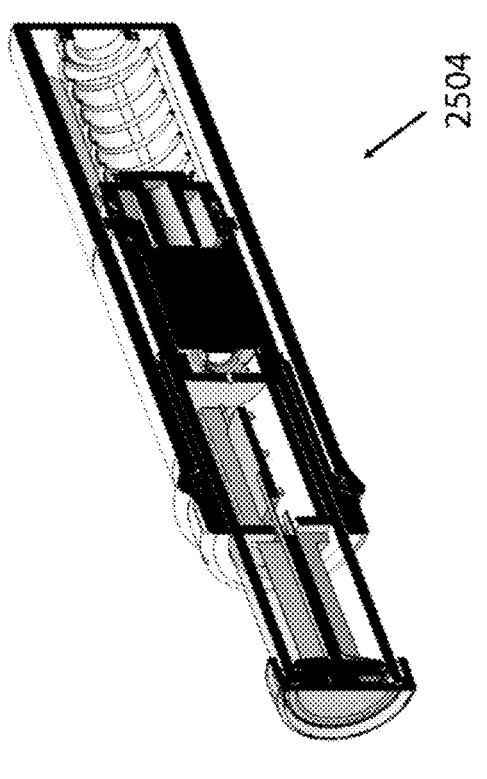
Figure 25C:
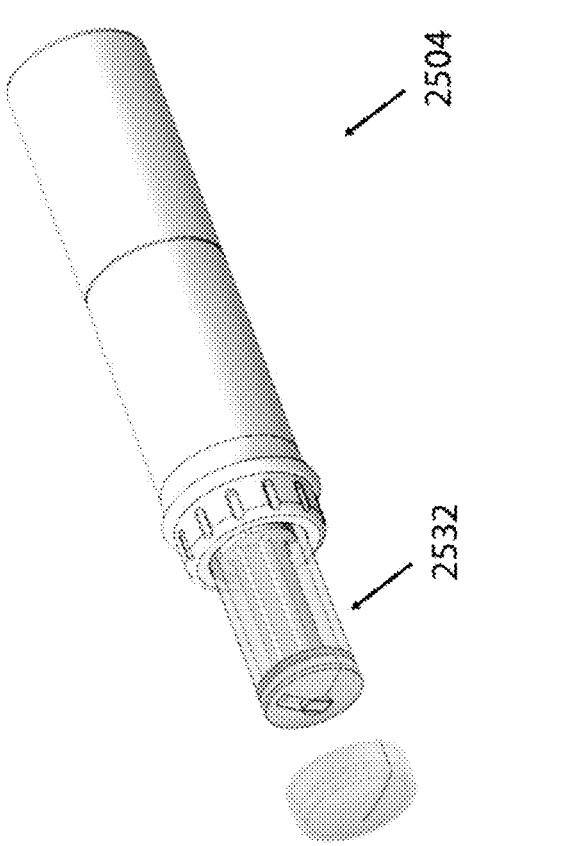

FIG. 25C illustrates an embodiment of the skin perfusion pressure determination device 2504 illustrating the transparent or translucent nature of the sleeve 2532.

FIG. 25D illustrates a cross sectional perspective view of an embodiment of the skin perfusion pressure determination device 2504.

Figure 25E:
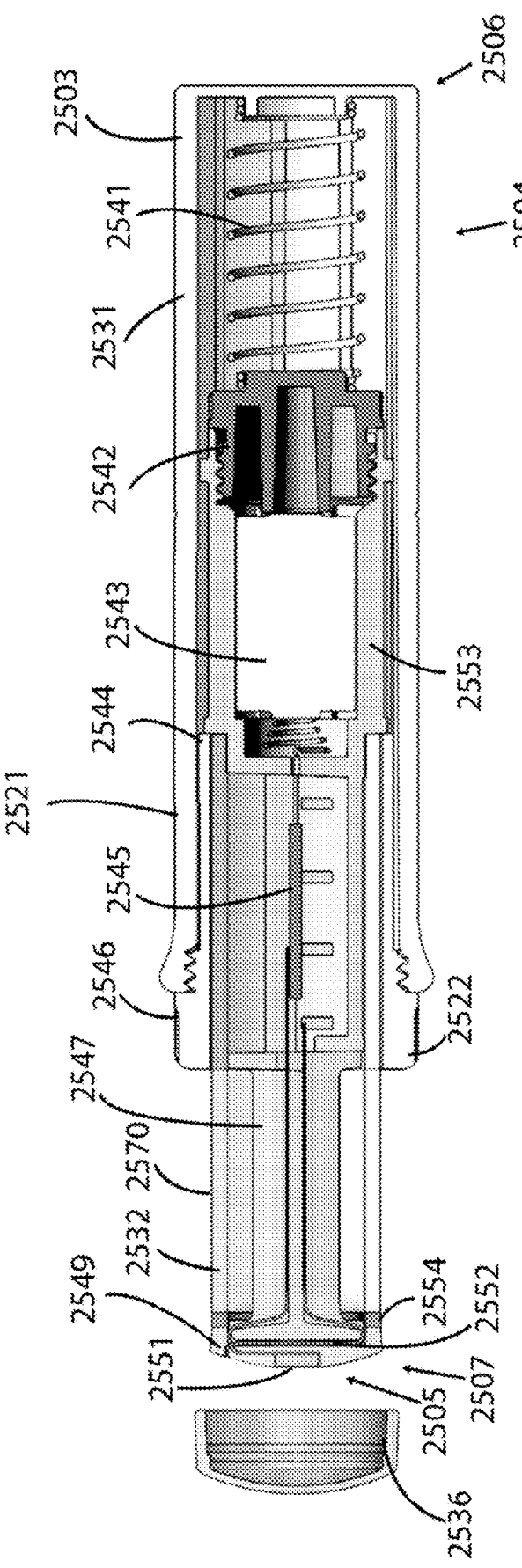

FIG. 25E illustrates a cross sectional view of an embodiment of the skin perfusion pressure determination device 2504. The skin perfusion pressure determination device 2504 can include an elongate housing 2503 that includes the casing 2531, the grip portion 2521, and the sleeve 2532 that enclose the components of the device. The elongate housing 2503 can also include a collar 2546 at the proximal end of the grip portion 2521. In some cases, at least a portion of the collar 2546 can be transparent or translucent and can incorporate the indicator portion 2522. In some cases, the flared portion 2571 of the grip portion 2521 can assist in keeping the user's hands or fingers away from the indicator portion 2522. The sleeve 2532 can move relative to the collar 2546 and move in and out of the collar 2546 as the skin perfusion pressure determination device 2504 is pressed against the skin of the patient. The sleeve 2532 can move along an axis that runs from the proximal end 2507 to the distal end 2506 of the skin perfusion pressure determination device 2504 and the sleeve 2532 is retracted into and extended from the reminder of the housing 2503. A stop feature 2544 can be incorporated into the housing to stop the sleeve 2532 when the sleeve 2532 is retracted into the housing 2503.

The interior of the housing 2503 can include a spring 2541 at the distal end of the device as illustrated in FIG. 25E. The proximal end of the spring 2541 can be in contact with a battery cap 2542 that encloses a battery 2543 within a battery compartment 2553. In some cases, the battery compartment 2553 can include one or more battery contacts for providing electrical communication with the battery and/or other components.

Figure 25F:
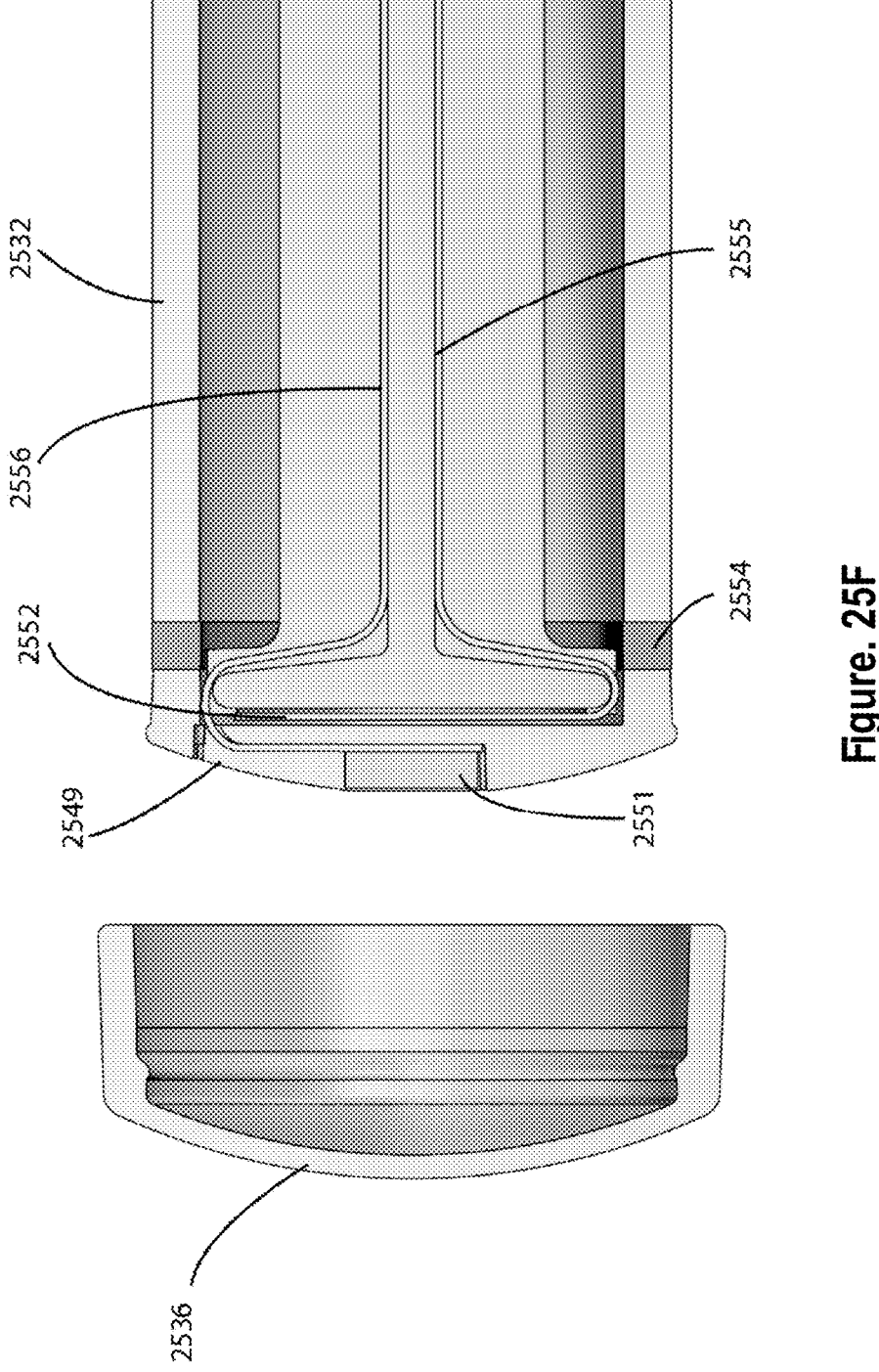

As illustrated in FIG. 25E, a PCB and/or other electronics 2545 can be positioned on and/or within a chassis or support structure 2547. The proximal end 2507 of the device can incorporate an optical sensor 2551 as illustrated in FIGS. 25E and 25F. The optical sensor can be positioned on and/or within a proximal end cap 2549 with an optical sensor window. The end cap 2549 can be sealed to the sleeve 2532 with a gasket 2554. In some cases, the gasket 2554 can be a silicone bead gasket. The skin perfusion pressure determination device 2504 can also include a force sensor 2552 positioned on the proximal end of the skin perfusion pressure determination device 2504. The force sensor 2552 can be distal to the optical sensor 2551 and proximal to the PCB and/or other electronics 2545.

FIG. 25F illustrates a zoomed in view of the proximal end of the skin perfusion pressure determination device 2504 embodiment shown in FIG. 25E. The positioning of the optical sensor 2551 and an optical sensor ribbon cable 2556 at the proximal most end of the device is illustrated in FIG. 25F. As illustrated in FIG. 25F, the force sensor 2552 can be positioned distal to the optical sensor 2551. A force sensor ribbon cable 2555 can extend from the force sensor 2552 as illustrated in FIG. 25F. The optical sensor ribbon cable 2556 and the force sensor ribbon cable 2555 can allow for the optical sensor 2551 and the force sensor 2552 to communicate with the PCB and/or other electronic components 2545 (shown in FIG. 25E).

FIG. 25F illustrates a cover 2536 that can cover the proximal most end of the skin perfusion pressure determination device 2504. The cover can be a single use cover that clips directly onto the proximal most end cap 2549 with the optical sensor window. The cover can be molded in a clear, transparent, or translucent material as described herein with reference to other cover embodiments. The material of the cover can be selected so as not to interfere with the use and measurement conducted with the optical sensor.

Figure 25G:
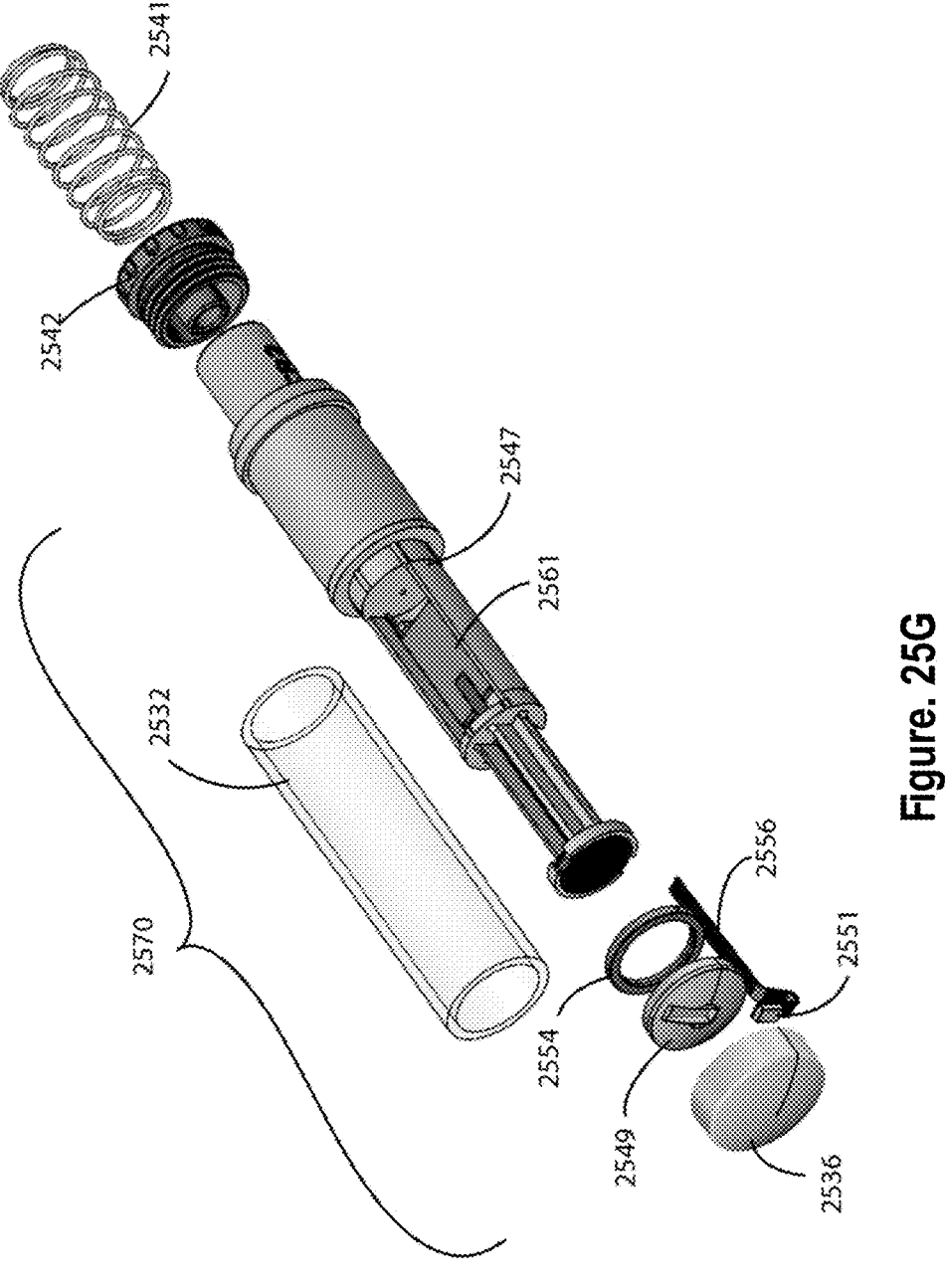

FIG. 25G illustrates an exploded view of the interior components of the skin perfusion pressure determination device 2504. The spring 2541 can have a spring constant of between 0.1 N/mm to 2 N/mm. FIG. 25G illustrates the removeable battery cap 2542. The battery cap 2542 can be sealed to the battery compartment with a sealing mechanism (for example, an o-ring sealing mechanism). In some cases, the removeable battery cap 2542 can be threaded and can align with complementary threading within the battery compartment. The chassis or support structure 2547 can act as a battery compartment, PCB support, light pipe, ribbon cable support, and/or force sensor platform. In some cases, the support structure 2547 can be molded in clear plastic or some translucent or transparent material. As illustrated in FIG. 25G, the support structure 2547 can support the PCB 2561 and an LED (not shown). The LED can be incorporated onto the PCB 2561. In some cases, the LED can be positioned on the proximal edge of the PCB and can provide lighting into the sleeve and/or collar portion of the housing. The features of the chassis or support structure 2547 can act as a light pipe to disperse the light from the LED uniformly. This can allow the at least partially transparent or translucent portion of the collar 2546 (shown in FIG. 25E) to act as an indicator portion 2522 (shown in FIGS. 25A, 25B, and 25E) and display the light emitted from the LED. In some cases, more than one LED can be used to increase the intensity of the LED or to provide different colors of LED to emit different colors. In some cases, if the sleeve is at least partially translucent or transparent, the light emitted from the LED can also be seen in at least part of the sleeve 2532.

In some cases, the indicator portion 2522 can allow for a circumferential visual guide illuminated by a LED. For example, a color or multiple colors can be used to guide the user through the procedure and application of force during use of the device. In some embodiments, the visual guide can use any LED or arrangement of LEDs, not necessarily circumferential, to guide the user through the procedure.

In some cases, the indicator portion 2522 can be positioned at a portion of the skin perfusion pressure determination device 2504 that is in close proximity of the grip portion. This can allow the user to receive information and/or feedback from the visual indicator as they hold the device and use it.

In some cases, the sleeve 2532 can be a frosted or partially obscuring material that allows for transmission of light and the light emitted by the LEDs to be visible through the material but can obscure the interior components of the skin perfusion pressure determination device so the interior components are not visible from the outer surface of the device. The sleeve 2532 can be positioned around at least a portion of the chassis or support structure 2547 to cover and/or seal the PCB and/or other electronic components.

In some cases, the light emitted from the LED can be visible at the proximal end of the collar 2546 forming the indicator portion 2522. In some cases, the light emitted from the LED can be visible at the proximal end of the collar 2546 and/or from the external surface of the sleeve and either or both of these areas can form the indicator portion 2522. The LED can be located on the PCB. In other cases, the LED can be attached to the PCB via a flexible PCB or wire. This can allow the LED to be local to the area being illuminated. In some cases, the LED can be positioned within the interior of the housing but remote form the PCB. In some cases, the indicator portion 2522 can allow for uniform circumferential illumination around the device. In some cases, the light emitted by the LED can illuminate the proximal end of the collar, a portion of the sleeve, and/or the grip portion. In some cases, the light emitted by the LED can act as a dual visual feedback system for the user. The LED can change intensity, blink, change color, or use a sequence of flashes to indicate different states to the user. In some cases, feedback can also be displayed on a display that is incorporated into the skin perfusion pressure determination device 2504 or a remote display. In some cases, the display can be a PC/Tablet GUI. The display can provide an indication or feedback to the user that mirrors the indication or feedback provided by the light emitted by the LED on the skin perfusion pressure determination device 2504. The user can then choose to use whichever (or combination of) feedback system they want to take the reading and use the device. For example, if the pen is removed too fast the LED/GUI will display a visual indicator (e.g. LED flashing yellow/audible feedback from GUI) to indicate this state.

In some cases, the reading can be taken with the skin perfusion pressure determination device without a display. For example, in some cases, no feedback can be provided beyond the feel of pushing the plunger assembly down until the spring is coil bound and then the user can slowly release. In other examples, the skin perfusion pressure determination device can use acoustic feedback and/or haptic feedback.

FIG. 25G illustrates the skin perfusion pressure determination device 2504 in a first configuration with a plunger assembly 2570. The plunger assembly 2570 can include the chassis or support structure 2547 and sleeve 2532 and their associated components. At least a portion of the plunger assembly can be positioned within the portion of the housing comprising the grip portion and/or the casing of the housing. As described herein, the grip portion and/or casing can be a housing or casing enclosing and/or surrounding at least some of the components of the skin perfusion pressure determination device 2504. In some cases, the grip portion and/or casing can be a hollow cylindrical housing or casing.

As illustrated in FIG. 25A, a portion of the exterior surface of the plunger assembly 2570 (for example, the sleeve) can extend from the grip portion of the housing 2503. In use the proximal end 2507 of the skin perfusion pressure determination device 2504 can be applied to the tissue area. As force is applied to the target area by the skin perfusion pressure determination device 2504 the support structure 2547 and sleeve 2532 of the plunger assembly 2570 can retract within the grip portion and/or casing of the housing and can exert a force on the spring 2541 causing the spring to compress. As the spring 2541 compresses, the plunger assembly 2570 formed from the support structure 2547 and sleeve 2532 can move along the axis of the skin perfusion pressure determination device 2504 that extends from the proximal end to the distal end of the skin perfusion pressure determination device 2504. When the spring is in a compressed state, the plunger assembly 2570 can be in a second configuration where it is retracted into the grip portion 2521 and casing 2531 of the housing 2503 as illustrated in FIG. 25B. As the force applied to the tissue area is released, the spring can expand and push the plunger assembly 2570 out of the housing 2503 back to the first configuration illustrated in FIG. 25A. The movement of the plunger assembly 2570 into and out of the grip portion 2521 and casing 2531 of the housing 2503 can be controlled by the amount the spring 2541 is compressed or expanded. In some cases, the spring constant can range from 0.1 N/mm (about 0.1 N/mm) to 2 N/mm (about 2 N/mm). In some cases, the spring constant can be less than 0.1 N/mm, 0.1 N/mm to 2 N/mm, or greater than 2 N/mm.

Positioning the force sensor 2552 at a proximal end of the device can allow for a force measurement to be taken without being affected by the friction forces in the barrel as the force reading is taken directly at or almost directly at the surface instead of indirectly further inwards or distally in the assembly where friction may alter the measurement since the force sensor is subject to additional forces.

Figure 26A:
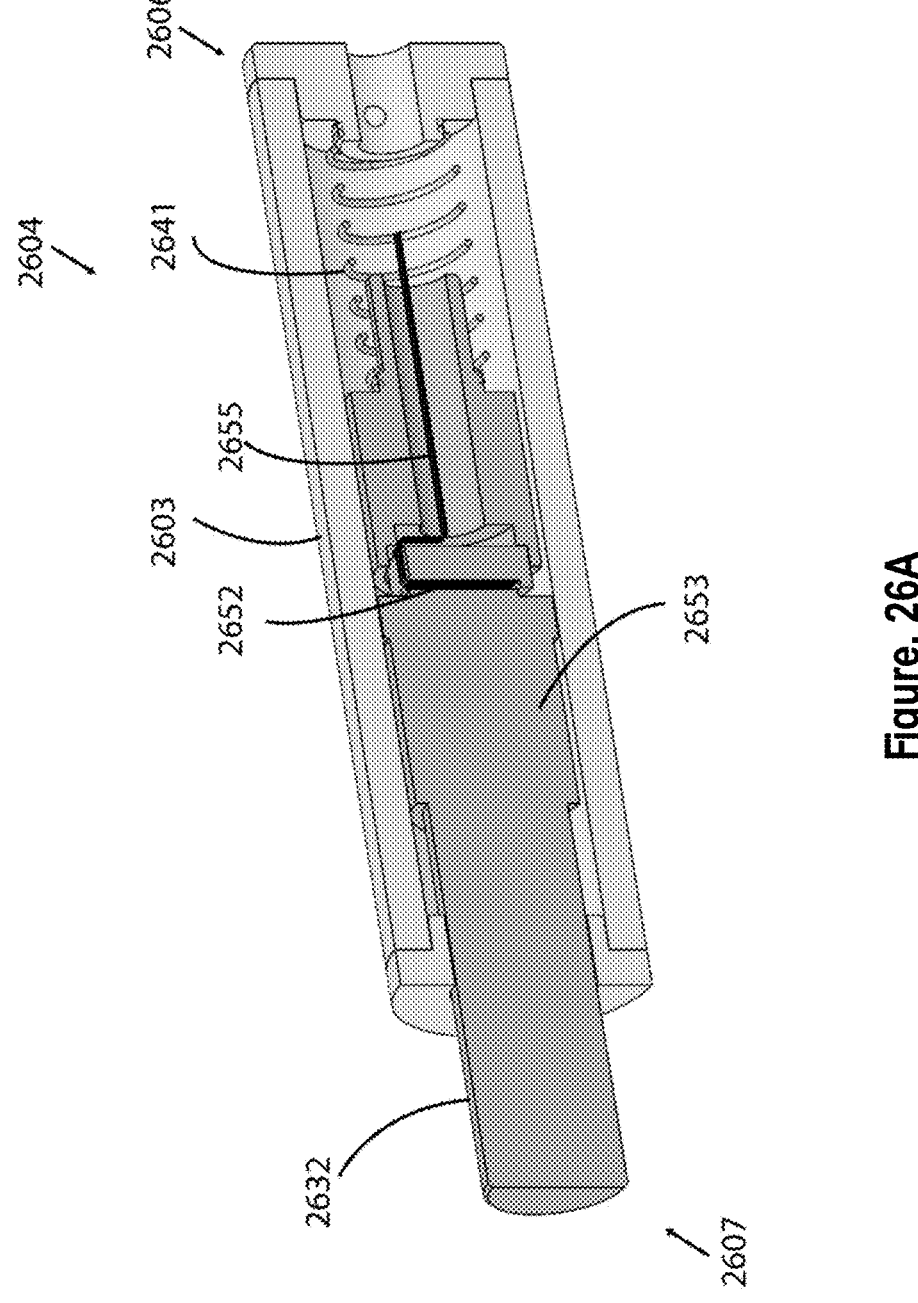
Figure 26B:
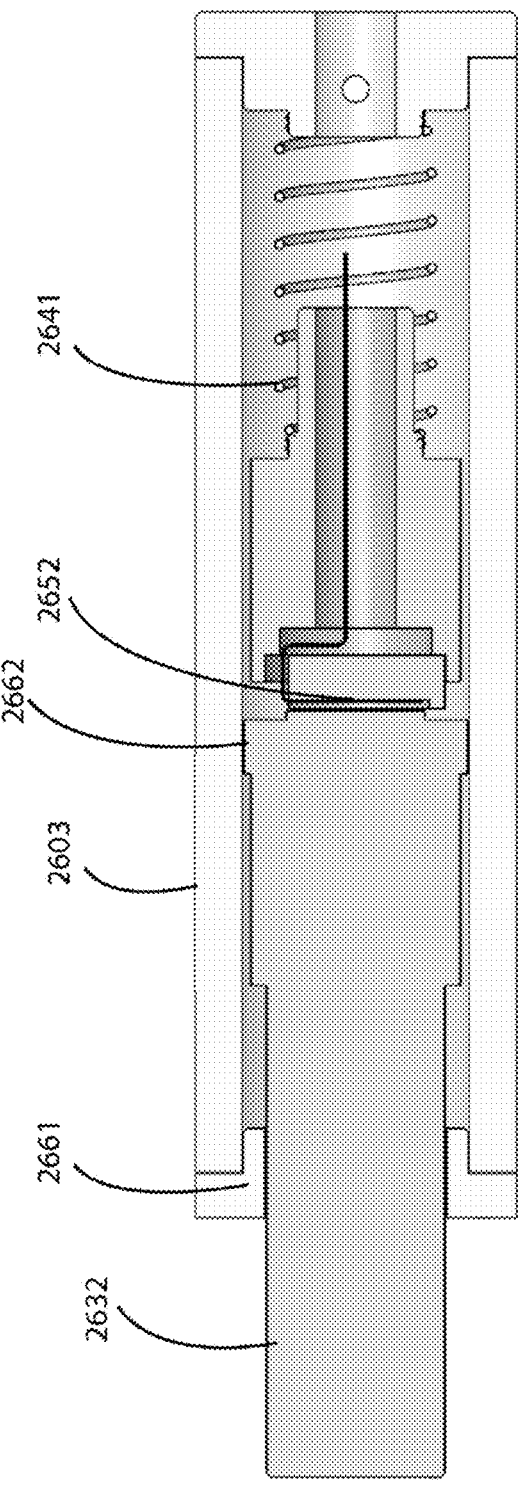

FIGS. 26A-26B illustrate an embodiment of the skin perfusion pressure determination device 2604. The skin perfusion pressure determination device 2604 illustrated in FIGS. 26A-26B is similar to the skin perfusion pressure determination device 2504 illustrated in FIGS. 25A-25G and the skin perfusion pressure determination device 2604 can incorporate the same components and features as the skin perfusion pressure determination device 2504. FIG. 26A illustrates a cross section of the skin perfusion pressure determination device 2604, however, not all the interior components are shown for simplicity. The interior components of the skin perfusion pressure determination device 2604 can be the same as interior components of the skin perfusion pressure determination device 2504 except the force sensor 2652 can be positioned in a portion of the housing 2603 that is at the distal end of the plunger assembly 2570 formed from the sleeve 2532 and battery compartment 2653 and proximal to the spring 2641 as illustrated in FIG. 26A. The force sensor 2652 can include a force sensor ribbon cable 2566 that extends distally. The force sensor ribbon cable 2566 can connect to the internal PCB.

FIG. 26B illustrates a cross-sectional view of the skin perfusion pressure determination device 2604 with some of the forces that can impact the force measurement due to the movement of the sleeve and chassis or support structure within the housing 2603. As force is applied to the proximal end cap of the skin perfusion pressure determination device 2604 by contacting the tissue with the proximal end cap, the sleeve 2632 can move within a portion of the housing 2603. The sleeve 2632 can contact the housing 2603 at a first contact point 2661 and a second contact point 2662. Each of these contact points can create friction or other forces that may impact the force measurement of the device. In some cases, lateral forces on the proximal end cap or sleeve, such as forces applied to the side for the sleeve or proximal end cap can also impact the force reading. The force sensor measurement can account for these varied forces or friction that can impact an accurate force reading of the force applied to the tissue area.

Figures 27A, 27B, 27C, 27D, 27E, 27F:
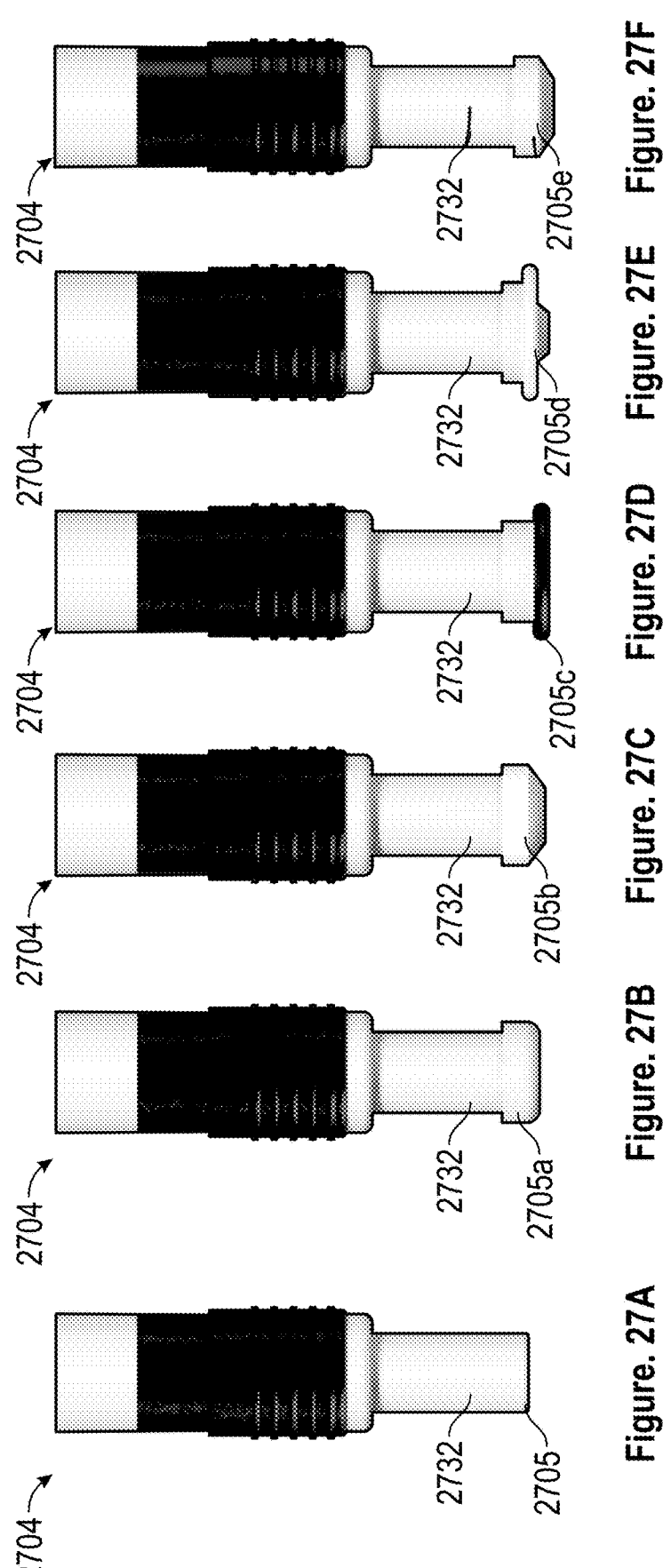
FIGS. 27A-27F and 28A-28E illustrate embodiments of shapes and configurations of the proximal end cap of the skin perfusion pressure determination device.
Figures 28A, 28B, 28C, 28D, 28E:
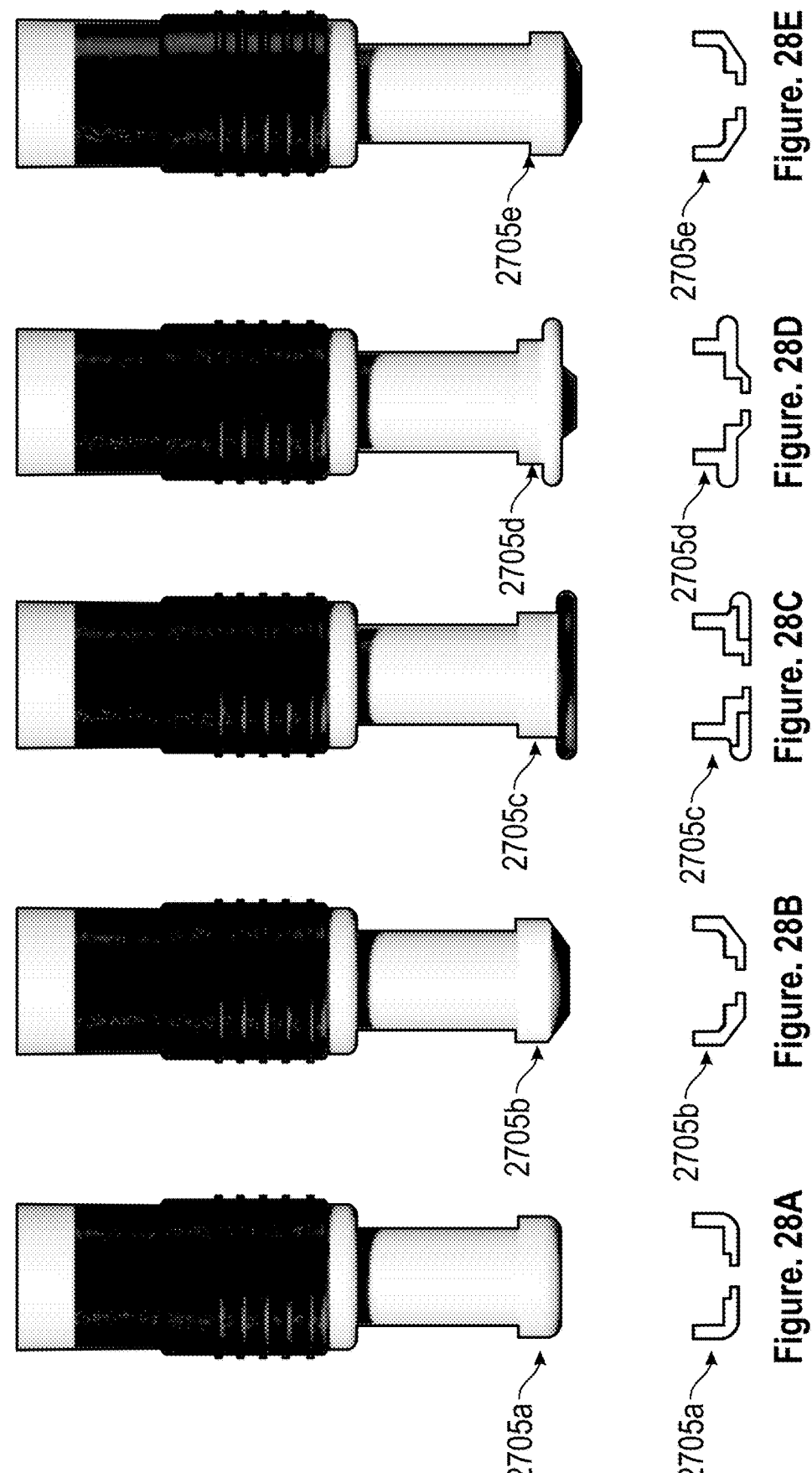

FIGS. 27A-27F and 28A-28E illustrate various embodiments of shapes and configurations of the proximal end cap of the skin perfusion pressure determination device. FIGS. 27A-27F illustrate different proximal end cap shapes that can be used. In some cases, as illustrated in FIG. 27A, the proximal end cap 2705 can have a flat proximal portion and a diameter that is the same as (or substantially the same as) the diameter of the sleeve 2732 and the circumference of the proximal end cap is flush with the circumference of the sleeve. In some cases, as illustrated in FIGS. 27B, 27C, and 27F, the proximal end cap 2705a, 2705b, and 2705e can have a diameter that is greater than the diameter of the sleeve 2732. This can allow for a greater surface area to contact the tissue area than the surface area of 2705. This increased surface area can more evenly distribute the force applied to the tissue area. In some cases, the proximal end cap 2705a can include curved edges along the circumference of the proximal most end of the end cap as shown in FIG. 27B. In some cases, the proximal end cap 2705b can include tapered edges along the circumference of the proximal end of the end cap as shown in FIG. 27C. In some cases, the proximal end cap 2705e can have a domed shape at the proximal end of the end cap as shown in FIG. 27F. In some cases, the proximal end cap can have a flanged end similar to the proximal end cap 2705c and 2705d illustrated in FIGS. 27D and 27E. The flanged end can provide an increased surface area that is greater than the cross-sectional area of the sleeve 2732 of the skin perfusion pressure determination device 2704. In some cases, the proximal end cap 2705d can include a flanged end as well as a proximal nipple portion as illustrated in FIG. 27E. The flanged area of the proximal end cap 2705d can reduce point pressure as it spreads pressure out across the application area. The nipple section of the proximal end cap 2705d can help to create the occlusion of blood local to the sensor at the measurement location as it can be the first part to touch the tissue, and then the remainder of blood peripheral to the measurement location can be spread outwards from the sensor as pressure is applied with the flanged section. Additionally, the nipple portion can concentrate the force in the center of the pen and therefore the total force which needs to be applied by the user can be less than it is in the case of the proximal end cap 2750 in FIG. 27A. Having to apply less force can be beneficial to the user and enables better force control. This configuration can also enable force sensors with a lower range and therefore potentially less noise to be used. The same benefits can be seen with the other embodiments that allow for the less force to be applied.

The proximal end caps illustrated in FIGS. 27A-27F can contact the target tissue area and provide the necessary surface area that will allow for the target area to be blanched or occluded as well as allow for a sensor (i.e. located as a component in the interior of the device) to monitor the blood flow synchronously with the application of pressure over the surface area. In some embodiments, the proximal end cap of the skin perfusion pressure determination device can provide a larger surface area to contact the skin by use of the flanged end or some other means extended outwards in the plane of the skin to stabilize the device on the target area and rest the device flat on the target area. In some embodiments, the proximal end cap of the skin perfusion pressure determination device can be domed to ensure even pressure distribution and contact with the target area. In some embodiments, a domed surface (for the purpose of even pressure distribution over the target area where the sensor is located) can be used with an in-plane flange to provide stabilization of the sensor head in the plane of the target area.

FIGS. 28A-28E illustrate the proximal end caps shown in FIGS. 27B-27F with a corresponding cross sectional view of the proximal end cap. The gap in the middle of the proximal end caps shown in FIGS. 28A-28E correspond to the area that holds the optical sensor or a window that allows transmission of light to and from the optical sensor. The surface of the proximal end cap that contacts the tissue area can have a diameter that ranges from 4 mm (about 4 mm) to 30 mm (about 30 mm). In some cases, the surface of the proximal end cap that contacts the tissue area can have a diameter that is less than 4 mm, between 4 mm (about 4 mm) and 30 mm (about 30 mm), or greater than 30 mm. In some cases, only a portion of the proximal end cap needs to contact the tissue area to take the measurement necessary. In such cases, only a portion of the diameter would be in contact with the tissue area.

In some cases, a cover can be used with any of the proximal end cap shapes described in FIGS. 27A-27F and 28A-28E. In some cases, the cover can mirror the shape of the proximal end cap. In other cases, the proximal end cap can be flat similar to the proximal end cap 2705 illustrated in FIG. 27A and a shaped cover can be used. The shaped cover can be domed, have a flanged end, or can be any other shape to provide pressure distribution.

In some cases, the proximal end cap or proximal end of the device can have some beveling and/or doming of the tip to allow the pressure to be distributed across the soft tissue it is pushing onto. In some cases, an increasingly homogenous occlusion of capillaries under the tip can be accomplished with the shape of the proximal end cap or the proximal end of the skin perfusion pressure determination device. In some cases, the proximal end cap or the proximal end of the skin perfusion pressure determination device can be bevel, taper, and/or dome shape.

In some cases, the skin perfusion pressure determination device can be used to capture various measurements. First, a force can be applied to a target area with the proximal end of the skin perfusion pressure determination device and blood flow is occluded. The force at which blood flow is occluded can be the data point captured. The measurement can end and a pressure can be calculated if desired.

In another case, a force can be applied to a target area with the proximal end of the skin perfusion pressure determination device and blood flow is occluded. Then the force applied can be reduced and blood flow can be restored. The force at which blood flow is restored can be the data point captured. The measurement can end and a pressure can be calculated if desired.

In another case, a force can be applied to a target area with the proximal end of the skin perfusion pressure determination device and blood flow is occluded. Then the force applied can be reduced and blood flow can be restored. The force at which blood flow is occluded and blood flow is restored can be the data captured. The measurement can end and pressure can be calculated for these two data points if desired.

It will be appreciated that the blood perfusion sensor may comprise other types of optical sensors or may be a non-optical sensor, the skin perfusion pressure determination device could comprise other types of data storage devices. It will also be appreciated that, where applicable, each embodiment described previously could be modified so that recorded data is processed and/or stored locally on a skin perfusion pressure determination device or transmitted for remote processing and/or storage and vice versa.

The embodiments described above comprise a sensor module which is configured such that an optical sensor can be positioned adjacent the skin and a force sensor is located above the optical sensor. Other possible arrangements include a sensor module in which a force sensor and an optical sensor are arranged such that, in use, the force sensor is placed next to a target region of skin tissue and the optical sensor is positioned above the force sensor. In such an arrangement, the force sensor may comprise through-holes or transparent portions through which light can be transmitted.

In some cases, an accelerometer, magnetometer, gyroscope, any other sensor, a comparison to an external feature, and/or tilt sensor can be used to determine the angle of application of force. Knowing the angle of application of force can allow for numerical compensation for this angle and/or warning of the user if this angle gets too large as this can impact the reading. In some cases, reaching certain angular points can prevent a reading from being taken, or the data from being reliable.

In any embodiment of the claims where the term "pressure" is used, the term "pressure" is considered to be interchangeable with "force." For example, with respect to Claim 1 of the PCT application as filed, a skin perfusion pressure determination device may be configured to exert a force on the target area and a sensor module may be configured to detect a force exerted on the target area. Moreover, the display can display a force or a calculated pressure.

As another example, with respect to Claim 7 of the PCT application as filed, a skin perfusion pressure determination device may be configured to exert a force on the target area and a sensor module may be configured to detect a force exerted on the target area.

As another example, with respect to Claim 9 of the PCT application as filed, a skin perfusion pressure determination device may be configured to exert a force on the target area and a sensor module may be configured to detect a force exerted on the target area. Additionally, another example, with respect to Claim 12 of the PCT application as filed, the liquid filed piston can exert a force on the intermediate platform. Another example, with respect to Claim 14 of the PCT application as filed, the ratchet arm can be configured to exert a force on the spring.

As another example, with respect to Claim 17 of the PCT application as filed, a skin perfusion pressure determination device may be configured to exert a force on the target area and a sensor module may be configured to detect a force exerted on the target area.

In the drawings like reference numerals refer to like parts.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The disclosure is not restricted to any details of any foregoing embodiments. The disclosure extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A skin perfusion pressure determination device comprising:
  a housing including a proximal end and a distal end, the housing comprising a plunger assembly configured to contact and exert force on a target area, the plunger assembly comprising:
    a casing with a grip portion; and
    a sleeve configured to move in a proximal to distal direction relative to the casing from a first expanded configuration in which the sleeve extends proximally from the proximal end of the casing to a second retracted configuration in which the sleeve is retracted into the casing responsive to a force being exerted on the target area;
  one or more sensors positioned within the housing, the one or more sensors configured to detect a force exerted on the target area and an amount of blood perfusion at the target area; and
  an output interface configured to provide indication of the force exerted on the target area, the output interface comprising an indicator portion;
  wherein the sleeve comprises a partially translucent or transparent material and is configured to allow the indicator portion to be seen in at least part of the sleeve; and
  wherein a portion of the indicator portion is configured to be hidden as the sleeve is moved to a second retracted configuration in which the sleeve is retracted into the casing responsive to a force being exerted on the target area.

2. The skin perfusion pressure determination device of claim 1, wherein the output interface further comprises an LED, wherein the indicator portion is configured to display light emitted from the LED.

3. The skin perfusion pressure determination device of claim 2, further comprising a support structure within the housing, wherein the support structure is configured to support the LED.

4. The skin perfusion pressure determination device of claim 2, wherein light emitted from the indicator portion can indicate different states to the user by one or more of an intensity change, a blink, a color change, and/or a sequence of flashes.

5. The skin perfusion pressure determination device of claim 1, wherein the grip portion is at a proximal end of the casing.

6. The skin perfusion pressure determination device of claim 1, wherein the indicator portion at least partially circumferentially surrounds the housing.

7. The skin perfusion pressure determination device of claim 1, wherein the grip portion is distal to the output interface and comprises a flared portion configured to prevent a user from covering the output interface.

8. The skin perfusion pressure determination device of claim 1, further comprising a spring at the distal end of the housing configured to exert a force on the plunger assembly and control the force exerted on the target area.

9. The skin perfusion pressure determination device of claim 1, further comprising a support structure within the housing, wherein the support structure supports one or more of a sensor, electrical connection for a sensor, a PCB, a battery, battery contacts, and/or an LED.

10. The skin perfusion pressure determination device of claim 1, wherein the one or more sensors comprises a first sensor for sensing a first parameter associated with a force exerted on the target area by the one or more sensors and a second sensor for sensing a second parameter associated with an amount of blood perfusion at the target area, wherein the first sensor and the second sensor are arranged such that, when the one or more sensors are pressed against the target area the first sensor produces an output corresponding to the sensed first parameter and the second sensor produces an output corresponding to the sensed second parameter.

11. The skin perfusion pressure determination device of claim 1, wherein the one or more sensors comprise a first sensor configured to detect the amount of blood perfusion at the target area and/or a second sensor configured to detect the force exerted on the target area.

12. The skin perfusion pressure determination device of claim 11, wherein the first sensor and the second sensor are positioned at a proximal end of the housing.

13. The skin perfusion pressure determination device of claim 11, wherein the first sensor is positioned at a proximal end of the housing and the second sensor is positioned at the distal end of the plunger assembly and proximal to a spring.

14. The skin perfusion pressure determination device of claim 11, wherein the first sensor is an optical sensor.

15. The skin perfusion pressure determination device of claim 11, wherein the second sensor is a force sensor.

16. The skin perfusion pressure determination device of claim 1, wherein the housing is an elongate housing.

17. The skin perfusion pressure determination device of claim 1, wherein the housing comprises a proximal end cap configured to contact the target area, wherein the proximal end cap comprises one or more of a flange shape, a dome shape, a curved shape, a tapered shape, or a nipple shape.

18. The skin perfusion pressure determination device of claim 1, wherein the indicator portion comprises a portion of the grip portion.

19. The skin perfusion pressure determination device of claim 1, wherein the indicator portion comprises a row of indicators on the housing.

* * * * *